US006862561B2

(12) United States Patent
Defranoux et al.

(10) Patent No.: US 6,862,561 B2
(45) Date of Patent: Mar. 1, 2005

(54) METHOD AND APPARATUS FOR COMPUTER MODELING A JOINT

(75) Inventors: Nadine A. Defranoux, San Francisco, CA (US); Todd B. Dubnicoff, Burlingame, CA (US); David J. Klinke, II, San Bruno, CA (US); Annette K. Lewis, Menlo Park, CA (US); Thomas S. Paterson, West Hollywood, CA (US); Saroja Ramanujan, San Mateo, CA (US); Lisl K. M. Shoda, Redwood City, CA (US); Karl Petter Soderstrom, San Francisco, CA (US); Herbert K. Struemper, Menlo Park, CA (US)

(73) Assignee: Entelos, Inc., Foster City, CA (US)

( * ) Notice: Subject to any disclaimer, the term of this patent is extended or adjusted under 35 U.S.C. 154(b) by 231 days.

(21) Appl. No.: 10/154,123

(22) Filed: May 22, 2002

(65) Prior Publication Data

US 2003/0078759 A1 Apr. 24, 2003

Related U.S. Application Data

(60) Provisional application No. 60/293,533, filed on May 29, 2001.

(51) Int. Cl.[7] .............................. G06G 7/48; G06F 17/10
(52) U.S. Cl. ............................................. 703/11; 703/2
(58) Field of Search ........................... 703/22, 2, 6, 11; 607/1; 424/756; 382/128

(56) References Cited

U.S. PATENT DOCUMENTS

| 5,494,668 | A | * | 2/1996 | Patwardhan | ................. 424/756 |
| 5,814,078 | A | * | 9/1998 | Zhou et al. | ..................... 607/1 |
| 6,051,029 | A | | 4/2000 | Paterson et al. | ............... 703/22 |
| 6,069,629 | A | | 5/2000 | Paterson et al. | ............. 345/349 |
| 6,078,739 | A | | 6/2000 | Paterson et al. | ................ 703/6 |
| 6,144,954 | A | | 11/2000 | Li | .............................. 706/62 |
| 6,539,347 | B1 | * | 3/2003 | Paterson et al. | ............... 703/22 |
| 2003/0087285 | A1 | | 5/2003 | Chow et al. | .................... 435/6 |

OTHER PUBLICATIONS

Dullens et al., "A Survey of some formal models in tumor immunology", Cancer Immunogy Immunotherapy (1986) 23:159–164.

Look et al., "Computer simulation of the cellular immune to malignant lymphoid cells: logic of approach, model design and laboratory verification", Immunology (1981) 43:677–690.

Ateshian (1997) "A theoretical formulation for boundary friction in articular cartilage," *Journal of Biomechanical Engineering*, 119:81–86.

Bogoch et al. (1998) "Abnormal bone remodeling in inflammatory arthritis," *Canadian Journal of Surgery*, 41(4):264–271.

Chaplain (2000) "Mathematical modelling of antiogenesis," *Journal of Neuro–Oncology*, 50:37–51.

Clift (1992) "Finite–element analysis in cartilage biomechanics," *J. Biomed. Eng.*, 14:217–221.

Heegaard et al. (1999) "Mechanically modulated cartilage growth may regulate joint surface morphogenesis," *Journal of Orthopaedic Research*, 17(4):509–517.

(List continued on next page.)

*Primary Examiner*—Russell Frejd
(74) *Attorney, Agent, or Firm*—Cooley Godward LLP

(57) ABSTRACT

The present invention relates to a mathematical and computer model of a joint. The model includes representation of the biological processes related to the synovial tissue and cartilage. In one embodiment, the model represents a human joint afflicted with rheumatoid arthritis.

46 Claims, 45 Drawing Sheets

OTHER PUBLICATIONS

Helliwell et al. (2000) "Joint symmetry in early and late rheumatoid and psoriatic arthritis," *Arthritis & Rheumatism*, 43(4):865–871.

Hlavacek (1993) "The role of synovial fluid filtration by cartilage in lubrication of synovial joints—I. Mixture model of synovial fluid," *J. Biomechanics*, 26(10):1145–1150.

Hlavacek (1993) "The role of synovial fluid filtration by cartilage in lubrication of synovial joints—II. Squeeze-film lubrication: homogenous filtration," *J. Biomechanics*, 26(10):1151–1160.

Lane Smith et al. (2000) "Effects of shear stress on articular chondrocyte metabolism," *Biorheology*, 37:95–107.

Beaupre', G.S., et al., 2000, "Mechanobiology in the Development, Maintenance, and Degeneration of Articular Cartilage", *J. Rehabil. Res. Dev.*, 37:145–151.

Pollatschek, M.A., et. al, 1990, "A Mathematical Model of Osteoarthosis", *J. Theor. Biol.*, 143:497–505.

Shi, Q., 1995, "Finite Element Analysis of Pathogenesis of Osteoarthritis in the First Carpometalcarpal Joint", *Acta Med. Okayama*, 49:43–51.

Szekanecz, Z., et al., 2001, "Update on Synovitis", *Curr. Rheumatol. Rep.*, 3:53–63.

Wynarsky, G.T., et al., 1983, "Mathematical Model of the Human Ankle Joint", *J.Biochem.*, 16:241–251.

Lutzenberger, C., et al., 1998, "A Three–Dimensional Model of the Human Locomotor Apparatus for Analysis of Hemiplegic Gait", *Proc. 20th Annual Conference of IEEE Eng. Med. Bio. Soc.*, 2407–2410.

Nielsen, C., et al., 1995, "A Computational Method for Comparing the Behavior and Possible Failure of Prosthetic Implants", *IEEE 17th Annual Conference IEEE Eng. Med. Bio. Soc.*, 2:1251–1252.

Popovic, M. et al., 2001, "Cloning Biological Synergies Improves Control of the Elbow Neuroprostheses", *IEEE Eng. Med. Bio.*, 20: 74–81.

Scheiner, A., 1994, "The Effect of Joint Stiffness on Stimulation of the Complete Gait Cycle", *Proc. 16th Annual Conference of IEEE Eng. Med. Bio. Soc., Engineering Advances: New Opportunities for Biomedical Engineers*: 386–387.

Stokes, C.L., et al., 1999, "Asthma PhysioLab: A Dynamic, Computer–Based Mathematical Model of Acute and Chronic Asthma", *Proc. First Joint BMES/EMBS Conf. Serving Humanity, Advancing Technology*, Oct. 13–16: 1208.

Yvan, P., et al., 1995, "3D Radiographic Reconstruction of Thoracic Facet Joints", *IEEE 17th Annual Conference IEEE Eng. Med. Bio. Soc.*, 1: 397–398.

* cited by examiner

FIG. 5

METHOD AND APPARATUS FOR COMPUTER MODELING A JOINT

CROSS-REFERENCE TO RELATED APPLICATION

The present invention is related to and claims priority to U.S. Provisional Patent Application Ser. No. 60/293,533, filed on May 29, 2001, entitled "Method and Apparatus for Computer Modeling a Joint," which is incorporated herein by reference.

COPYRIGHT NOTICE

A portion of the disclosure of the patent document contains material that is subject to copyright protection. The copyright owner has no objection to the facsimile reproduction by anyone of the patent document of the patent disclosure, as it appears in the Patent and Trademark Office patent file or records, but otherwise reserves all copyright rights whatsoever.

BACKGROUND OF THE INVENTION

The present invention relates generally to a computer model of a joint. More specifically, the present invention relates to a computer model of a joint to represent, for example, rheumatoid arthritis, osteoporosis, osteoarthritis or other inflammatory diseases of the joint.

Synovial inflammation, rapid degradation of cartilage, and erosion of bone in affected joints are characteristic of, for example, rheumatoid arthritis (RA). Recent evidence indicates that skeletal tissue degradation and inflammation are regulated through overlapping but not identical pathways in the rheumatoid joint and that therapeutic effects on these two aspects need not be correlated. Furthermore, considerable uncertainty exists about the relative contributions of the various biological processes of the joint to the pathogenesis of RA. Thus, a need exists for a better understanding of the mechanisms regulating joint inflammation and joint degradation. Such an understanding would be helpful for strategically designing therapies for protecting the joint.

Due to the complexity of the biological processes in the joint, mathematical and computer models can be used to help better understand the interactions between the various tissue compartments, cell types, mediators, and other factors involved in joint disease and healthy homeostasis. Several researchers have constructed simple models of the mechanical environment of the joint and compared the results to patterns of disease and development in cartilage and bone (Wynarsky & Greenwald, *J. Biomech.*, 16:241–251, 1983; Pollatschek & Nahir, *J. Theor. Biol.*, 143:497–505, 1990; Beaupre et al., *J. Rehabil Res. Dev.*, 37:145–151, 2000; Shi et al., *Acta Med. Okayama*, 17:646–653, 1999). However, these models are focused on the mechanical aspects of the joint and do not explicitly include the biological processes related to cells in the synovial membrane and other joint compartments. For instance, in RA the cells of the synovial membrane are known to play a major role in driving the disease (Szekanecz & Koch, *Curr. Rheumatol. Rep.*, 3:53–63, 2001). Hence, a need exists to develop a computer or mathematical model, which includes multiple compartments including the synovial membrane and the interactions of these compartments, to develop a better understanding of joint diseases.

SUMMARY OF THE INVENTION

Embodiments of the present invention relate to computer modeling of a joint. For example, one embodiment of the present invention relates to a computer model of a human joint afflicted with rheumatoid arthritis. The present invention also includes a method for developing an analytical model of an animal joint.

In one embodiment, the invention is a method for developing a computer model of an animal joint. The method comprises the steps of identifying data relating to a biological state of the joint; identifying biological processes related to the data, these identified biological processes defining at least one portion of the biological state of the joint; and combining the biological processes to form a simulation of the biological state of the joint. The biological state of the joint can be, for example, the state of a normal joint or a diseased joint. The joint diseases that can be modeled include rheumatoid arthritis, osteoporosis, reactive arthritis or osteoarthritis.

Another embodiment of the invention is a computer model of the biological state of an animal joint, comprising code to define the biological processes related to the biological state of the joint, and code to define the mathematical relationships related to interactions among biological variables associated with the biological processes. At least two of the biological processes are associated with the mathematical relationships. A combination of the code to define the biological processes and the code to define the mathematical relationships define a simulation of the biological state of the joint.

Yet another embodiment of the invention is a computer executable software code comprising of code to define biological processes related to a biological state of an animal joint including code to define mathematical relations associated with a first biological process from the biological processes and associated with interactions among biological variables associated with the first biological process, and code to define mathematical relations associated with a second biological process from the biological processes and associated with interactions among biological variables associated with the second biological process, the biological processes being associated with the biological state of the animal joint.

Another embodiment of the invention is a computer model of an animal joint, comprising a computer-readable memory storing codes and a processor coupled to the computer-readable memory, the processor configured to execute the codes. The memory comprises code to define biological processes related to the biological state of the joint, and code to define mathematical relationships related to interactions among biological variables associated with the biological processes. At least two biological processes from the biological processes are associated with the mathematical relationships. The combination of the code to define the biological processes and the code to define the mathematical relationships define a simulation of the biological state of the joint.

BRIEF DESCRIPTION OF THE DRAWINGS

FIG. 5 illustrates an example of display screen having chart windows and a browser window, according to an embodiment of the present invention.

DETAILED DESCRIPTION

Overview

Figure 1:
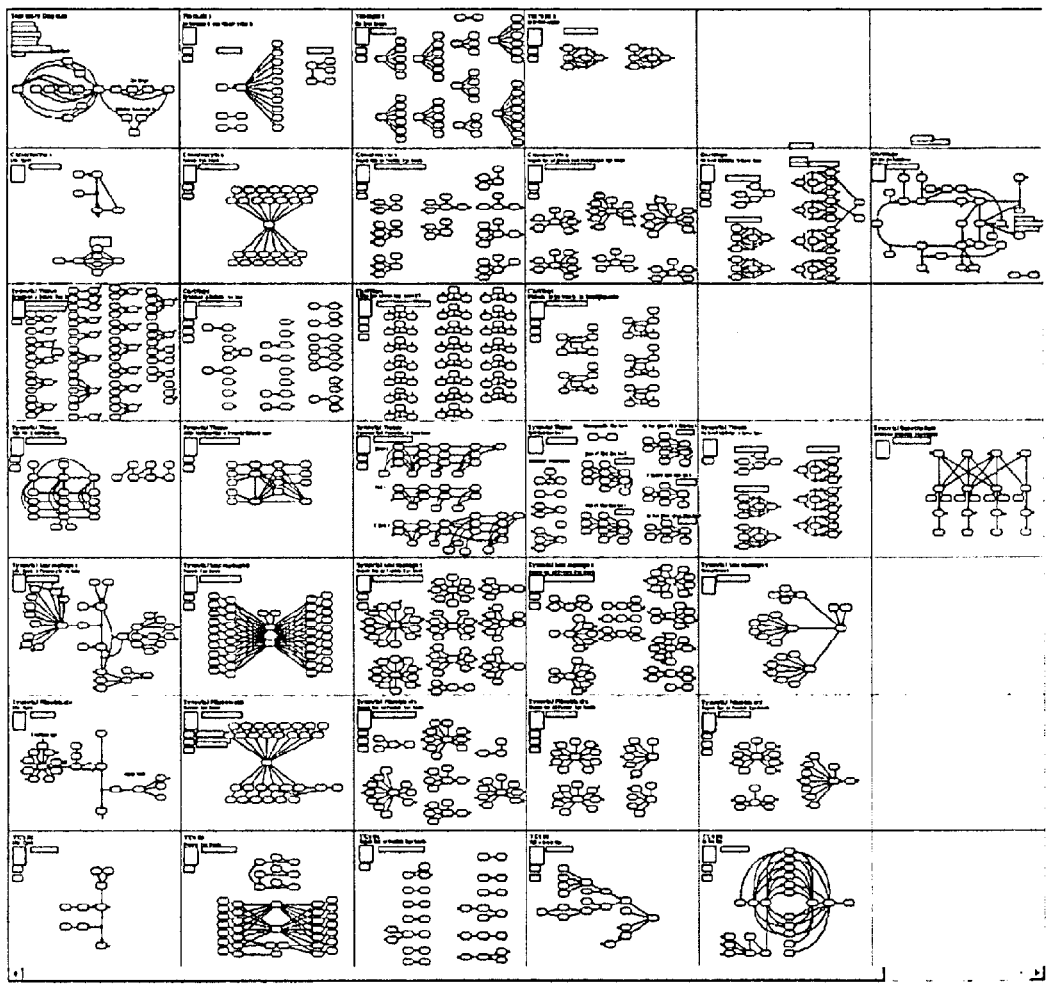
FIG. 1 illustrates an example of an Effect Diagram, which shows some of the modeled biological processes of the biological state of a joint affected with RA.

Embodiments of the present invention relate to computer modeling of an animal joint. The term "animal" as used herein includes humans. The term "joint" as used herein comprises the synovial tissue, synovial fluid, articular cartilage, bone tissues, and their cellular and extracellular composition, and the soluble mediators they contain. The computer model can represent the biological processes related to a joint. Typically, the model includes biological processes related to cartilage metabolism, tissue inflammation, and tissue hyperplasia in a non-diseased joint. Also, the computer model can include the representation of a diseased joint. For example, the computer model can represent a joint with rheumatoid arthritis, osteoporosis, osteoarthritis, or other inflammatory diseases of the joint. In addition, the model can represent joints affected with other arthritic conditions such as monoarticular, oligoarticular, or polyarticular arthritides of unknown etiology.

Embodiments of the present invention can relate to the computer modeling of rheumatoid arthritis (RA), such as for example, a knee joint afflicted with RA. The computer can also represent other joints, for example metacarpophalangeal and hip joints. The computer model can focus on the direct cytokine-mediated cellular interactions within the synovium and cartilage. Comparisons with clinical data can be used, for example, in fine-tuning the core components of the computer model.

In one embodiment, the computer model relates to, for example, diagnosed, established, early RA (synovial inflammation and hyperplasia, pannus formation, early stages of cartilage breakdown) in an adult patient with active progressive disease. This patient can be characterized by, for example, persistent synovial hyperplasia and inflammation as well as continuous degradation of the cartilage matrix. This disease state can be compared to healthy homeostasis where feasible and useful. Alternatively, other disease states and virtual patients can be represented in the model.

In one embodiment, the computer model can represent a single prototypical RA joint. The exact location of this prototypical joint need not be specified. An abstraction can be obtained that is compatible with available data and best reflects the overall disease process. The main compartments contained in the computer model can represent synovial tissue and cartilage at the cartilage-pannus junction of this prototypical RA joint.

In yet another embodiment, the computer model can be developed based on new patient types and can be based on both additions of new components and increased detail in components already modeled. For example, the computer model can incorporate biological features such as regulated recruitment of T cells, different T cell populations present in the tissue, or additional complexity in the mediator network. In another alternative embodiment, the computer model can involve the addition of new components, such as angiogenesis, bone metabolism, B cells or neutrophils.

In one aspect of the invention, the computer executable software code numerically solves the mathematical equations of the model under various simulated experimental conditions. Furthermore, the computer executable software code can facilitate visualization and manipulation of the model equations and their associated parameters to simulate different patients subject to a variety of stimuli. See, e.g., U.S. Pat. No. 6,078,739, entitled "Managing objects and parameter values associated with the objects within a simulation model," the disclosure of which is incorporated herein by reference. Thus, the computer model can be used to rapidly test hypotheses and investigate potential drug targets or therapeutic strategies.

Mathematical Model

The mathematical model of the computer-executable software code represents the dynamic biological processes related to the biological state of a joint. The form of the mathematical equations employed may include, for example partial differential equations, stochastic differential equations, differential algebraic equations, difference equations, cellular automata, coupled maps, equations of networks of Boolean or fuzzy logical networks, etc. In one embodiment, the mathematical equations used in the model are ordinary differential equations of the form:

$$dx/dt = f(x,p,t),$$

where x is an N dimensional vector whose elements represent the biological variables of the system (for example synovial macrophage number, tumor necrosis factor alpha concentration, and cartilage collagen II concentration), t is time, dx/dt is the rate of change of x, p is an M dimensional set of system parameters (for example baseline macrophage matrix metalloproteinase-1 (MMP-1) synthesis rate, T cell cycle time, catalytic constant for degradation of collagen II by MMP-1, and initial cartilage thickness), and f is a function that represents the complex interactions among biological variables.

The term "biological variables" refers to the extra-cellular or intra-cellular constituents that make up a biological process. For example, the biological variables can include metabolites, DNA, RNA, proteins, enzymes, hormones, cells, organs, tissues, portions of cells, tissues, or organs, subcellular organelles, chemically reactive molecules like $H^+$, superoxides, ATP, citric acid, protein albumin, as well as combinations or aggregate representations of these types of biological variables. In addition, biological variables can include therapeutic agents such as methotrexate, steroids, non-steroidal anti-inflammatory drugs, soluble TNF-alpha receptor, TNF-alpha antibody, and interleukin-1 receptor antagonists.

The term "biological process" is used herein to mean an interaction or series of interactions between biological variables. Thus, the above function f mathematically represents the biological processes in the model. Biological processes can include, for example, macrophage activation, regulation of macrophage protein synthesis, T cell proliferation, and collagen II degradation. The term "biological process" can also include a process comprising of one or more therapeutic agents, for example the process of binding a therapeutic agent to a cellular mediator. Each biological variable of the biological process can be influenced, for example, by at least one other biological variable in the biological process by some biological mechanism, which need not be specified or even understood.

The term "parameter" is used herein to mean a value that characterizes the interaction between two or more biological variables. Examples of parameters include affinity constants, baseline synthesis of a mediator, $EC_{50}$ value of stimulation of a first mediator by a second mediator, baseline macrophage matrix metalloproteinase-1 (MMP-1) synthesis rate, T cell cycle time, catalytic constant for degradation of collagen II by MMP-1, and initial cartilage thickness.

The term "biological state" is used herein to mean the result of the occurrence of a series of biological processes. As the biological processes change relative to each other, the biological state also undergoes changes. One measurement of a biological state, is the level of activity of biologic variables, parameters, and/or processes at a specified time and under specified experimental or environmental conditions.

In one embodiment the biological state can be mathematically defined by the values of x and p at a given time. Once a biological state of the model is mathematically specified, numerical integration of the above equation using a computer determines, for example, the time evolution of the biological variables x(t) and hence the evolution of the biological state over time.

The term "simulation" is used herein to mean the numerical or analytical integration of a mathematical model. For example, simulation can mean the numerical integration of the mathematical model of the biological state defined by the above equation, i.e., dx/dt=f( x, p, t).

A biological state can include, for example, the state of an individual cell, an organ, a tissue, and/or a multi-cellular organism. A biological state can also include the state of a mediator concentration in the plasma, interstitial fluid, intracellular fluid; e.g., the states of synovial inflammation and synovial hyperplasia are characterized by high concentrations of inflammatory mediators and large numbers of cells, respectively, in the synovium. These conditions can be imposed experimentally, or may be conditions present in a patient type. For example, a biological state of the cartilage can include the chondrocyte concentration for a patient with a certain age and disease duration. In another example, the biological states of the collection of synovial tissue mediators can include the state in which a patient with a certain disease undergoes a specific treatment.

The term "disease state" is used herein to mean a biological state where one or more biological processes are related to the cause or the clinical signs of the disease. For example, a disease state can be the state of a diseased cell, a diseased organ, a diseased tissue, or a diseased multi-cellular organism. Such diseases can include, for example, diabetes, asthma, obesity, and rheumatoid arthritis. A diseased multi-cellular organism can be, for example, an individual human patient, a specific group of human patients, or the general human population as a whole. A diseased state could also include, for example, a diseased protein or a diseased process, such as defects in matrix synthesis, matrix degradation, cell apoptosis, and cell signaling, which may occur in several different organs.

The term "biological attribute" is used herein to mean biological characteristics of a biological state, including a disease state. For example, biological attributes of a particular disease state include clinical signs and diagnostic criteria associated with the disease. The biological attributes of a biological state, including a disease state, can be measurements of biological variables, parameters, and/or processes. For example, for the disease state of rheumatoid arthritis, the biological attributes can include measurements of synovial hyperplasia, markers of inflammation, or cartilage thickness.

The term "reference pattern" is used herein to mean a set of biological attributes that are measured in a normal or diseased biological system. For example, the measurements may be performed on blood samples, on biopsy samples, or cell cultures derived from a normal or diseased human or animal. Examples of diseased biological systems include cellular or animal models of rheumatoid arthritis, including a human rheumatoid arthritis patient.

Computer System

Figure 7:
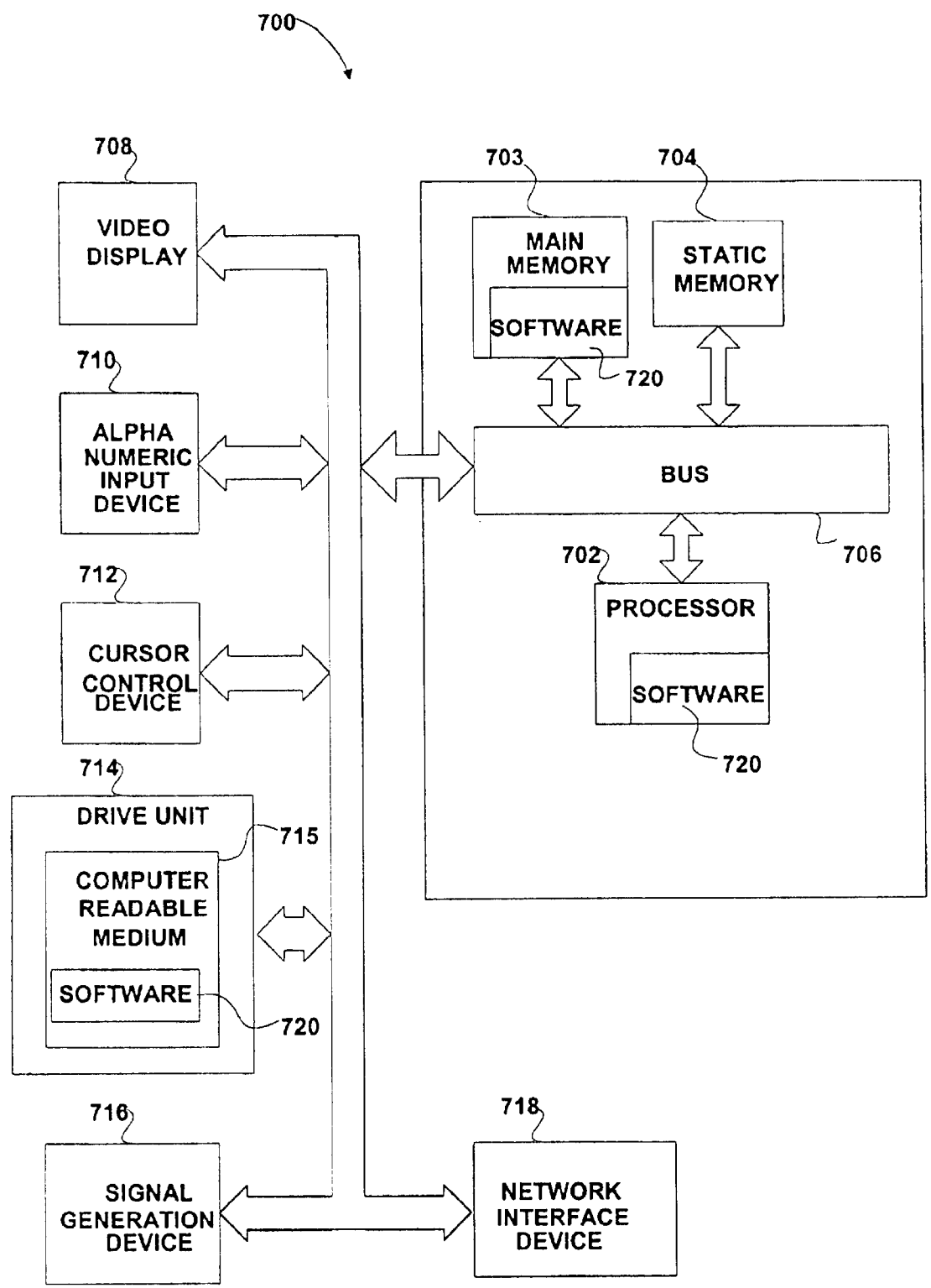
FIG. 7 is a schematic representation of a computer system within which software for performing the methods of the invention may reside or be executed.

FIG. 7 shows a system block diagram of a computer system within which the methods described above can operate via software code, according to an embodiment of the present invention. The computer system 700 includes a processor 702, a main memory 703 and a static memory 704, which are coupled by bus 706. The computer system 700 can further include a video display unit 708 (e.g., a liquid crystal display (LCD) or cathode ray tube (CRT)) on which a user interface can be displayed). The computer system 700 can also include an alpha-numeric input device 710 (e.g., a keyboard), a cursor control device 712 (e.g., a mouse), a disk drive unit 714, a signal generation device 716 (e.g., a speaker) and a network interface device medium 718. The disk drive unit 714 includes a computer-readable medium 715 on which software 720 can be stored. The software can also reside, completely or partially, within the main memory 703 and/or within the processor 702. The software 720 can also be transmitted or received via the network interface device 718.

The term "computer-readable medium" is used herein to include any medium which is capable of storing or encoding a sequence of instructions for performing the methods described herein and can include, but not limited to, optical and/or magnetic storage devices and/or disks, and carrier wave signals.

The Computer Model

The computer model can begin with a representation of a normal biological state, for example, as represented by the biological state of a single prototypical knee joint. A normal biological state is modeled through a series of user-interface screens that define the elements, including biological variables and biological processes, of the biological state being modeled. These elements of the biological state have dynamic relationships among themselves. An Effect Diagram can illustrate the dynamic relationships among the elements of the biological state and can include a Summary Diagram. This Summary Diagram can provide links to individual modules of the model; these modules, or functional areas, when grouped together, represent the large complex physiology of the biological state being modeled.

The modules model the relevant components of the biological state through the use of state and function nodes whose relations are defined through the use of diagrammatic arrow symbols. Thus, the complex and dynamic mathematical relationships for the various elements of the biological state are easily represented in a user-friendly manner. In this manner, a normal biological state can be represented.

Effect Diagram and Summary Diagram

FIG. 1 illustrates an example of an Effect Diagram, which shows some of the modeled biological processes of the biological state of a joint affected with RA. The Effect Diagram is organized into modules, or functional areas, which when grouped together represent the large complex physiology of the biological state being modeled.

The Effect Diagram includes a Summary Diagram in the upper left corner of the Effect Diagram. The Effect Diagram can include the Summary Diagram in the upper most left portion. In addition, the Effect Diagram can include the modules for the various biological processes of the biological state being modeled. From the Effect Diagram, a user can select any of these related user-interface screens by selecting such a screen from the Effect Diagram (e.g., by clicking a hyperlink to a related user-interface screen).

Figure 2:
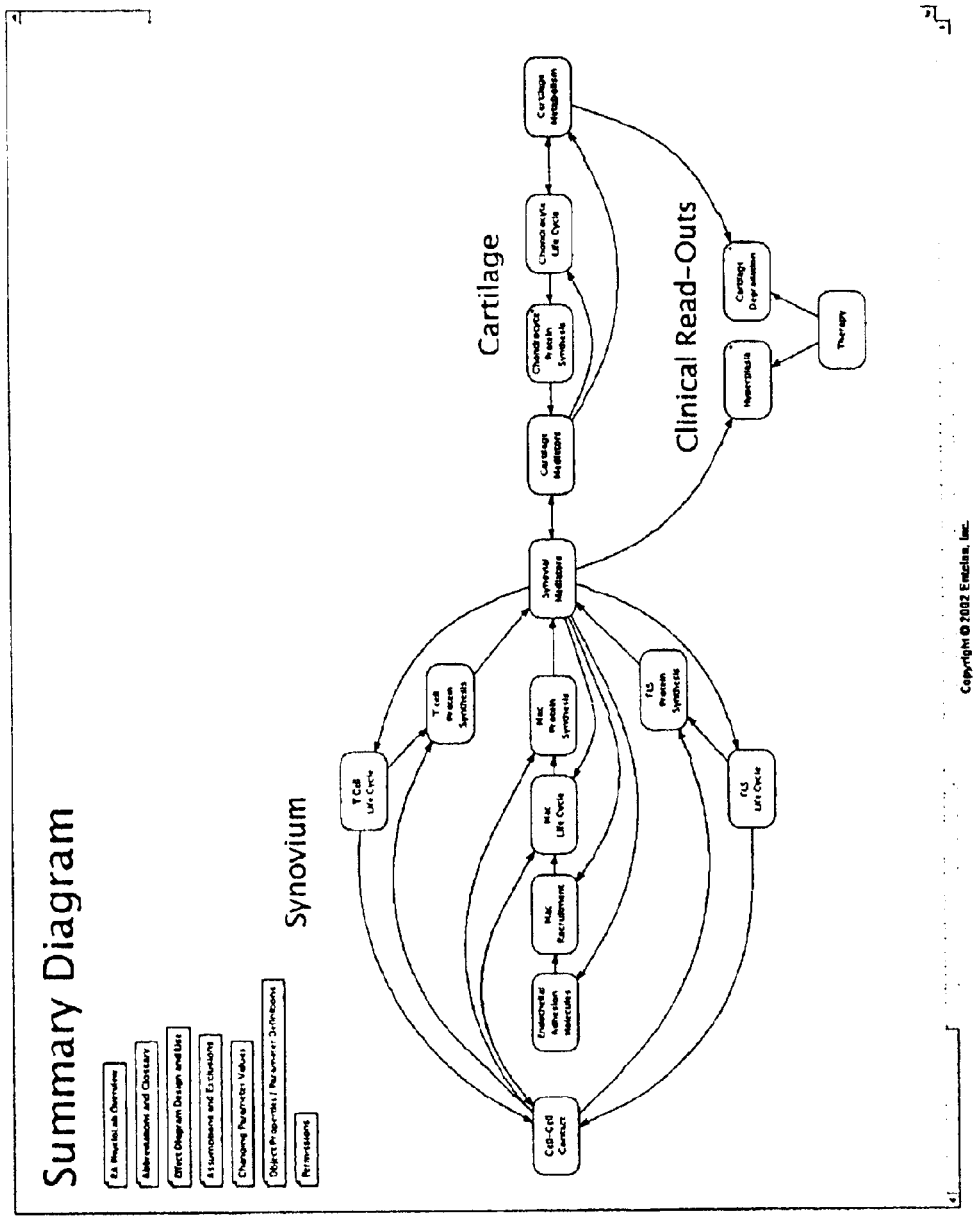
FIG. 2 illustrates an example of a Summary Diagram from the Effect Diagram of FIG. 1.

FIG. 2 illustrates an example of a Summary Diagram from the Effect Diagram of FIG. 1. As shown in FIG. 2, the Summary Diagram can provide an overview of the contents of the Effect Diagram and can contain nodes that link to modules in the Effect Diagram. These modules can be based on, for example, the anatomical elements of the biological state being modeled, such as chondrocytes, cytokines and other soluble factors and cartilage metabolism.

Figure 3:
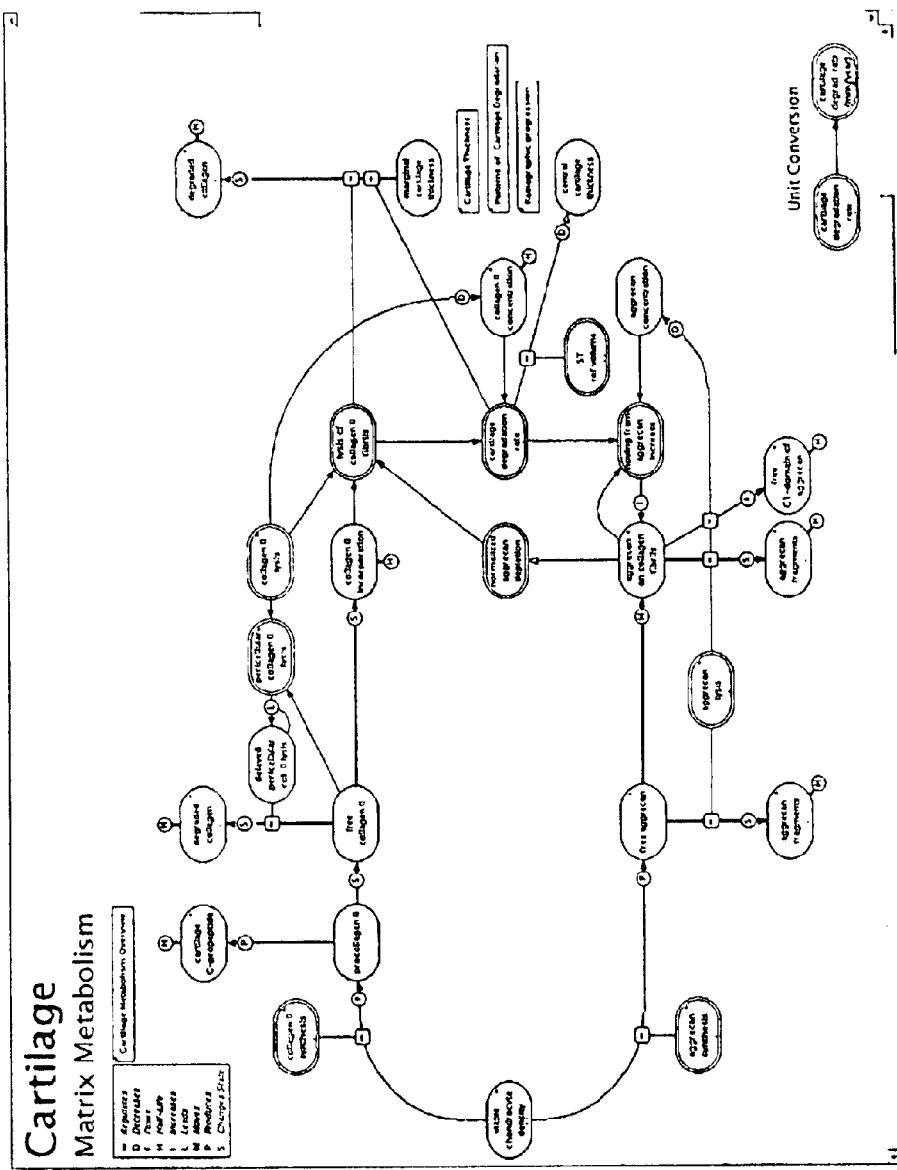
FIG. 3 illustrates an example of a module diagram for one of the anatomical elements shown in the Summary Diagram of FIG. 2.
Figure 4:
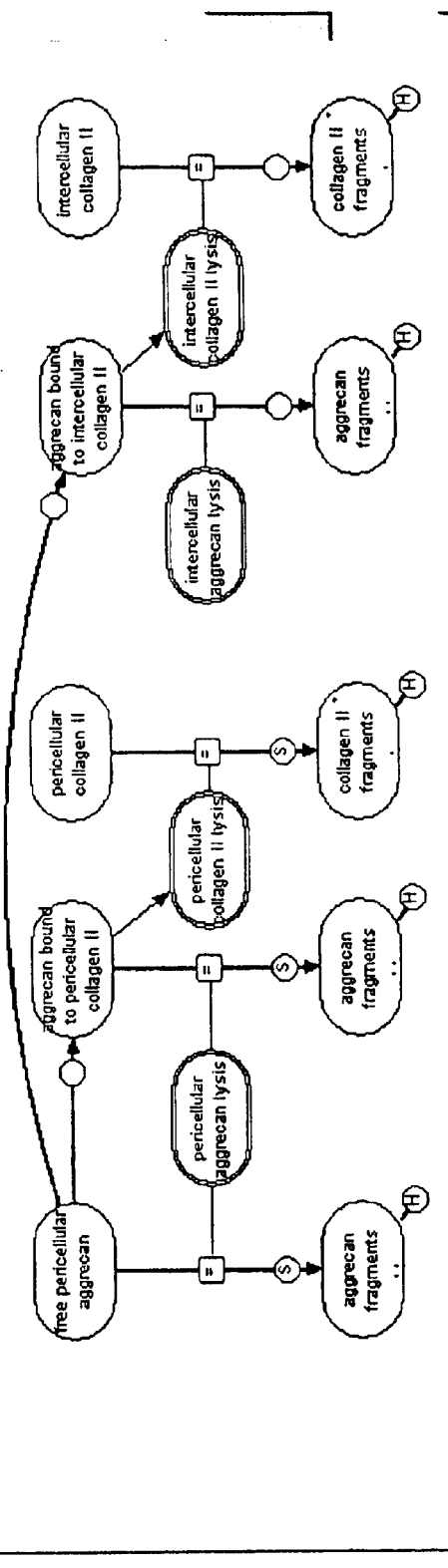
FIG. 4 illustrates an alternative for a portion of the module diagram shown in the FIG. 3.

FIG. 3 illustrates an example of a module diagram for one of the anatomical elements shown in the Summary Diagram of FIG. 2. More specifically, FIG. 3 illustrates a module diagram for the cartilage metabolism. FIG. 4 illustrates an alternative for a portion of the module diagram shown in the FIG. 3. FIGS. 11 through 45 list additional examples of user-interface screens for other modules for anatomical elements shown in the Summary Diagram of FIG. 2. FIGS 11 through 45 depict Appendix A depicts some of the modules of FIG. 1.

As FIG. 3 illustrates, the relevant biological variables and biological processes for the cartilage metabolism are represented through the use of state and function nodes whose relations are defined through the use of diagrammatic arrow symbols. Through the use of these state nodes, function nodes and arrows, the complex and dynamic mathematical relationships for the various elements of the physiologic system are easily represented in a user-friendly manner. In this manner, a biological state can be represented. The nodes and arrows are discussed below in the context of the mathematical relationship that underlie these diagrammatic representations.

Mathematical Equations Encoded in the Effect Diagram

As mentioned above, the Effect Diagram is a visual representation of the model equations. This section describes how the diagram encodes a set of ordinary differential equations. Note that although the discussion below regarding state and function nodes refers to biological variables for consistency, the discussion also relates to variables of any appropriate type and need not be limited to just biological variables.

State and Function Nodes

State and function nodes show the names of the variables they represent and their location in the model. Their arrows and modifiers show their relation to other nodes within the model. State and function nodes also contain the parameters and equations that are used to compute the values or their variables in simulated experiments. In one embodiment of the computer model, the state and function nodes are represented according to the method described in U.S. Pat. No. 6,051,029 and co-pending U.S. application Ser. No. 09/588,855, both of which are entitled "Method of generating a display for a dynamic simulation model utilizing node and link representations," and both of which are incorporated herein by reference. Further examples of state and function nodes are further discussed below.

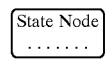

State nodes, the single-border ovals in the Effect Diagram, represent variables in the system the values of which are determined by the cumulative effects of its inputs over time.

State node values are defined by differential equations. The predefined parameters for a state node include its initial value ($S_o$) and its status. State nodes that have a half-life have the additional parameter of a half-life (h) and are labeled with a half-life ⌛ symbol.

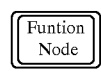

Function nodes, the double-border ovals in the Effect Diagram, represent variables in the system the values of which, at any point in time are determined by inputs at the same point in time.

Function nodes are defined by algebraic functions of their inputs. The predefined parameters for a function node include its initial value ($F_o$) and its status.

Setting the status of a node effects how the value of the node is determined. The status of a state or function node can be Computed—the value is calculated as a result of its inputs Specified-Locked—the value is held constant over time Specified Data—the value varies with time according to predefined data points.

State and function nodes can appear more than once in the Effect Diagram as alias nodes. Alias nodes are indicated by one or more dots, as in the state node illustration above. All nodes are also defined by their position, with respect to arrows and other nodes, as being either source nodes (S) or target nodes (T). Source nodes are located at the tails of arrows, and target nodes are located at the heads of arrows. Nodes can be active or inactive. Active nodes are white. Inactive nodes match the background color of the Effect Diagram.

State Node Equations

The computational status of a state node can be Computed, Specified-Locked, or Specified Data.

State Node Computed $$\frac{dS}{dt} = \begin{cases} \text{sum of } arrowterms & \text{when } h = 0 \\ \frac{\ln 1/2}{h} S(t) + \text{sumof } arrowterms & \text{when } h > 0 \end{cases}$$

Where S is the node value, t is time, S(t) is the node value at time, t, and h is the half-life. The three dots at the end of the equation indicate there are additional terms in the equation resulting from any effect arrows leading into it and by any conversion arrows that lead out of it. If h is equal to 0, then the half-life calculation is not performed and dS/dt is determined solely by the arrows attached to the node.

| | |
|---|---|
| State Node Specified-Locked | $S(t) = S_0$ for all t |
| State Node Specified Data | $S(t)$ is defined by specified data entered for the state node. |

State node values can be limited to a minimum value of zero and a maximum value of one. If limited at zero, S can never be less than zero and the value for S is reset to zero if it goes negative. If limited at one, S cannot be greater than one and is reset to one if it exceeds one.

Function Node Equations

Function node equations are computed by evaluating the specified function of the values of the nodes with arrows pointing into the function node (arguments), plus any object and Effect Diagram parameters used in the function expression. To view the specified function, click the Evaluation tab in the function node Object window.

The Effect Diagram—Arrows

Arrows link source nodes to target nodes and represent the mathematical relationship between the nodes. Arrows can be labeled with circles that indicate the activity of the arrow. A key to the annotations in the circles is located in the upper left corner of each module in the Effect Diagram. If an arrowhead is solid, the effect is positive. If the arrowhead is hollow, the effect is negative.

Arrow Types

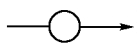 Effect arrows, the thin arrows on the Effect Diagram, link source state or function nodes to target state nodes. Effect arrows cause changes to target nodes but have no effect on source nodes. They are labled with circles that indicate the activity of the arrow.

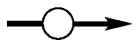 Conversion arrows, the thick arrows on the Effect Diagram, represent the way the contents of state nodes are converted into the contents of the attached state nodes. They are labeled with circles that indicate the activity of the arrow. The activity may effect the source node or the target node or both nodes. The conversion can go either way.

 Argument arrows specify which nodes are input arguments for function nodes. They do not contain parameters or equations and are not labeled with activity circles.

Arrow Characteristics

Effect or conversion arrows can be constant, proportional, or interactive.

 Arrows that are constant have a break in the arrow shaft. They are used when the rate of change of the target is independent of the values of the source and target nodes.

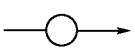 Arrows that are proportional have solid, unbroken shafts and are used when the rate of change is dependent on, or is a function of, the values of the source node.

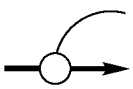 Arrows that are interactive have a loop from the activity circle to the target node. They indicate that the rate of change of the target is dependent on, or a function of, the value of both the source node and the target node.

Arrow Properties can be displayed in an Object window (not shown). The window may also include tabs for displaying Notes and Arguments associated with the arrow. If Notes are available in the Object window, the arrow is labeled with a red dot (·).

Arrow Equations: Effect Arrows

Proportional Effect Arrow: The rate of change of target tracks source node value.

$$\frac{dT}{dt} = C \cdot (S(t))^a + \ldots$$

Where T is the target node, C is a coefficient, S is the source node, and a is an exponent.

Constant Effect Arrow: The rate of change of the target is constant.

$$\frac{dT}{dt} = K + \ldots$$

Where T is the target node and K is a constant.

Interaction Effect Arrow: The rate of change of the target depends on both the source node and target node values.

$$\frac{dT}{dt} = C((S(t))^a - (T(t))^b) + \ldots$$

Where T is the target node, S is the source node, and a and b are exponents. This equation can vary depending on the operation selected in the Object window. The operations available are S+T, S−T, S*T, T/S, and S/T.

Arrow Equations: Conversion Arrows

Proportional Conversion Arrow: The rate of change of the target tracks the value of source node.

$$\frac{dT}{dt} = C \cdot R \cdot (S(t))^a + \ldots$$

$$\frac{dS}{dt} = -C \cdot (S(t))^a + \ldots$$

Where T is the target node, S is the source node, C is a coefficient, R is a conversion ratio, and a is an exponent.

Constant Conversion Arrow: The rates of change of target and source are constant such that an increase in target corresponds to a decrease in source.

$$\frac{dT}{dt} = K \cdot R + \ldots$$

$$\frac{dS}{dt} = -K + \ldots$$

Where T is the target node, S is the source node, K is a constant, and R is a conversion ratio.

Interaction Conversion Arrow: The rates of change of the target and source depend on both source and target node values such that an increase in target corresponds to a decrease in source.

$$\frac{dT}{dt} = R \cdot C((S(t))^a - (T(t))^\delta) + \ldots$$

$$\frac{dS}{dt} = -C((S(t))^a - (T(t))^\delta) + \ldots$$

Where T is the target node, S is the source node, a and b are exponents, and R is a conversion ratio. This equation can vary depending on the operation selected in the Object window. The operations available are S+T, S−T, S*T, T/S, and S/T.

The Effect Diagram—Modifiers

Modifiers indicate the effects nodes have on the arrows to which they are connected. The type of modification is qualitatively indicated by a symbol in the box. For example, a node can allow Ⓐ, block Ⓑ, regulate Ⓡ, inhibit Ⓘ, or stimulate Ⓢ an arrow rate.

A key to the modifier annotations is located in the upper left corner of each module.

Modifier Properties can be displayed in the Object Window. The window may also include tabs for displaying the notes, arguments, and specified data associated with the modifier. If notes are available in the Object window, the modifier is labeled with a red dot (·).

$$\frac{dT}{dt} = M \cdot f\left(\frac{u}{N}\right) \cdot arrowterm + \ldots$$

Effect Arrow, Modifier Equation:

Where T is the target node, M is a multiplier constant, N is a normalization constant, $f(\ )$ is a function (either linear or specified by a transform curve), and arrow term is an equation fragment from the attached arrow.

Modifier Effect

By default, conversion arrow modifiers affect both the source and target arrow terms. However, in some cases, a unilateral, modifier is used. Such modifier will affect either a source arrow term or on target arrow term; it does not affect both arrow terms.

Conversion arrow, Source Only Modifier Equation:

$$\frac{dS}{dt} = M \cdot f\left(\frac{u}{N}\right) \cdot arrowterm + \text{other attached arrow terms}$$

Conversion arrow, Target Only Modifier Equation:

$$\frac{dT}{dt} = M \cdot f\left(\frac{u}{N}\right) \cdot arrowterm + \text{other attached } arrowterms$$

The equation for a source and target modifier uses both the Source Only equation and the Target Only equation.

When multiplicative and additive modifiers are combined, effect is given precedence. For example, if the following modifiers are on an arrow, a1,a2: Additive, Source and Target m1,m2: Multiplicative, Source and Target A1,A2: Additive, Target Only M1,M2: Multiplicative, Target Only then the rates are modified by Target node: (a1+a2+A1+A2)*(m1*m2)*(M1*M2)

Source node: (a1+a2)*(m1*m2)

Embodiments of the Invention

Figure 9:
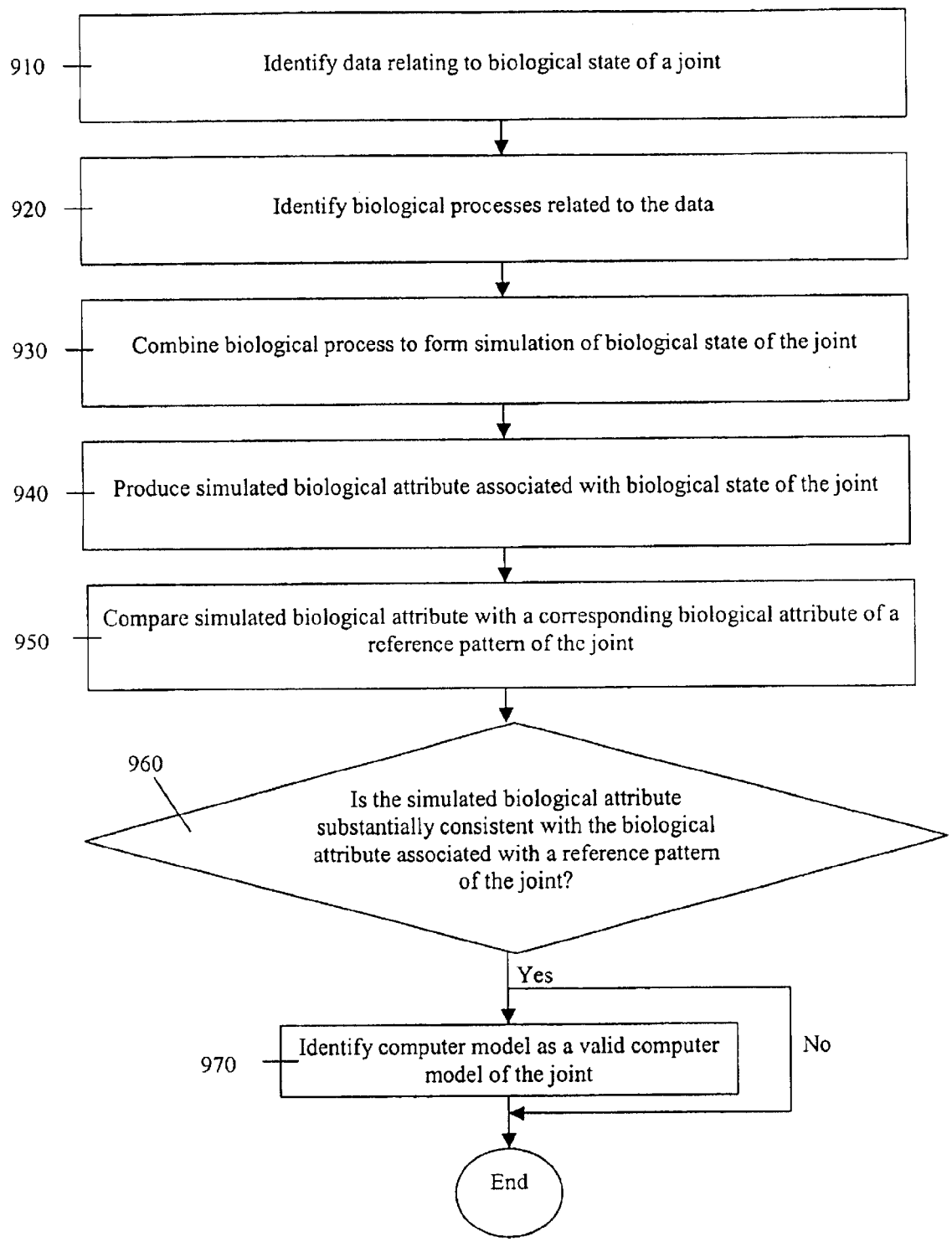
FIG. 9 depicts a flowchart for a method for developing a computer model of an animal joint according to one embodiment of the invention.

FIG. 9 depicts a flowchart for a method for developing a computer model of an animal joint according to one embodiment of the invention. At step 910, data relating to a biological state of the joint is identified. At step 920, biological processes related to the data are identified. These biological processes define at least one portion of the biological state of the joint. At step 930, the biological processes are combined to form a simulation of the biological state of the joint.

The method for developing a computer model of an animal joint can further comprise the optional steps of 940, 950, 960, and 970 for validating the computer model, as depicted in FIG. 9. In the validation process, at step 940 a simulated biological attribute associated with the biological state of the joint is produced. At step 950, the simulated biological attribute is compared with a corresponding biological attribute in a reference pattern of the joint. At steps 960 and 970, the validity of the computer model is identified. At step 960, it is determined whether the simulated biological attribute is substantially consistent with the biological attribute associated with the reference pattern of the joint. At step 970, if the simulated biological attribute is substantially consistent with the biological attribute associated with the reference pattern of the joint the computer model is identified as a valid computer model of an animal joint.

Figure 10:
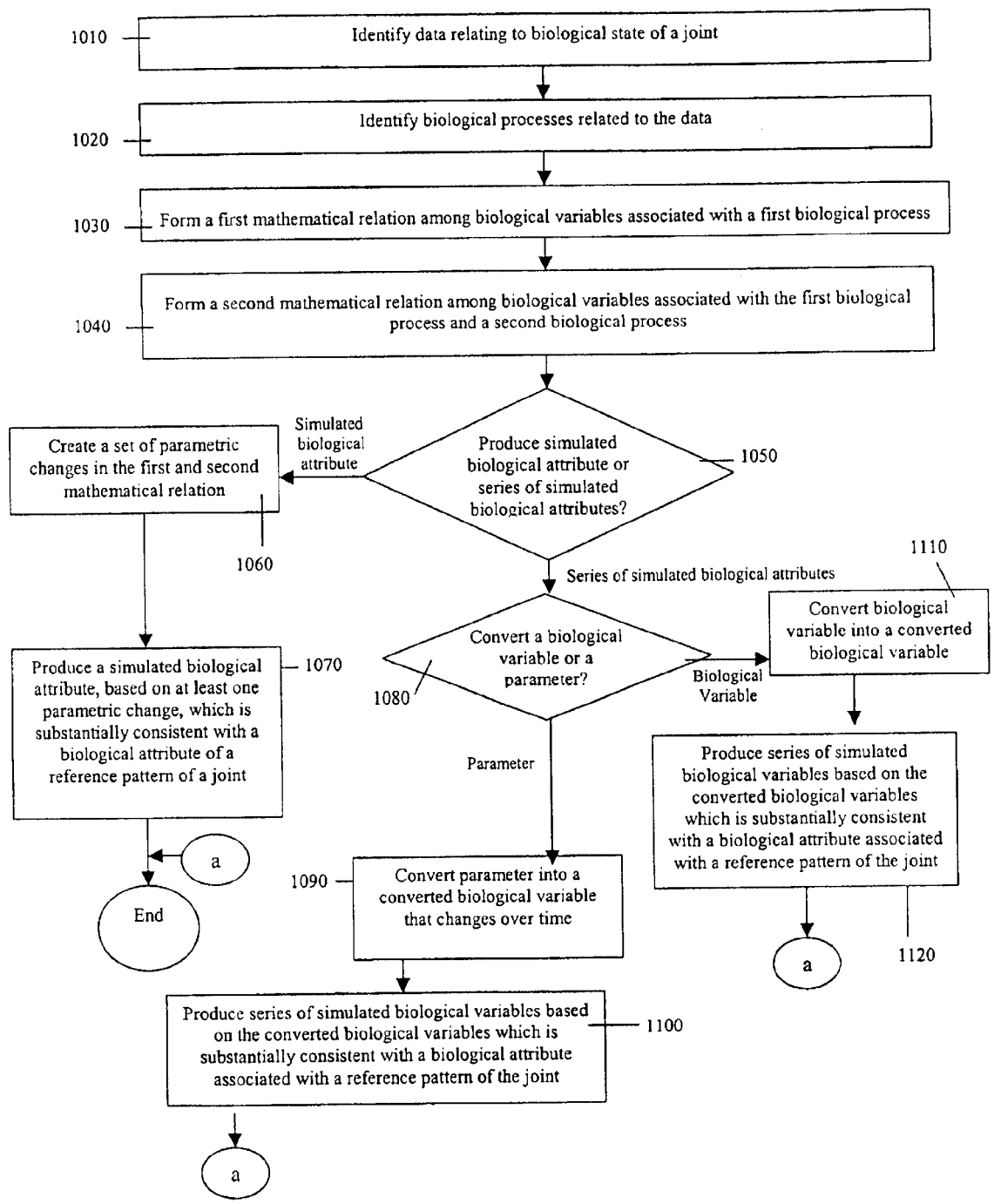
FIG. 10 depicts a flowchart for a method for developing a computer model of a joint according to another embodiment of the invention.
Figure 11:
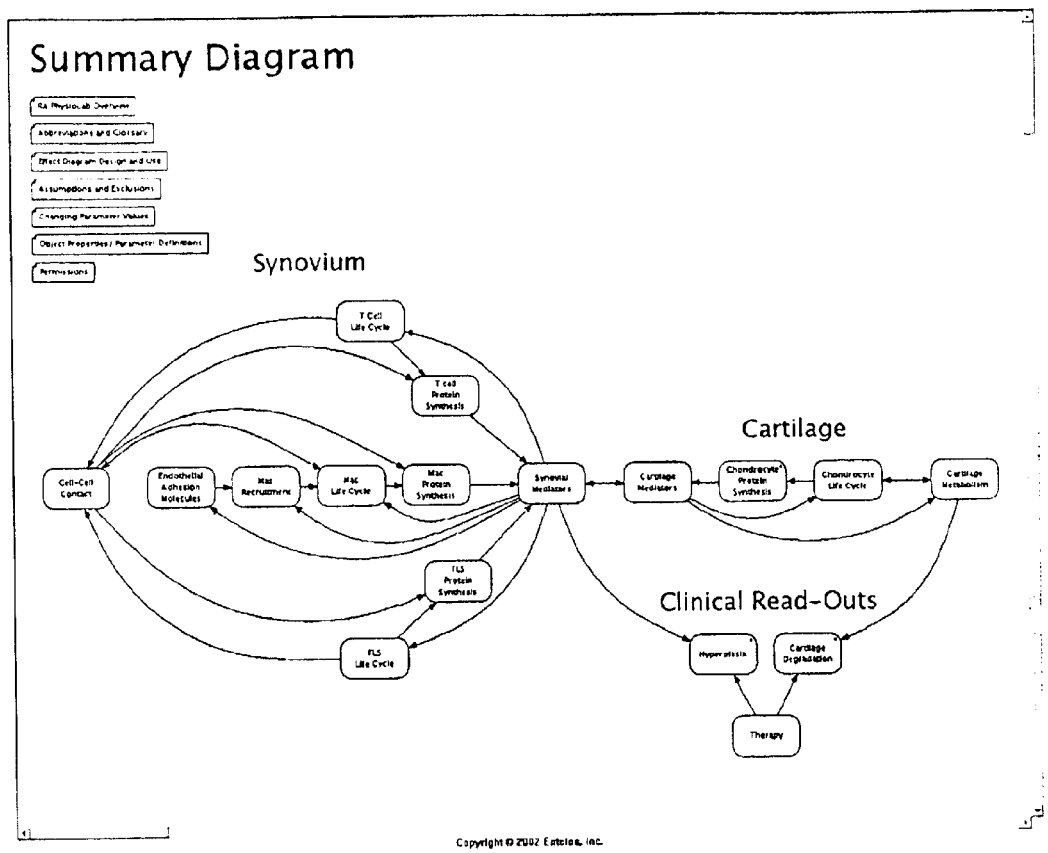
FIGS. 11–45 show additional examples of user-interface screens for other modules for anatomical elements shown in the Summary Diagram of FIG. 2.
Figure 12:
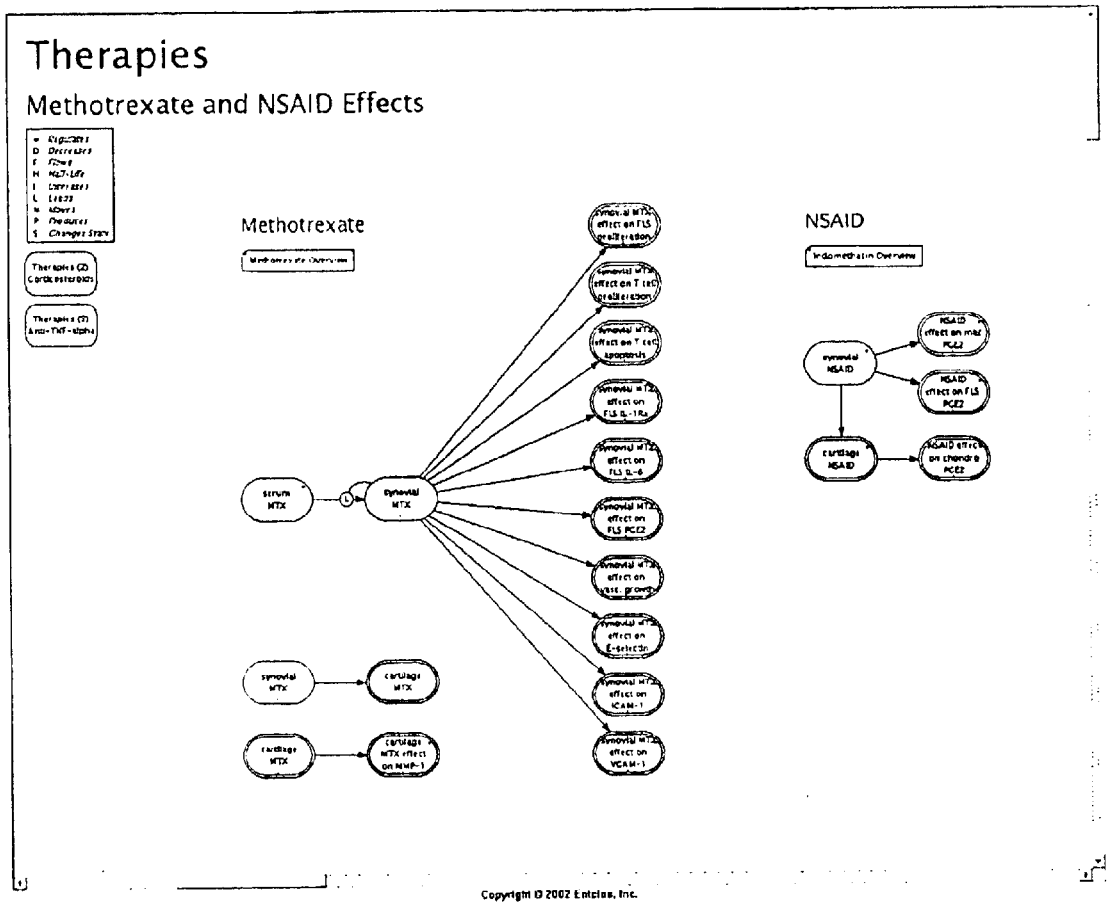
Figure 13:
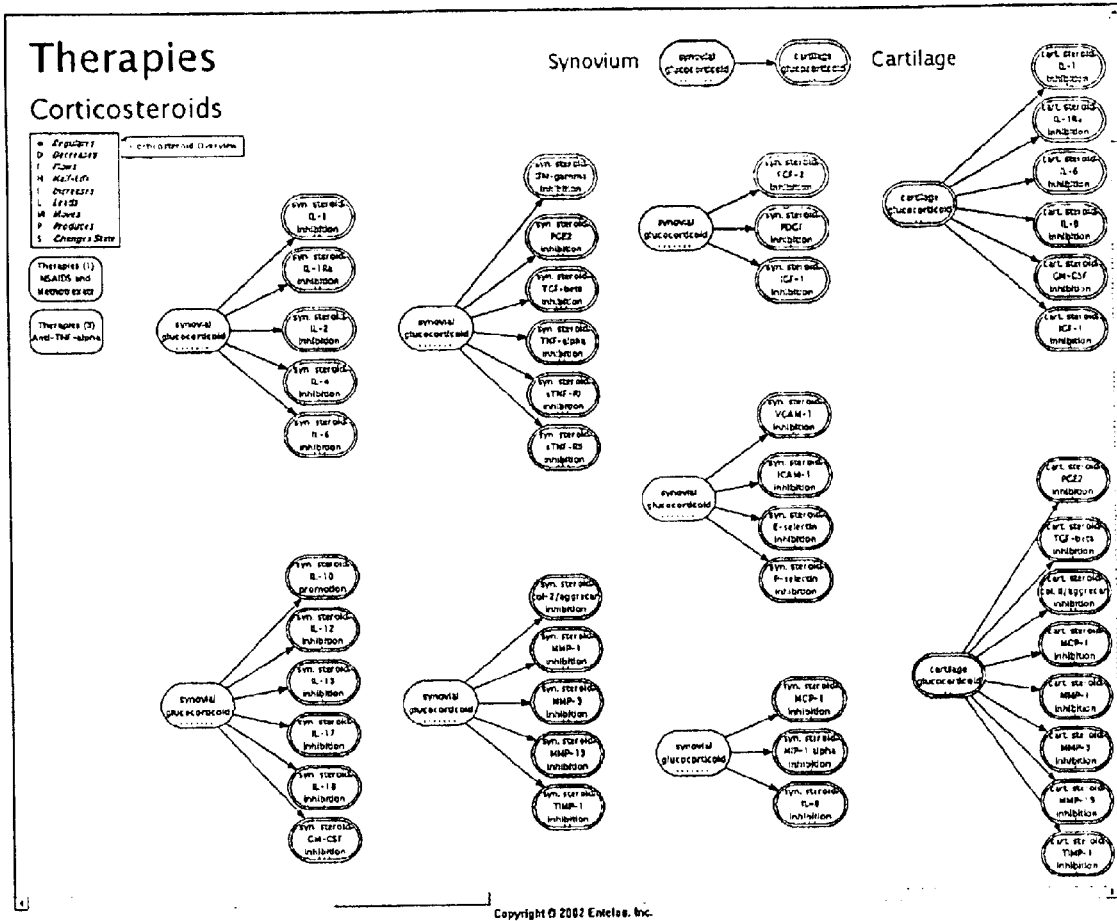
Figure 14:
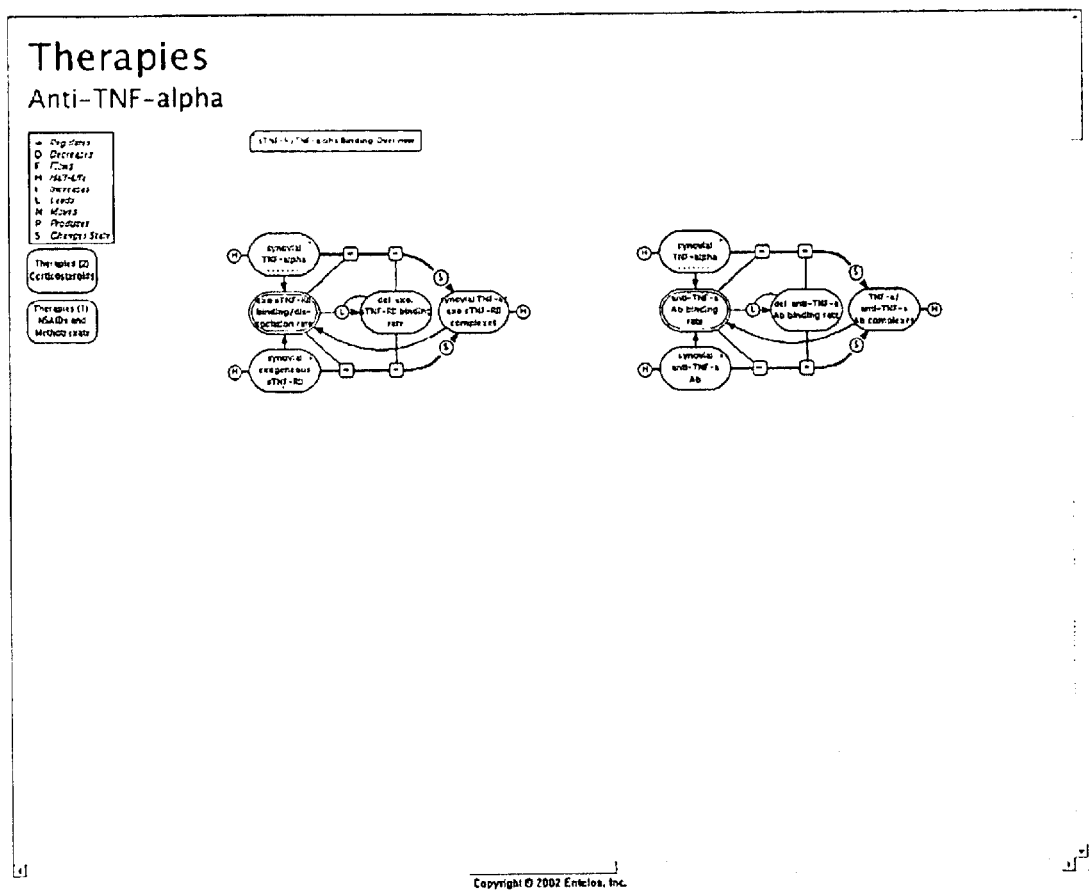
Figure 15:
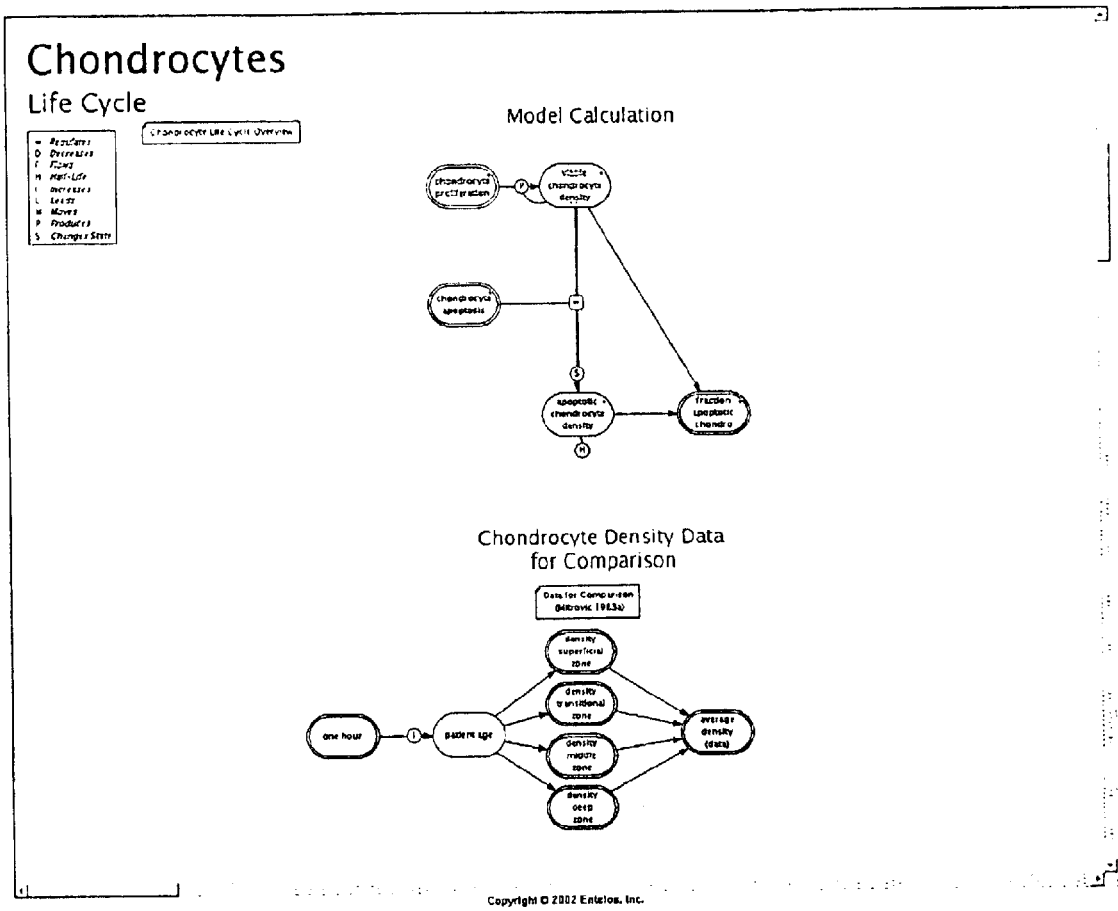
Figure 16:
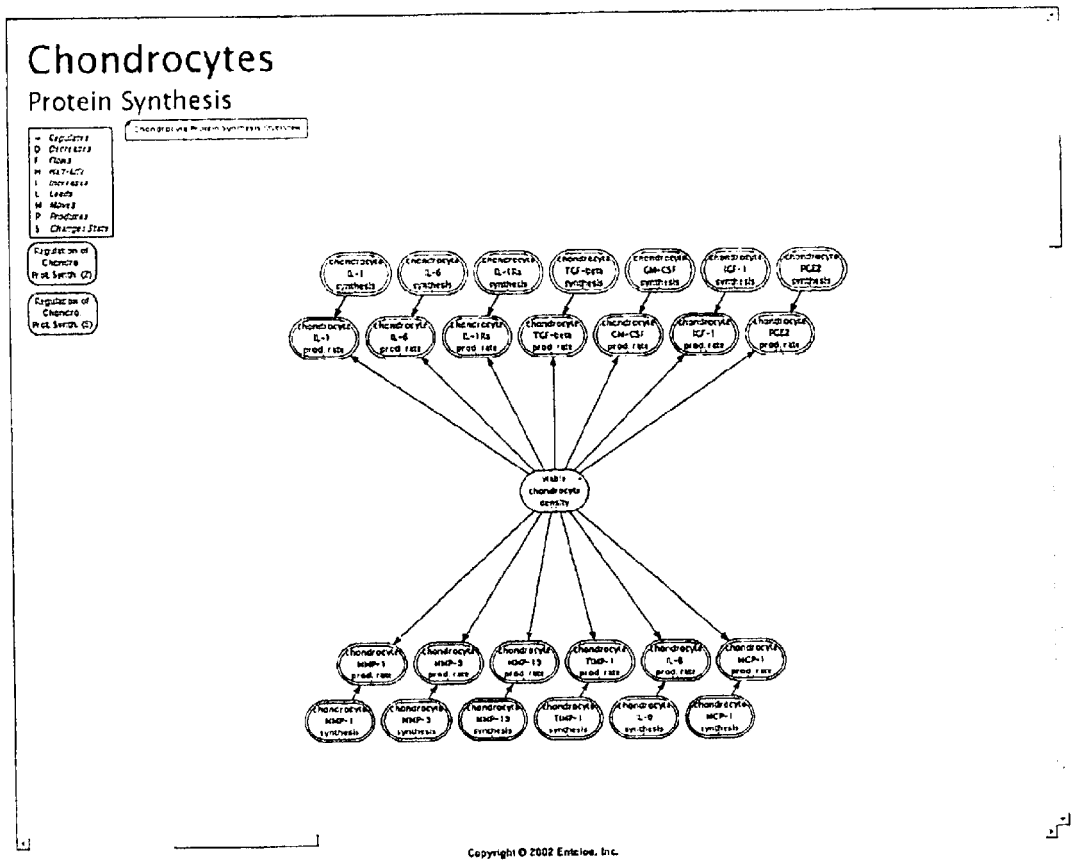
Figure 17:
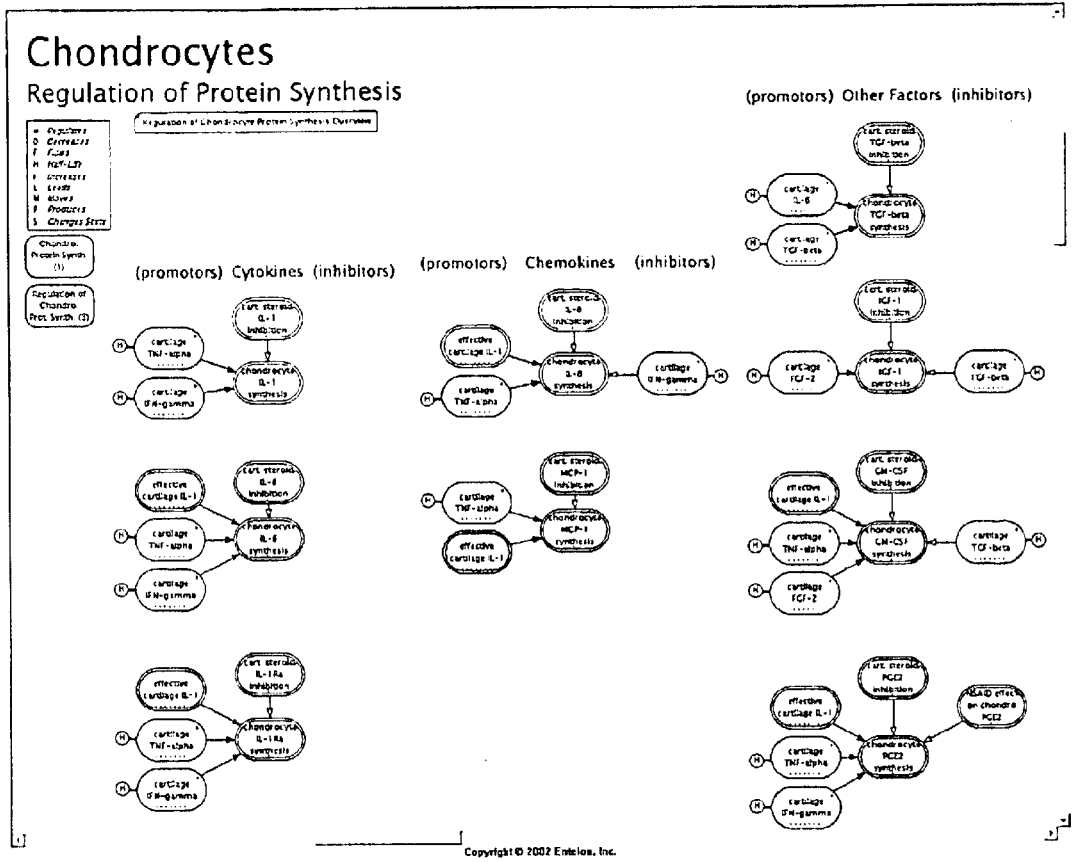
Figure 18:
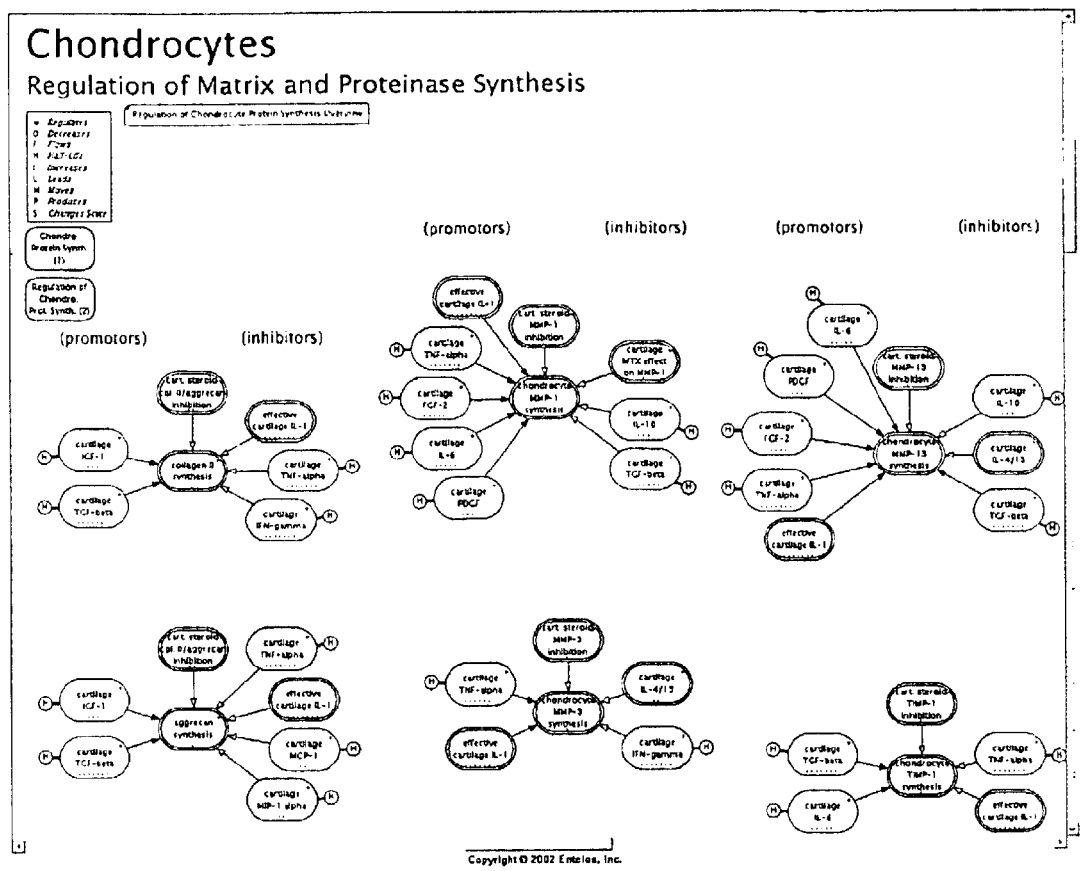
Figure 19:
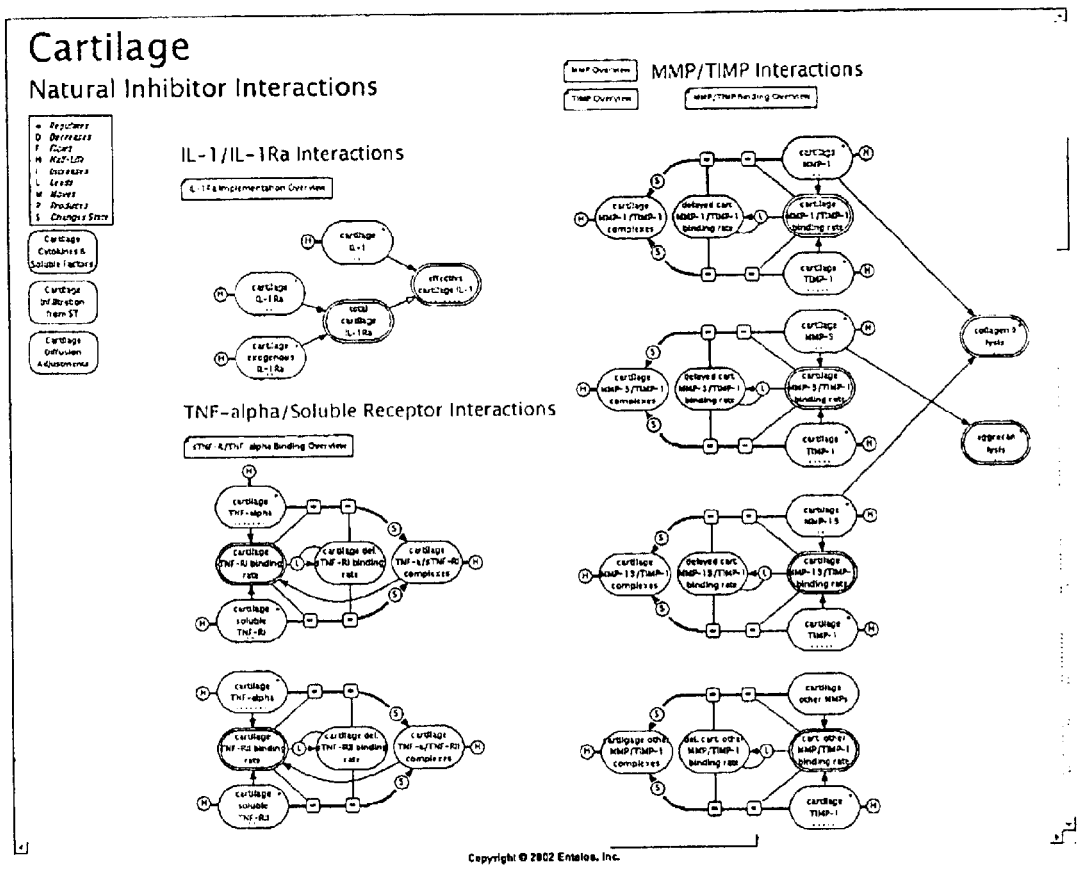
Figure 20:
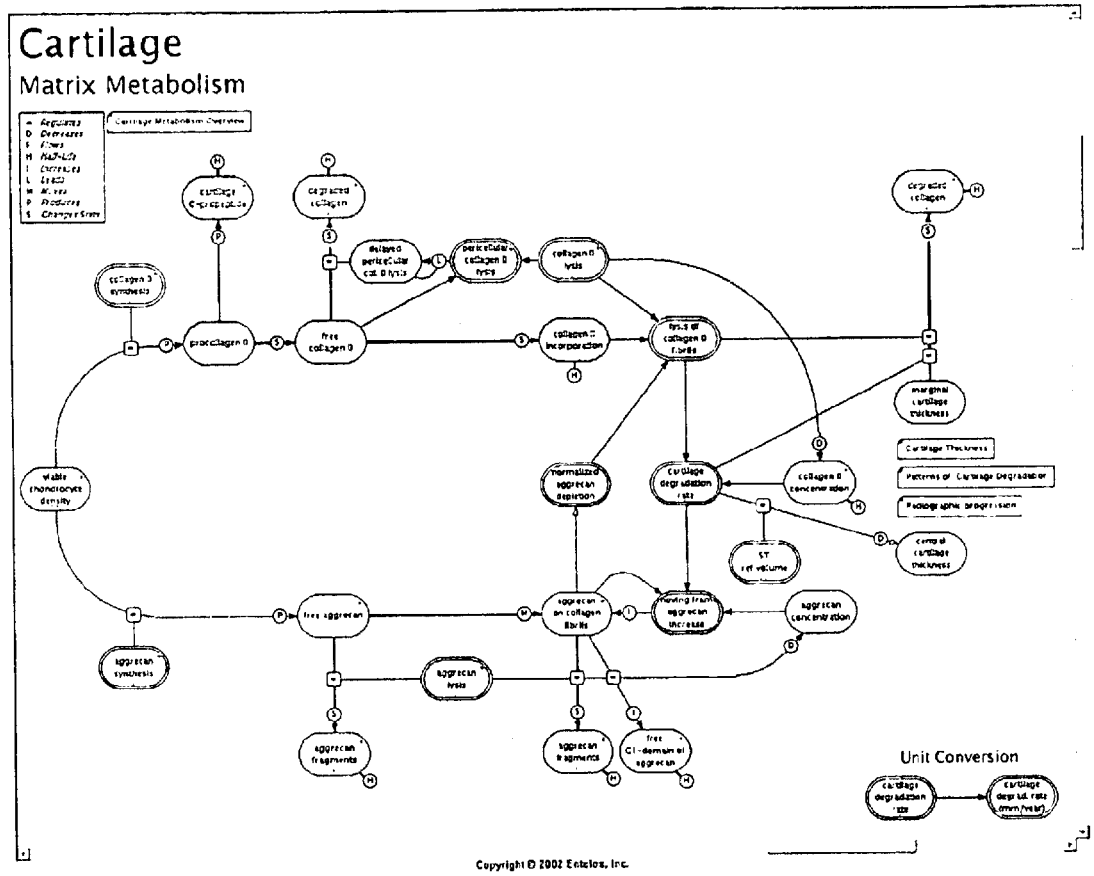
Figure 21:
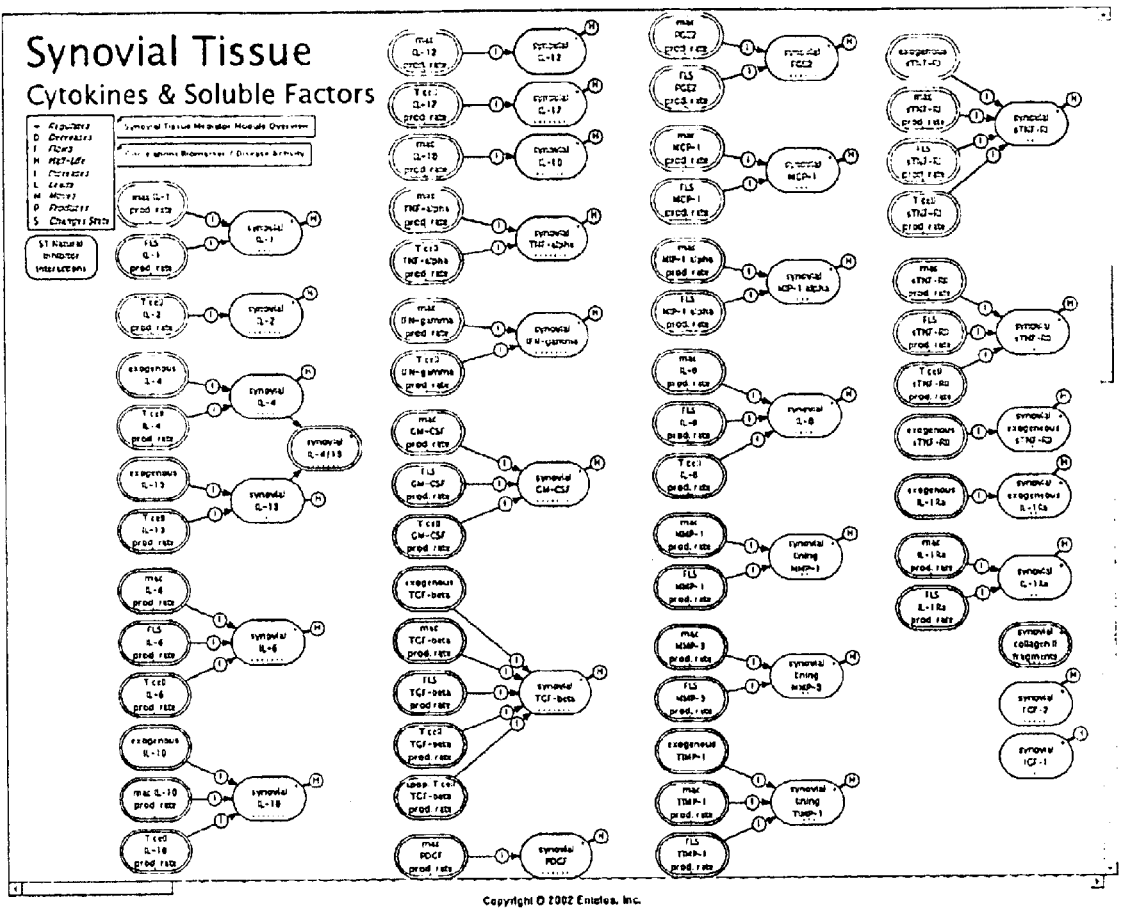
Figure 22:
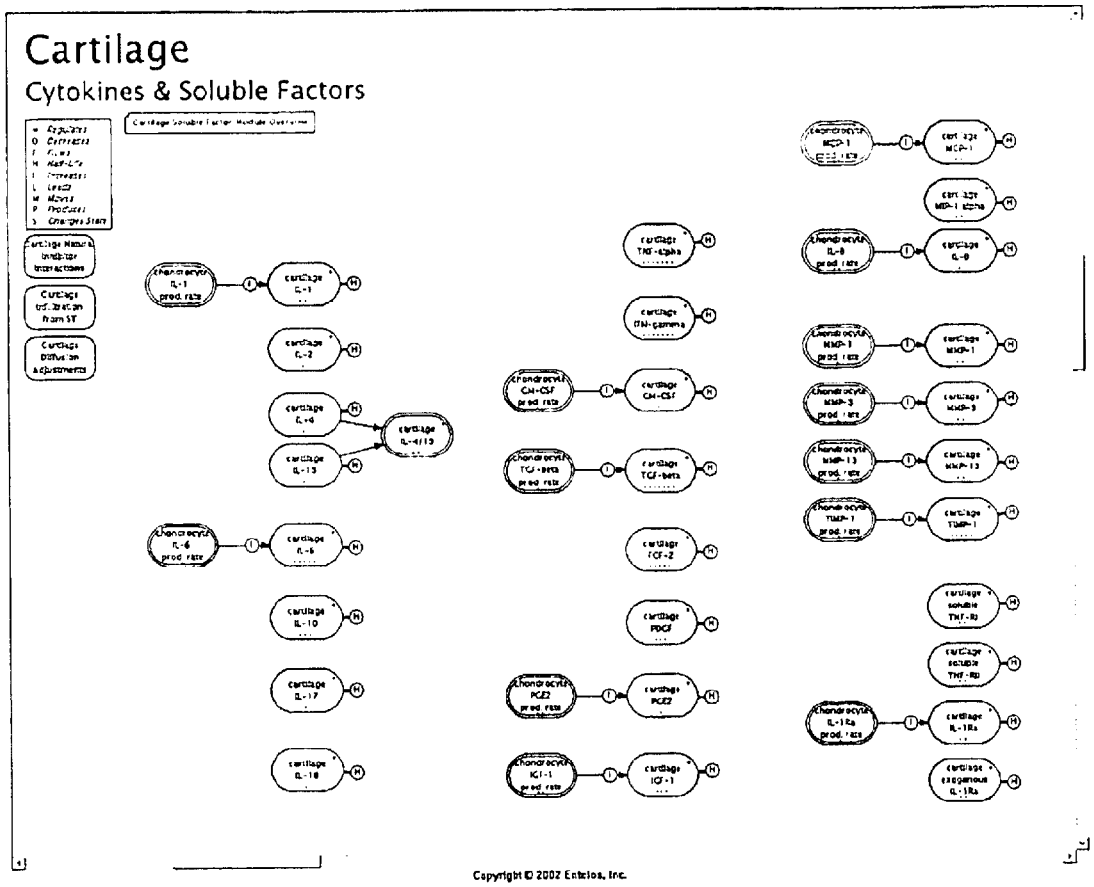
Figure 23:
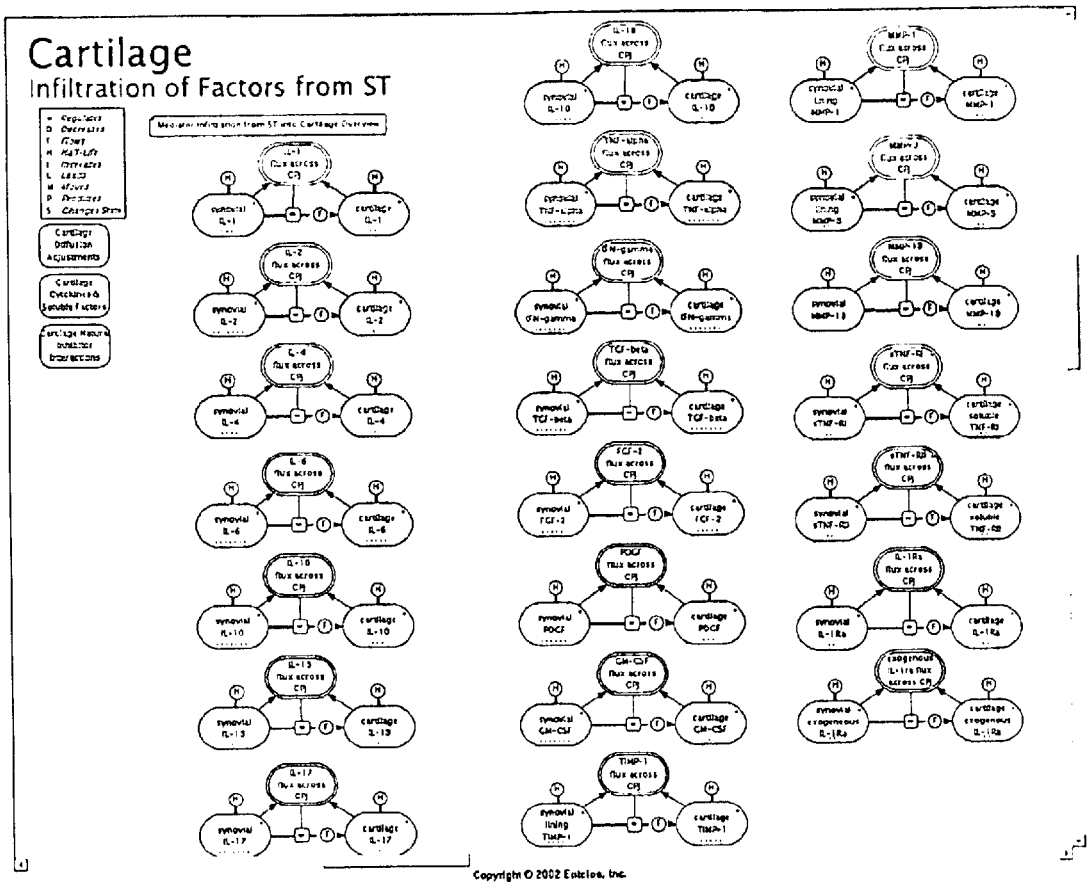
Figure 24:
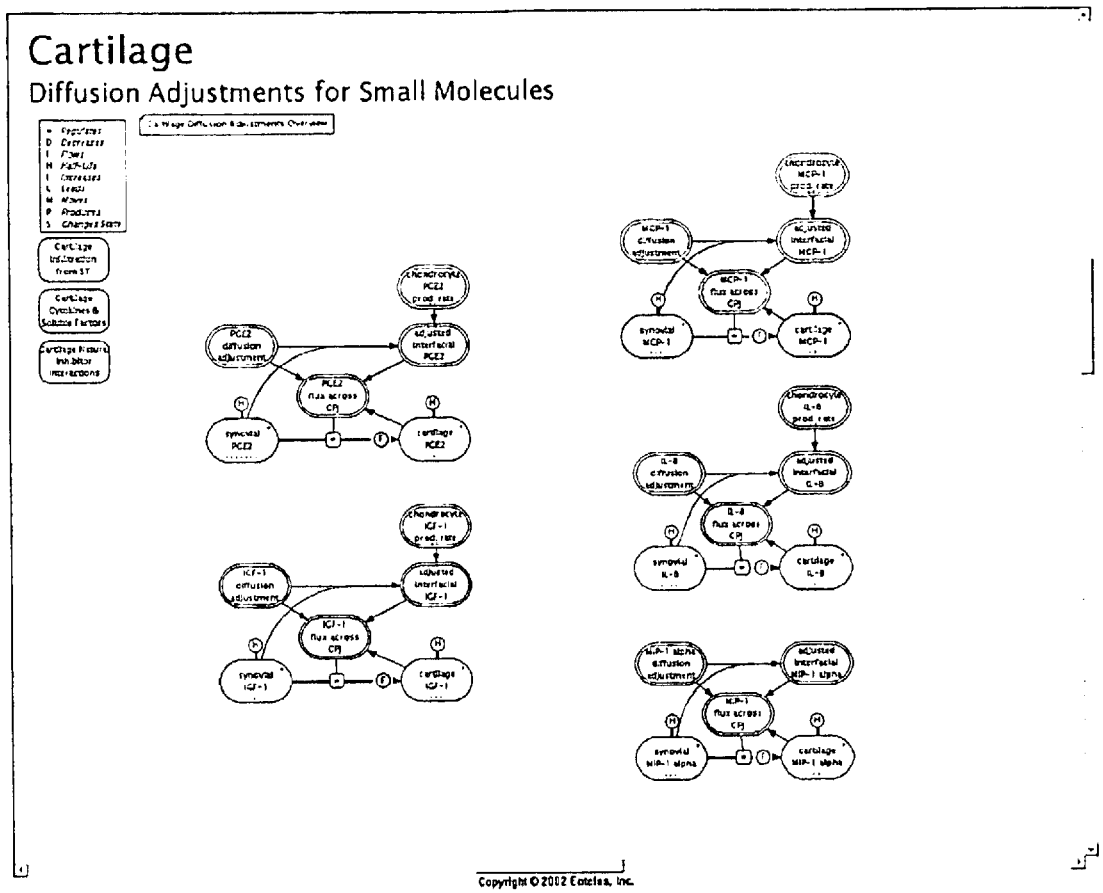
Figure 25:
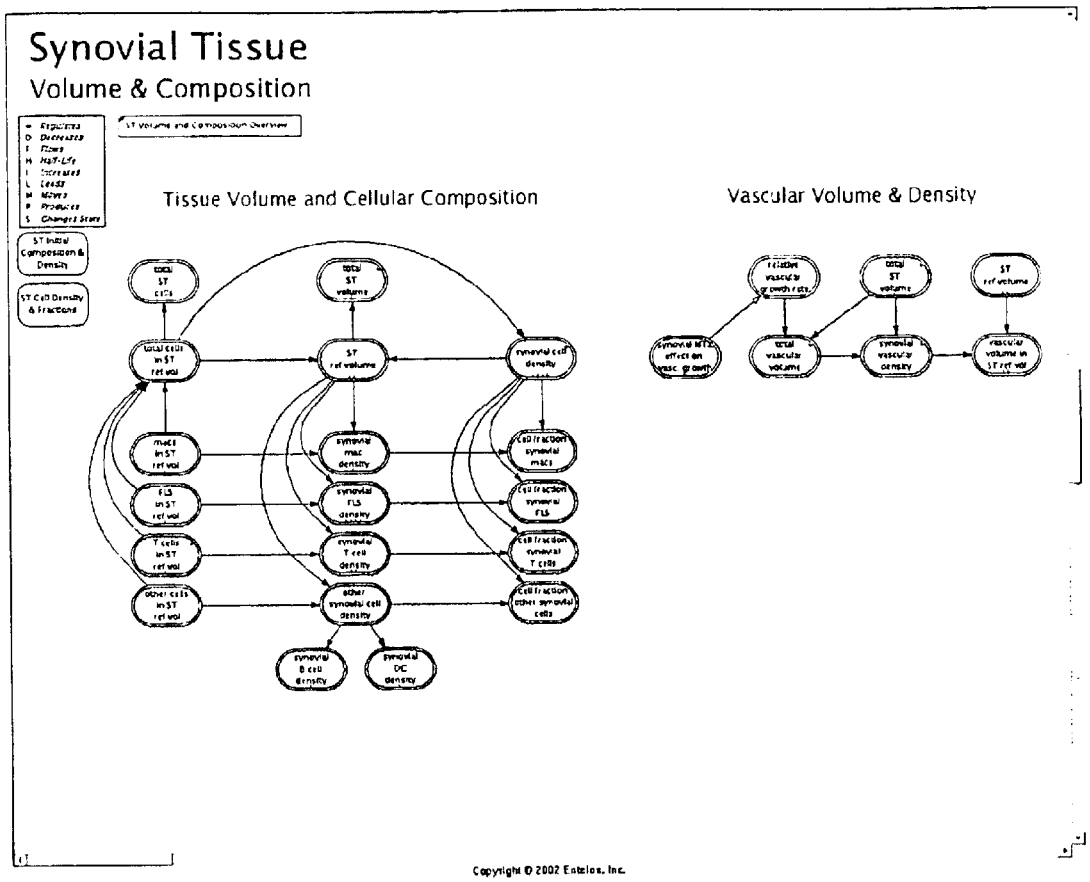
Figure 26:
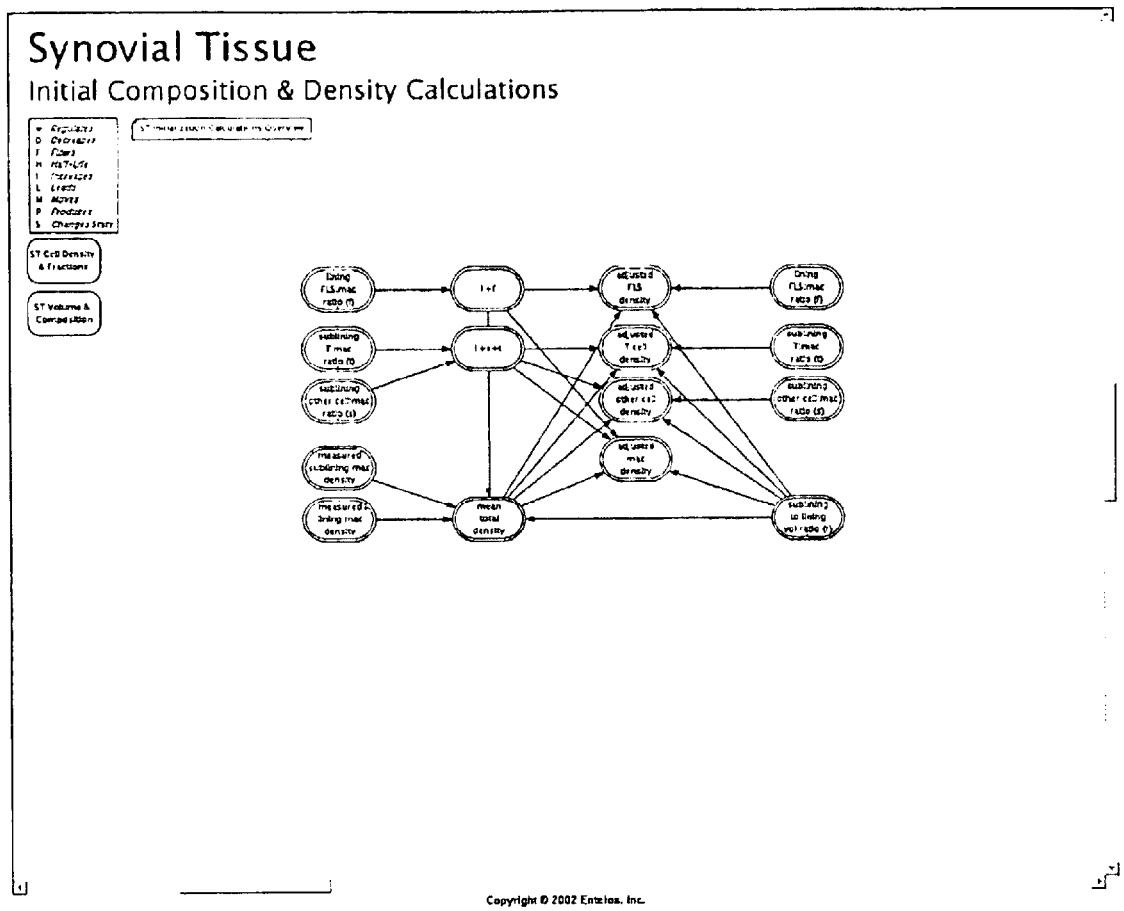
Figure 27:
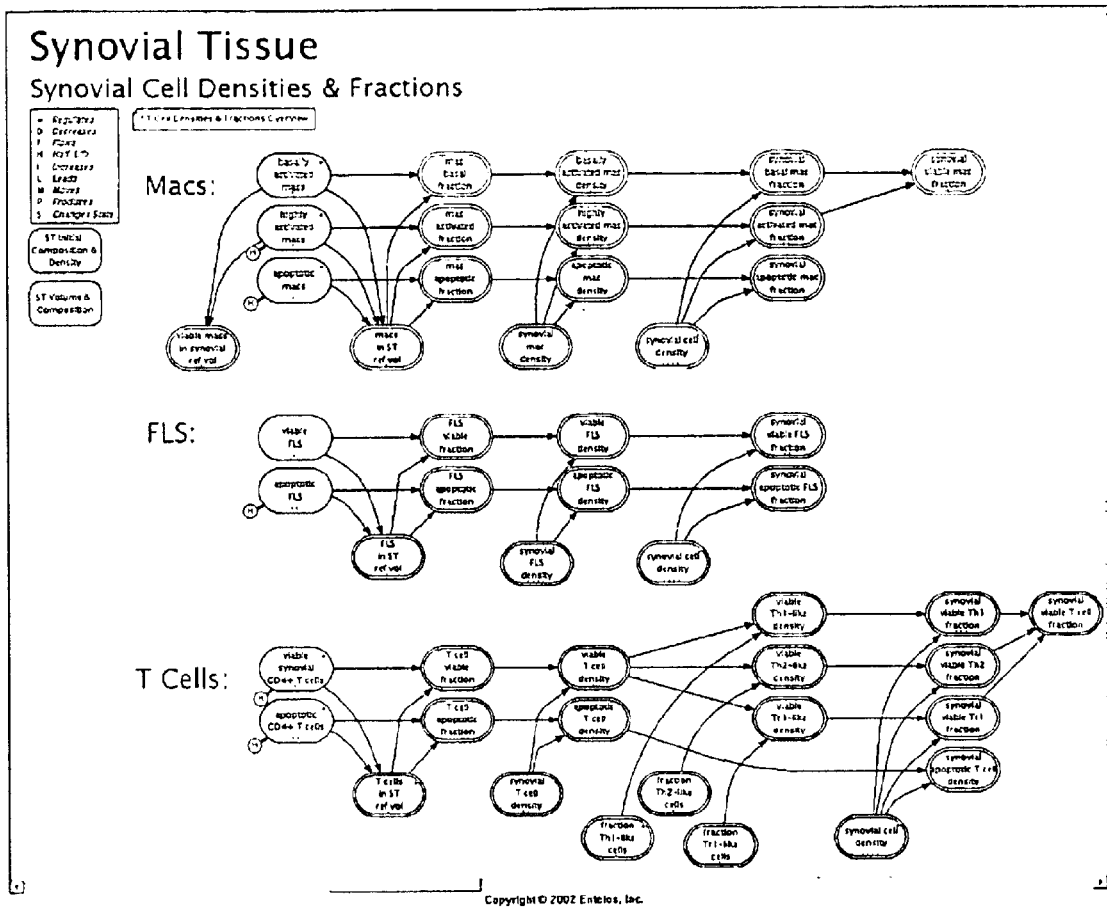
Figure 28:
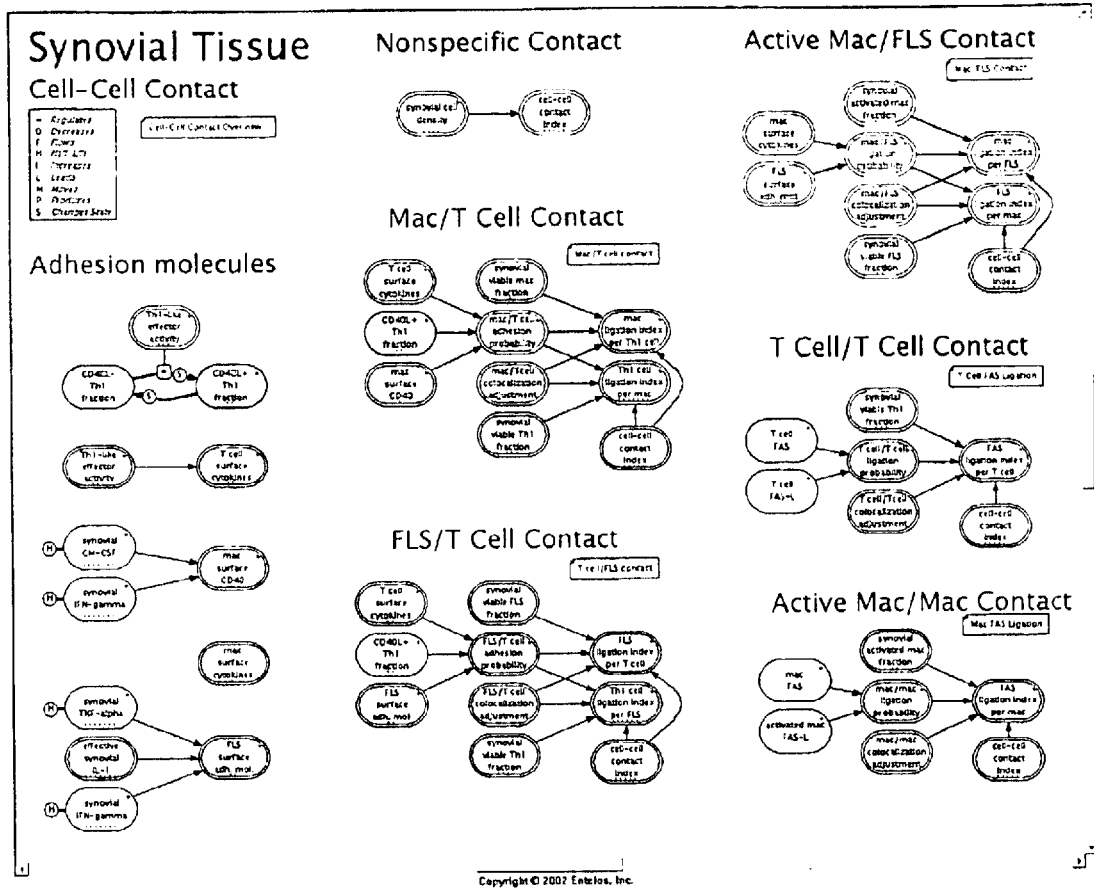
Figure 29:
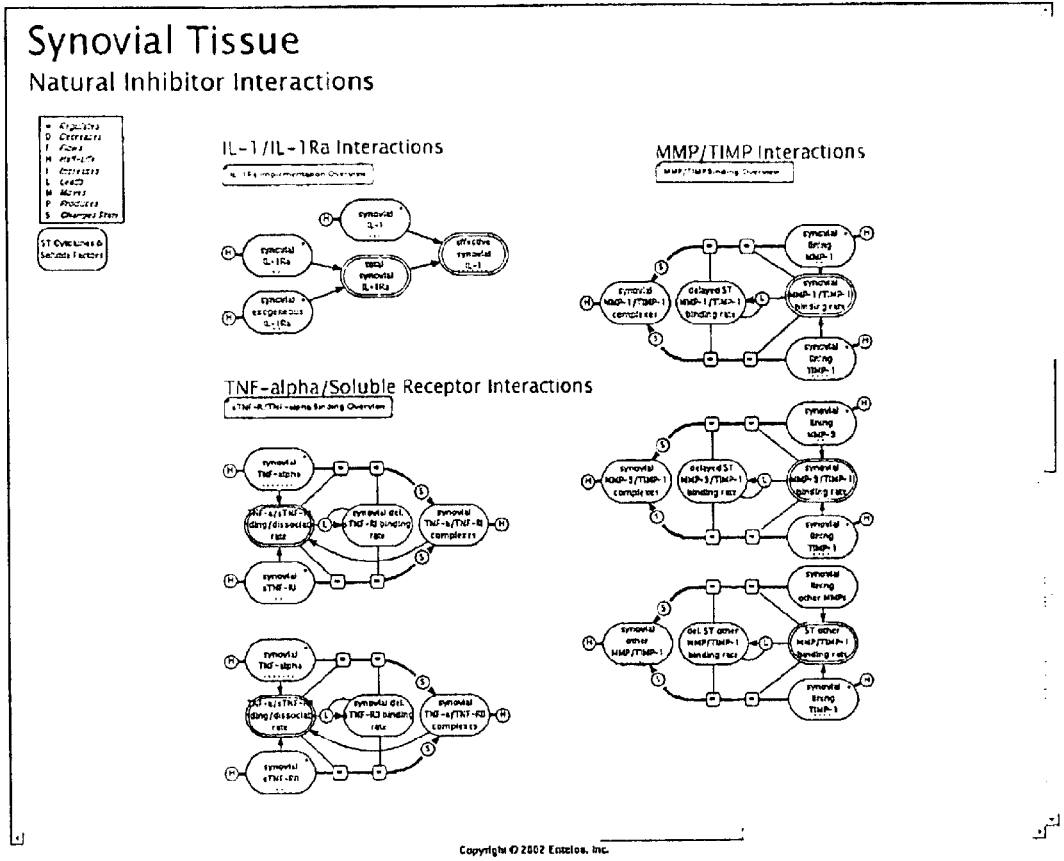
Figure 30:
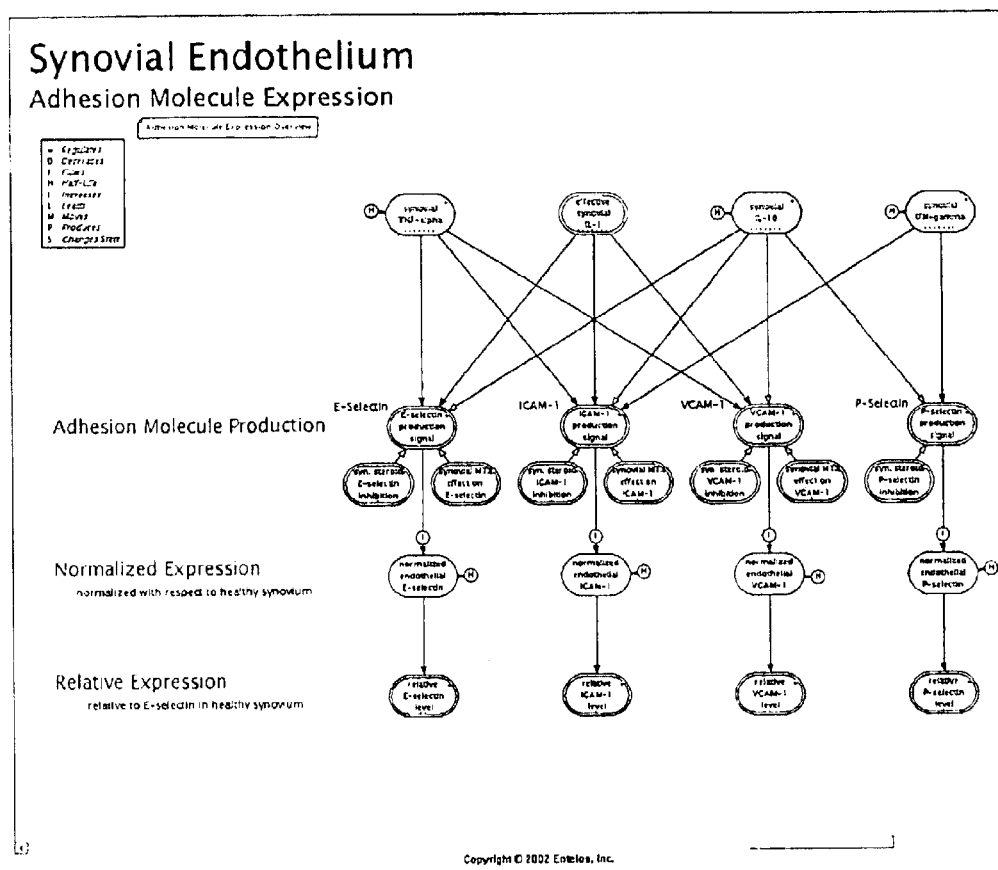
Figure 31:
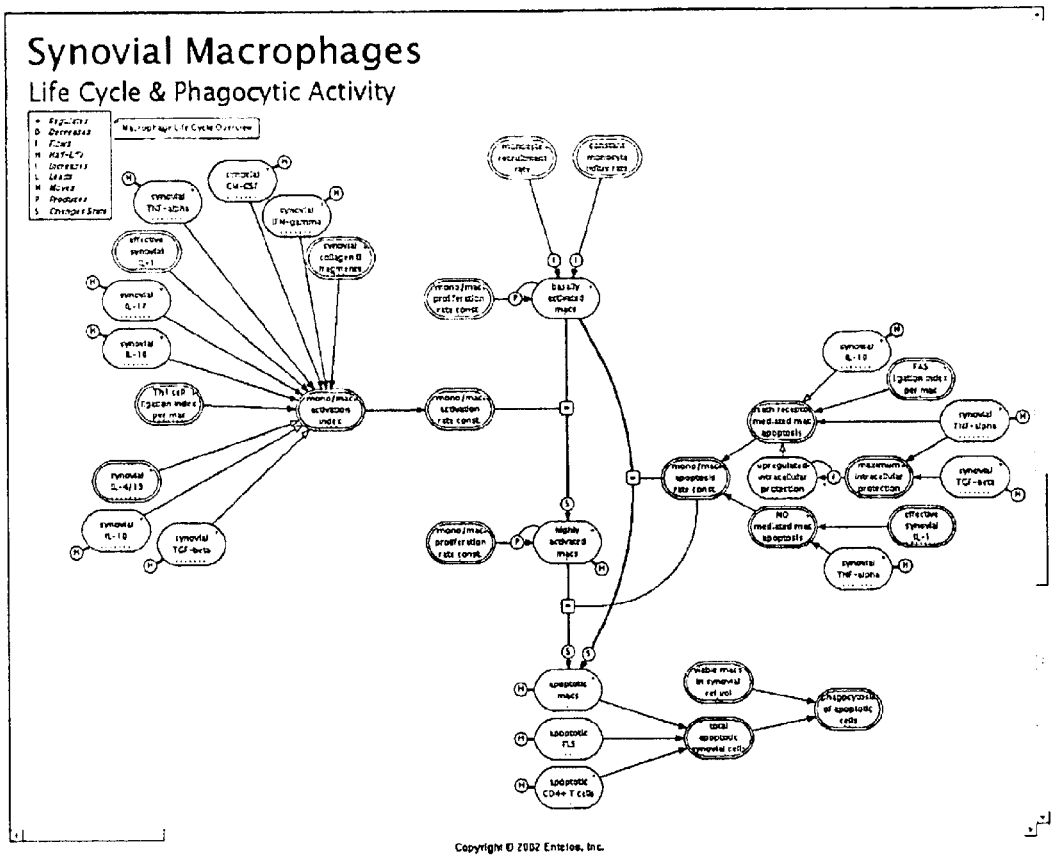
Figure 32:
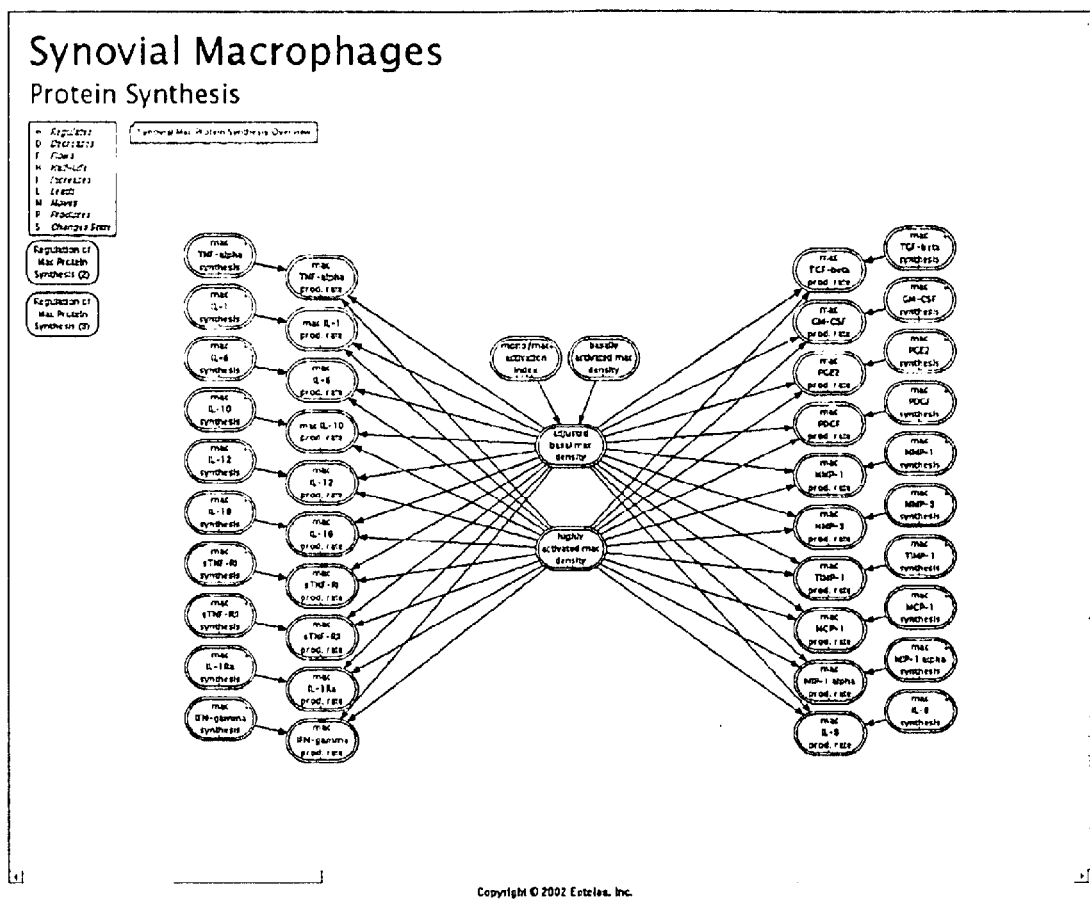
Figure 33:
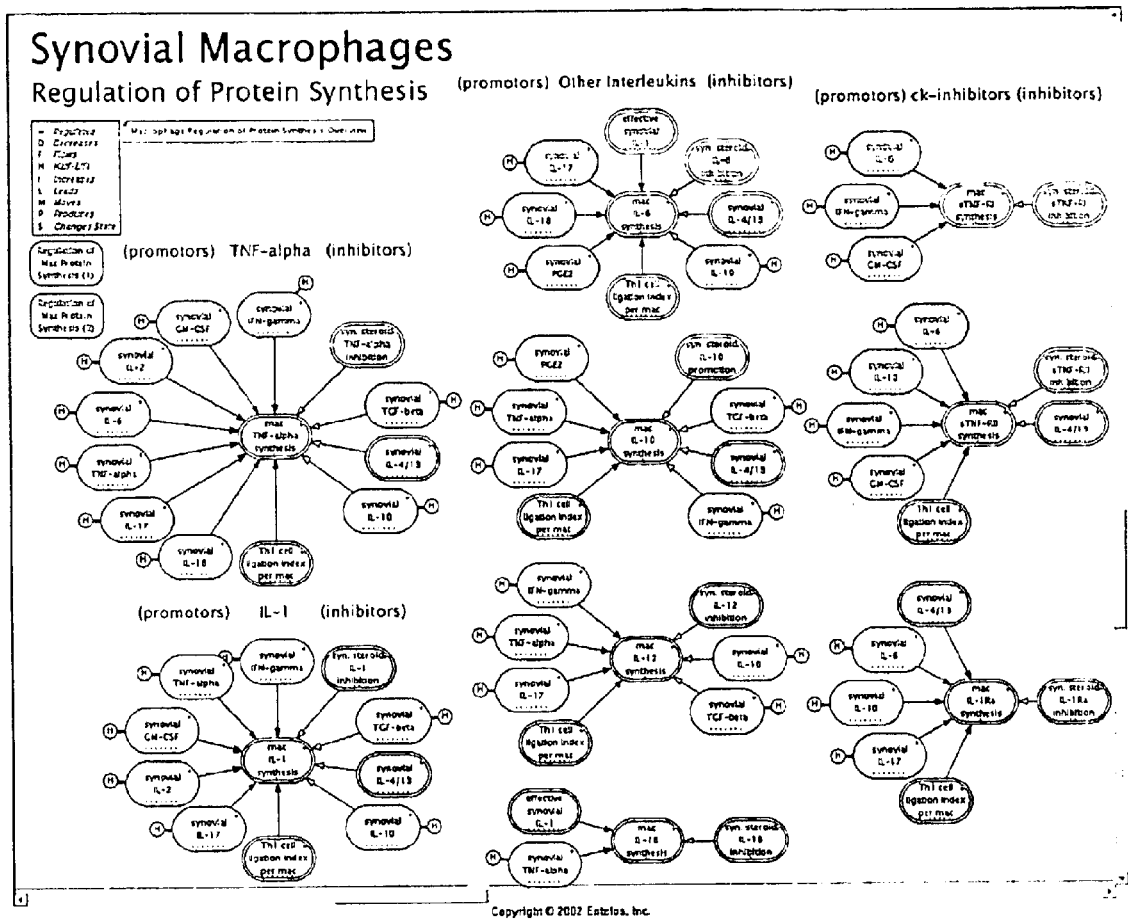
Figure 34:
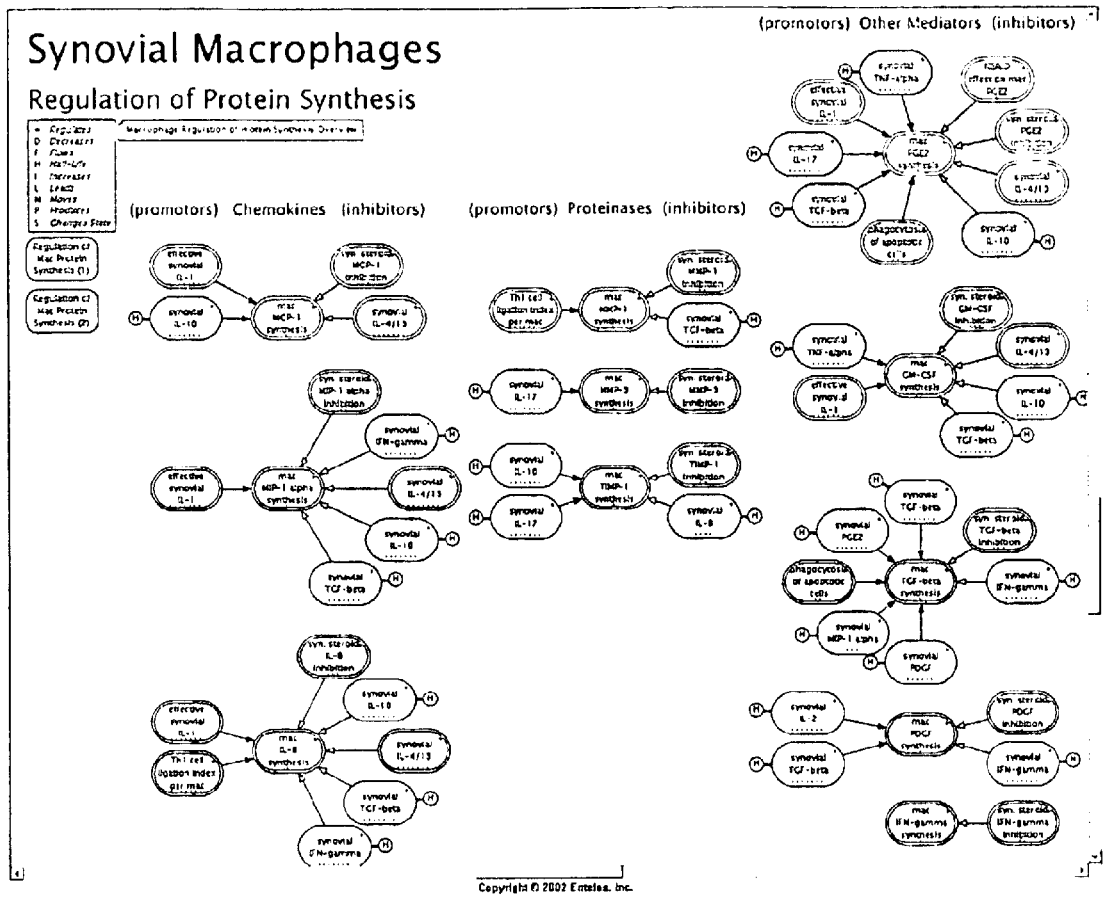
Figure 35:
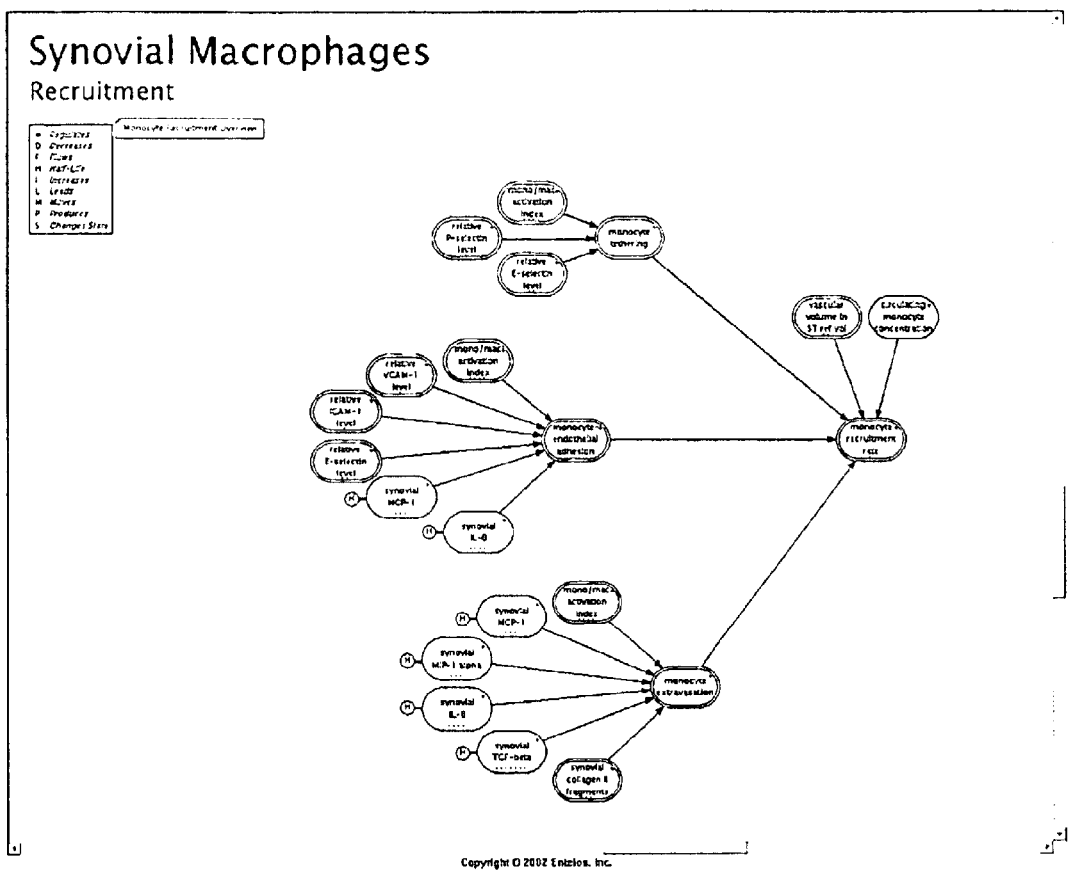
Figure 36:
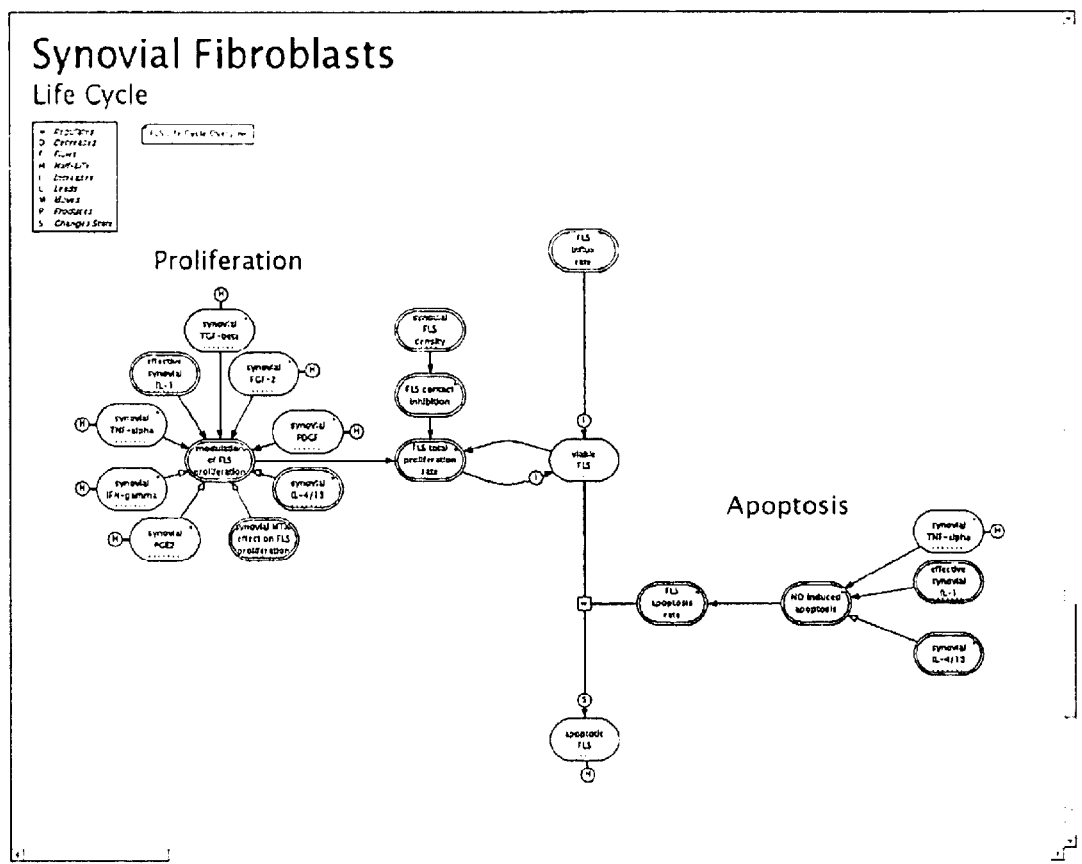
Figure 37:
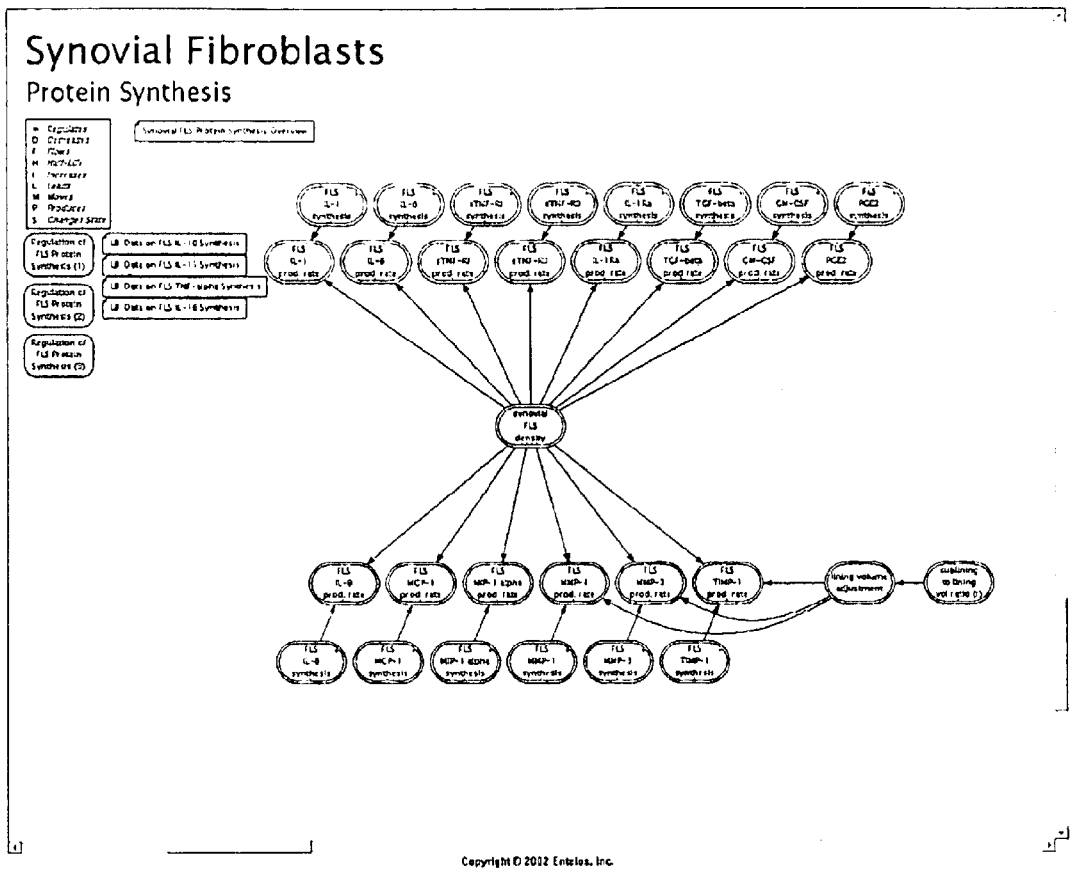
Figure 38:
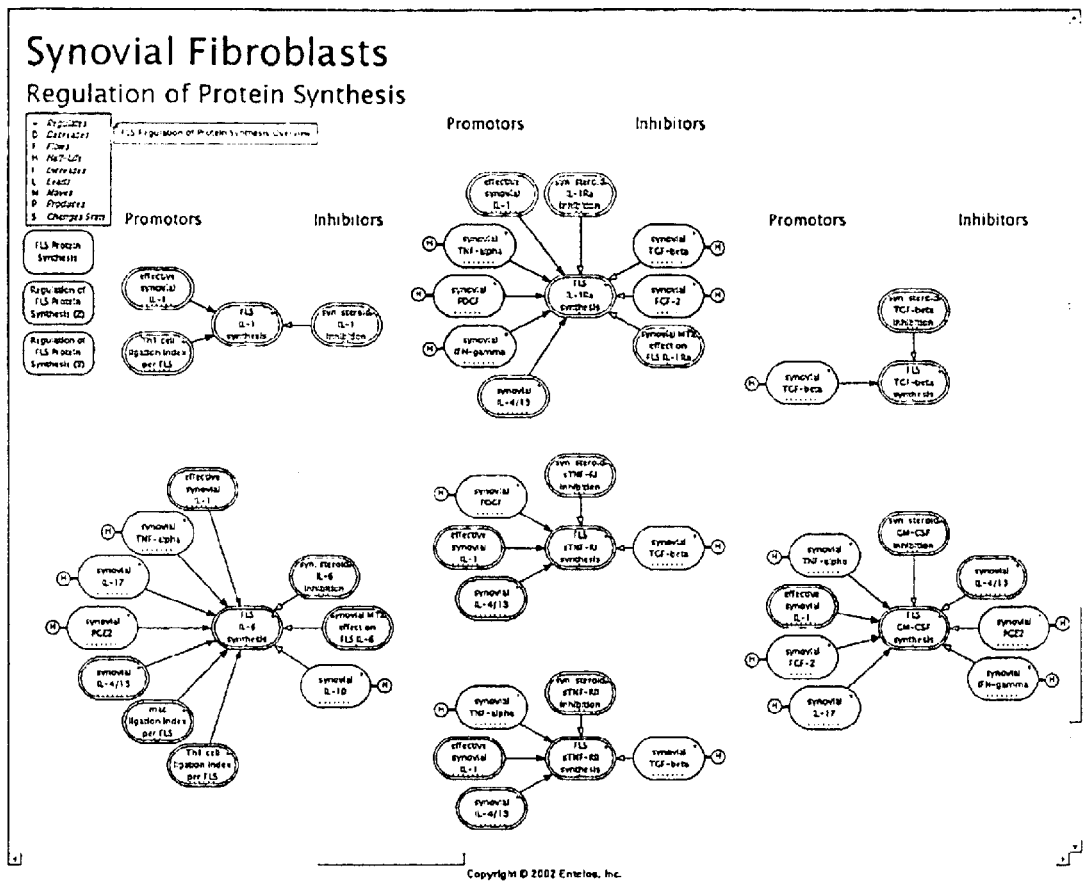
Figure 39:
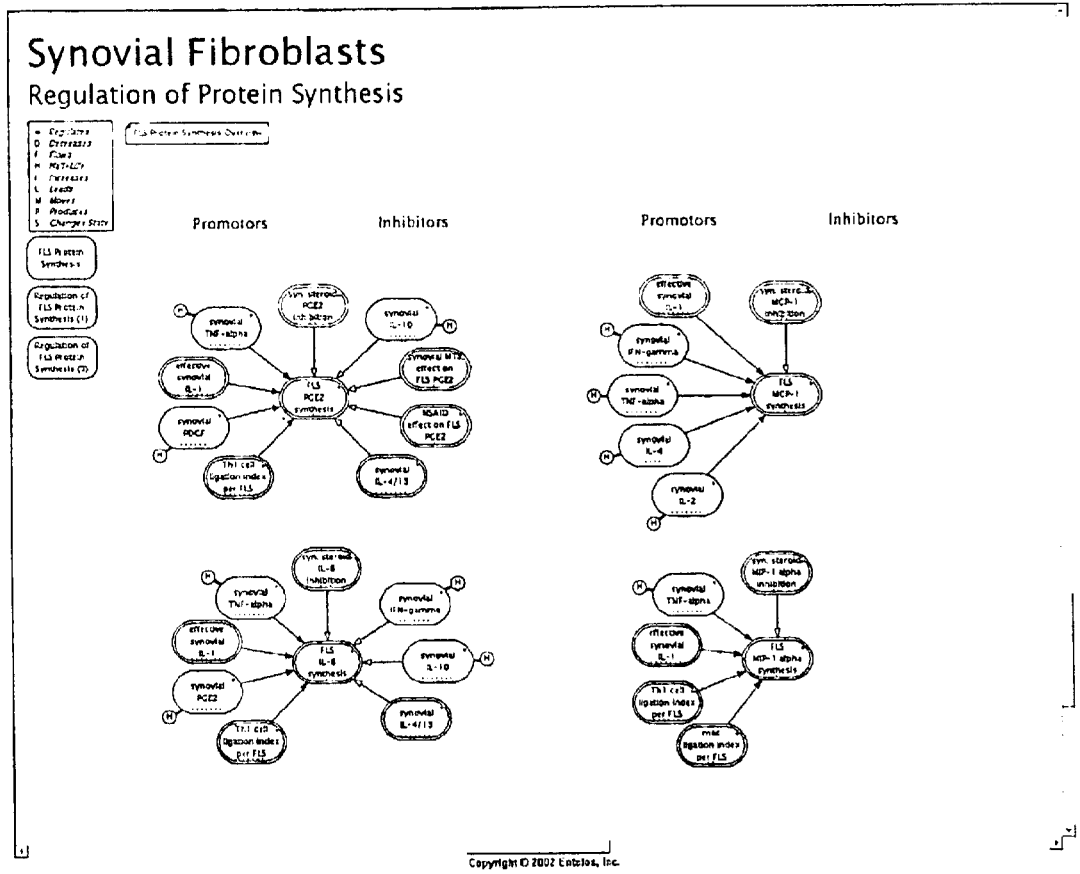
Figure 40:
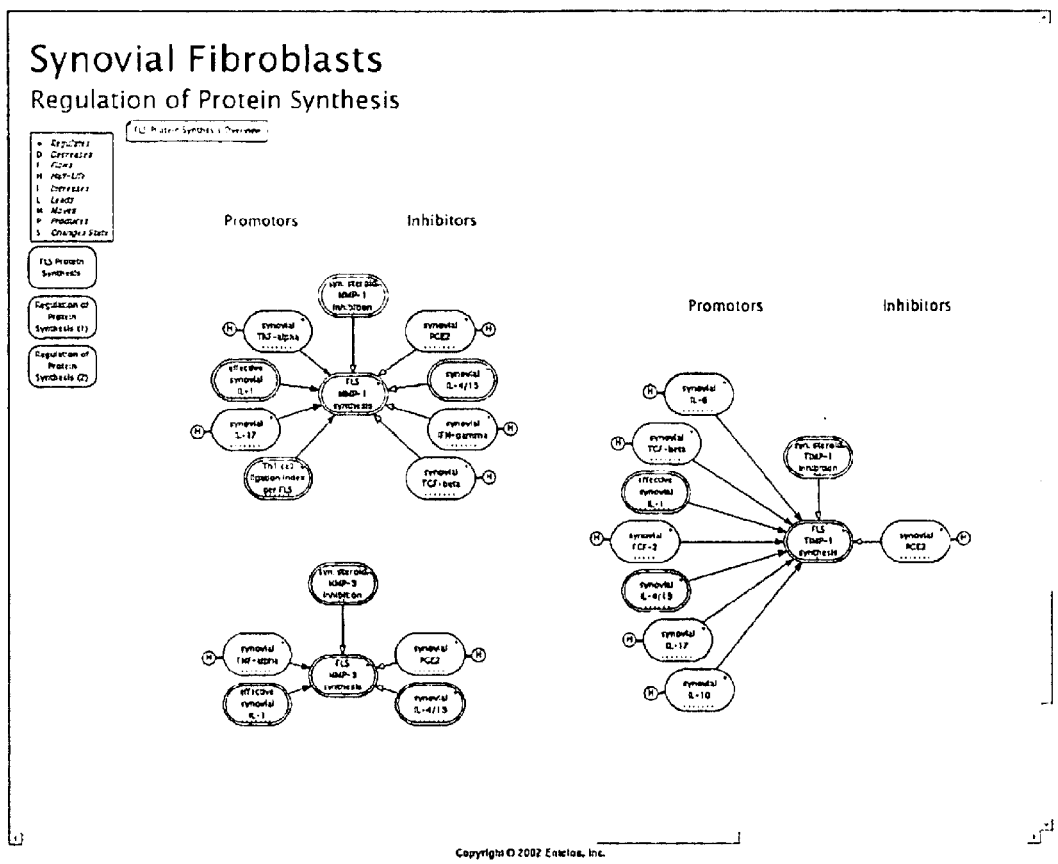
Figure 41:
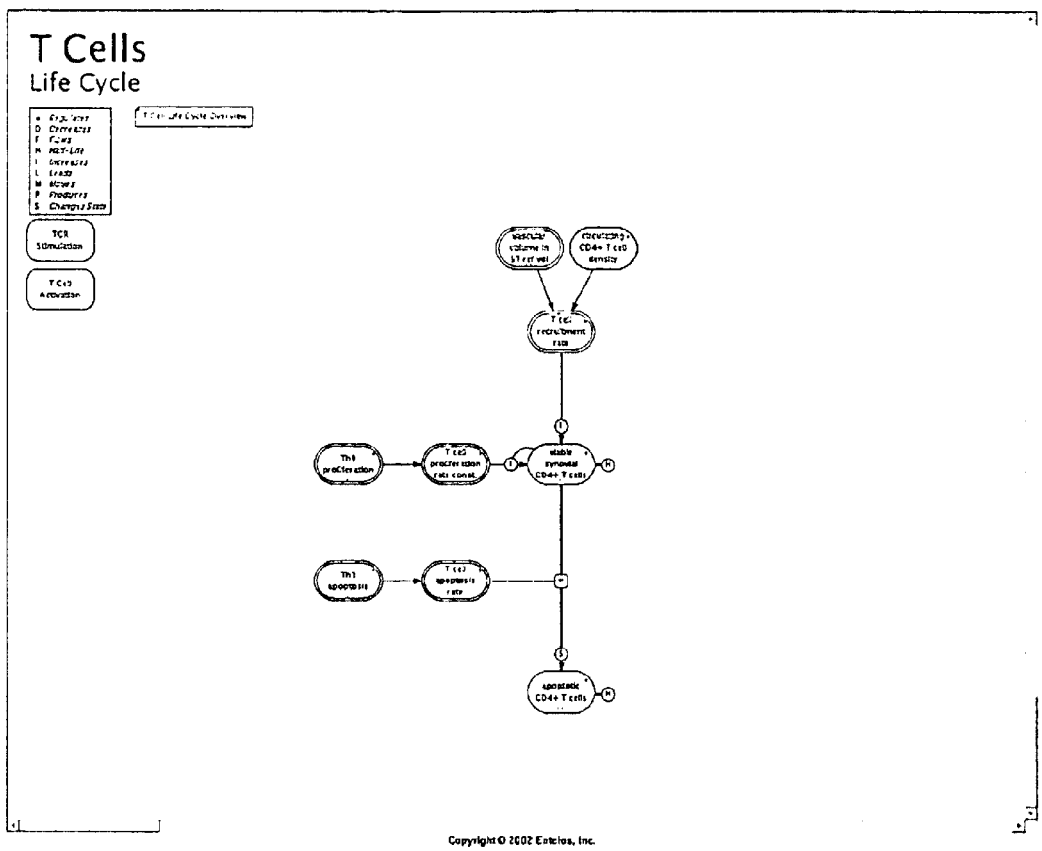
Figure 42:
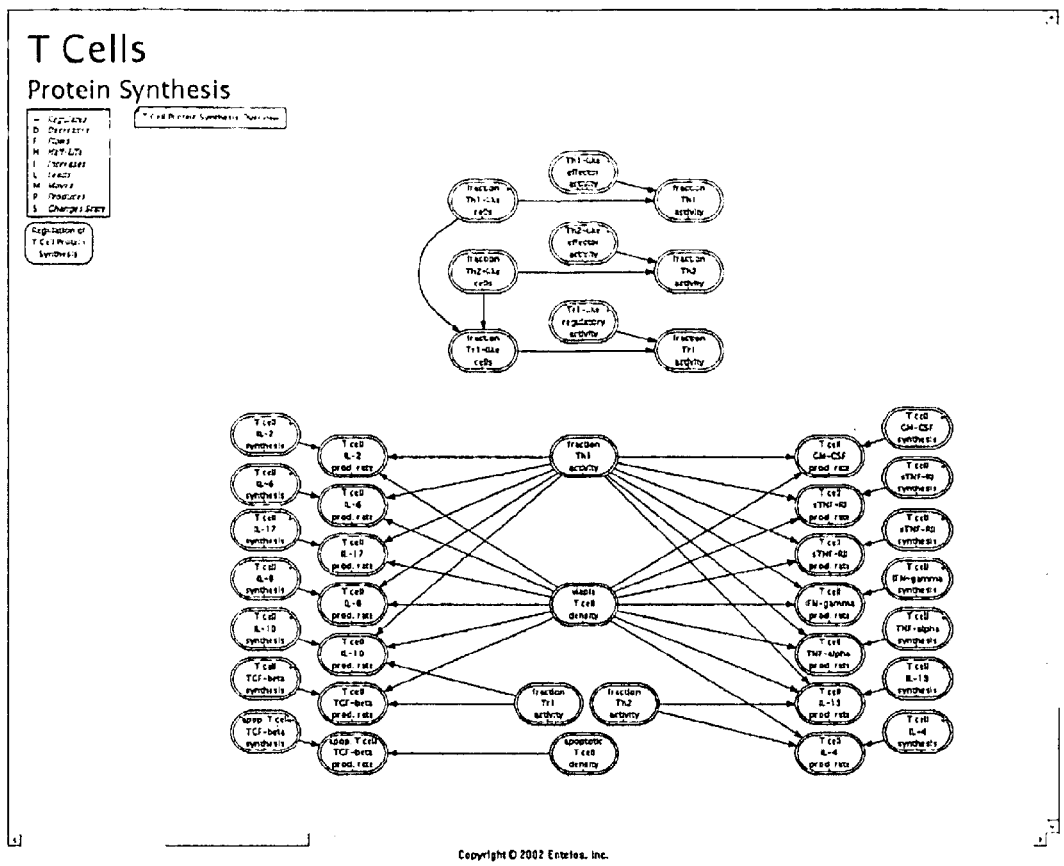
Figure 43:
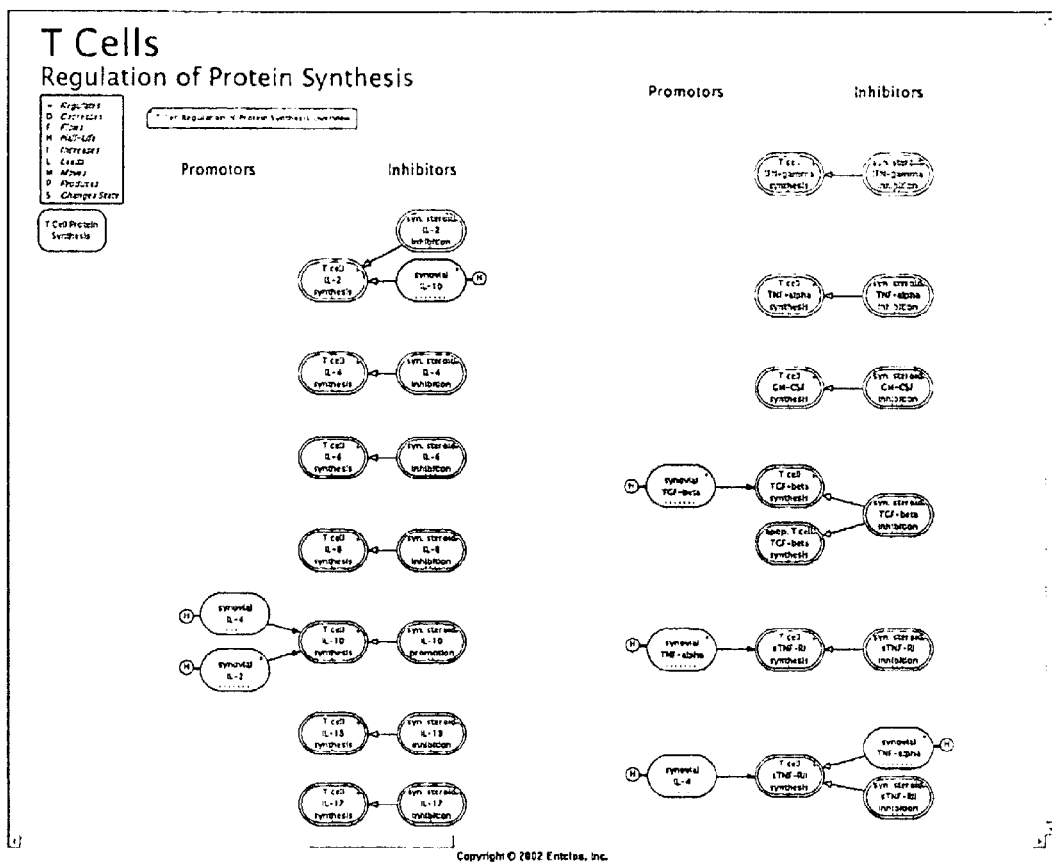
Figure 44:
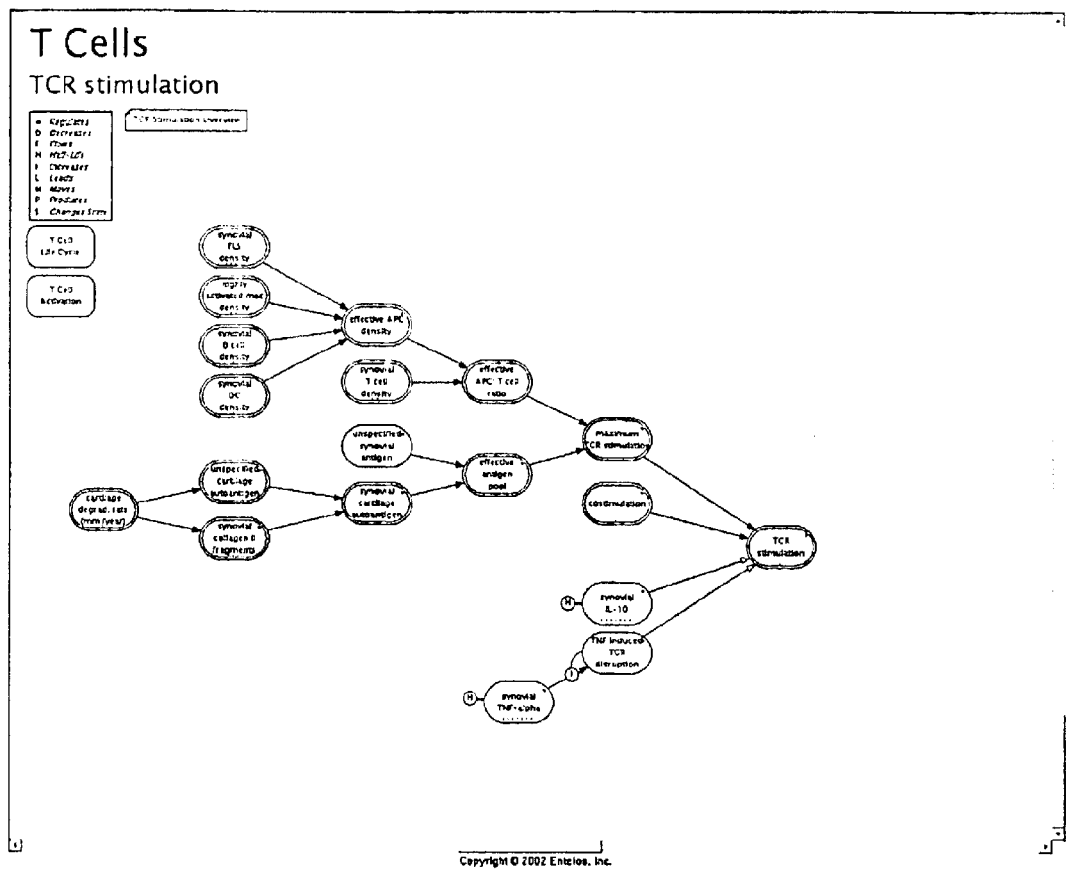
Figure 45:
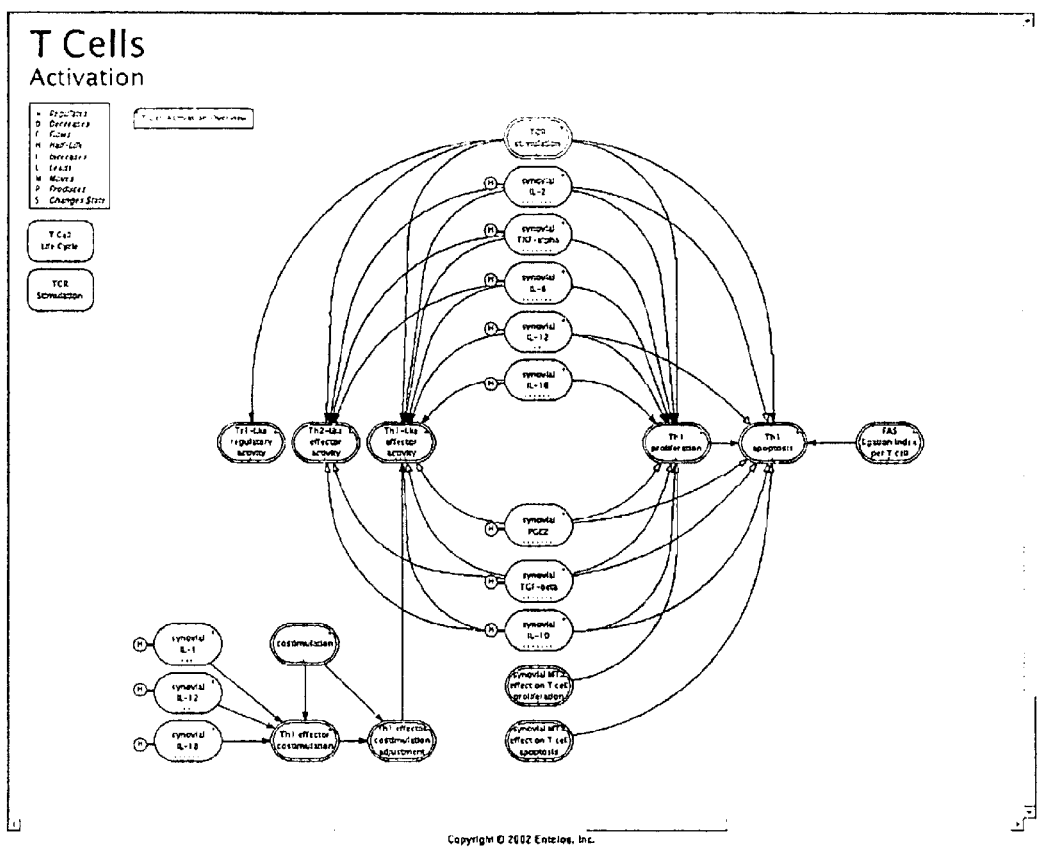

FIG. 10 depicts a flowchart for a method for developing a computer model of a joint according to another embodiment of the invention. At step 1010, data relating to a biological state of the joint is identified. At step 1020, biological processes related to the data are identified. These biological processes define at least one portion of the biological state of the joint. At step 1030, a first mathematical relation among biological variables associated with a first biological process from the biological processes is formed. At step 1040, a second mathematical relation among biological variables associated with the first biological process and a second biological process associated with the biological processes is formed. The biological state of the joint can be, for example, the state of a normal joint or a diseased joint.

Steps 1050, 1060, and 1070 can be optionally performed to produce a simulated biological attribute that is substantially consistent with at least one biological attribute associated with a reference pattern of the joint. At conditional step 1050, a determination is made as to whether a simulated biological attribute or a series of simulated biological attributes is to be produced. If a simulated biological attribute is to be produced, the process continues to step 1060. At step 1060, a set of parametric changes in the first mathematical relation and the second mathematical relation is created. At step 1070, a simulated biological attribute based on at least one parametric change from the set of parametric changes is produced.

Steps 1080, 1090, 1100, 1110, and 1120 can be optionally performed to obtain a representation of the chronological progression of a diseased joint, for example from a healthy state to a disease state. At step 1080, a determination is made as to whether a biological variable or a parameter is converted. If a biological variable is to be converted the process proceeds to steps 1110, and 1120. At step 1110, a first biological variable is converted into a converted biological variable the value of which changes over time. This first biological variable is associated with at least one from the first mathematical relation and the second mathematical relation formed in steps 1030 and 1040. At step 1120, a series of simulated biological attributes are produced based on the converted biological variable. The series of simulated biological attributes are substantially consistent with a corresponding biological attribute associated with a reference pattern of the joint. The series of simulated biological attributes represent the chronological progression of corresponding biological attributes in the reference pattern of the joint. If a parameter is to be converted to obtain a series of simulated biological attributes, the process proceeds to steps 1090, and 1100. At step 1090, a parameter is converted into a converted biological variable the value of which changes over time. This parameter is associated with at least one from the first mathematical relation and the second mathematical relation formed in steps 1030 and 1040. At step

1100, a series of simulated biological attributes are produced based on the converted biological variable.

Another embodiment of the invention is a computer model of the biological state of an animal joint. The computer model comprises code to define biological processes related to the biological state of the joint; and code to define mathematical relationships related to interactions among biological variables associated with the biological processes. At least two biological processes from the biological processes are associated with the mathematical relationships. The combination of the code to define the biological processes and the code to define the mathematical relationships define a simulation of the biological state of the joint. The computer model can further comprise code to define two compartments, wherein one compartment includes biological processes related to synovial tissue and the second compartment includes biological processes related to cartilage tissue. Further, the computer model can include a code to define the interaction between these two compartments.

Yet another embodiment of the invention is a computer executable software code that comprises of code to define biological processes related to a biological state of an animal joint including code to define mathematical relations associated with the biological processes. The biological processes defined by the code are associated with the biological state of the animal joint.

The computer executable software code can further comprise code to define two compartments, wherein one compartment includes biological processes related to synovial tissue and the second compartment includes biological processes related to cartilage tissue. Further, the computer executable software code can include a code to define the interaction between these two compartments.

Another embodiment of the invention is a method for developing a computer model of a diseased animal joint, comprising receiving user-selected indications to define biological processes, each biological process being based on data that relates changes in biological states to biological attributes of a diseased joint; producing a simulated biological attribute associated with at least one biological attribute of the diseased joint based on the combined biology processes; and assessing the validity of the computer model based on a comparison between the simulated biological attribute and a corresponding biological attribute associated with a reference pattern of the diseased joint.

Another embodiment of the invention is a computer model of an animal joint, comprising a computer-readable memory storing codes and a processor coupled to the computer-readable memory, the processor configured to execute the codes. The memory comprises code to define biological processes related to the biological state of the joint and code to define mathematical relationships related to interactions among biological variables associated with the biological processes. At least two biological processes defined by the code are associated with the mathematical relationships. The combination of the codes stored in the memory that define the biological processes and the code that defines the mathematical relationships define a simulation of the biological state of the joint.

The present invention also includes a method for developing an analytical model of an animal joint. This method includes the steps of identifying data relating to a biological state of the joint; identifying biological processes related to the data, the biological processes defining at least one portion of the biological state of the joint; and combining the biological processes to form an analytical representation of the biological state of the joint. In one embodiment, in this analytical model, the analytical representation of the biological state of the joint can be implemented without the assistance of a computer system.

EXAMPLE OF A MODEL COMPONENT

T Cell Life Cycle

The following discussion provides an example of a process by which the modules of the above-described computer model can be developed. As discussed above, the various elements of the biological state are represented by the components shown in the Effect Diagram. These components are denoted by state and function nodes, which represent mathematical relationships that define the elements of the biological state. In general, these mathematical relationships are developed with the aid of appropriate publicly available information on the relevant biological variables and biological processes. The development of the mathematical relationships underlying the module diagram for the T cell life cycle in the synovium will be discussed here as an example.

Figure 8:
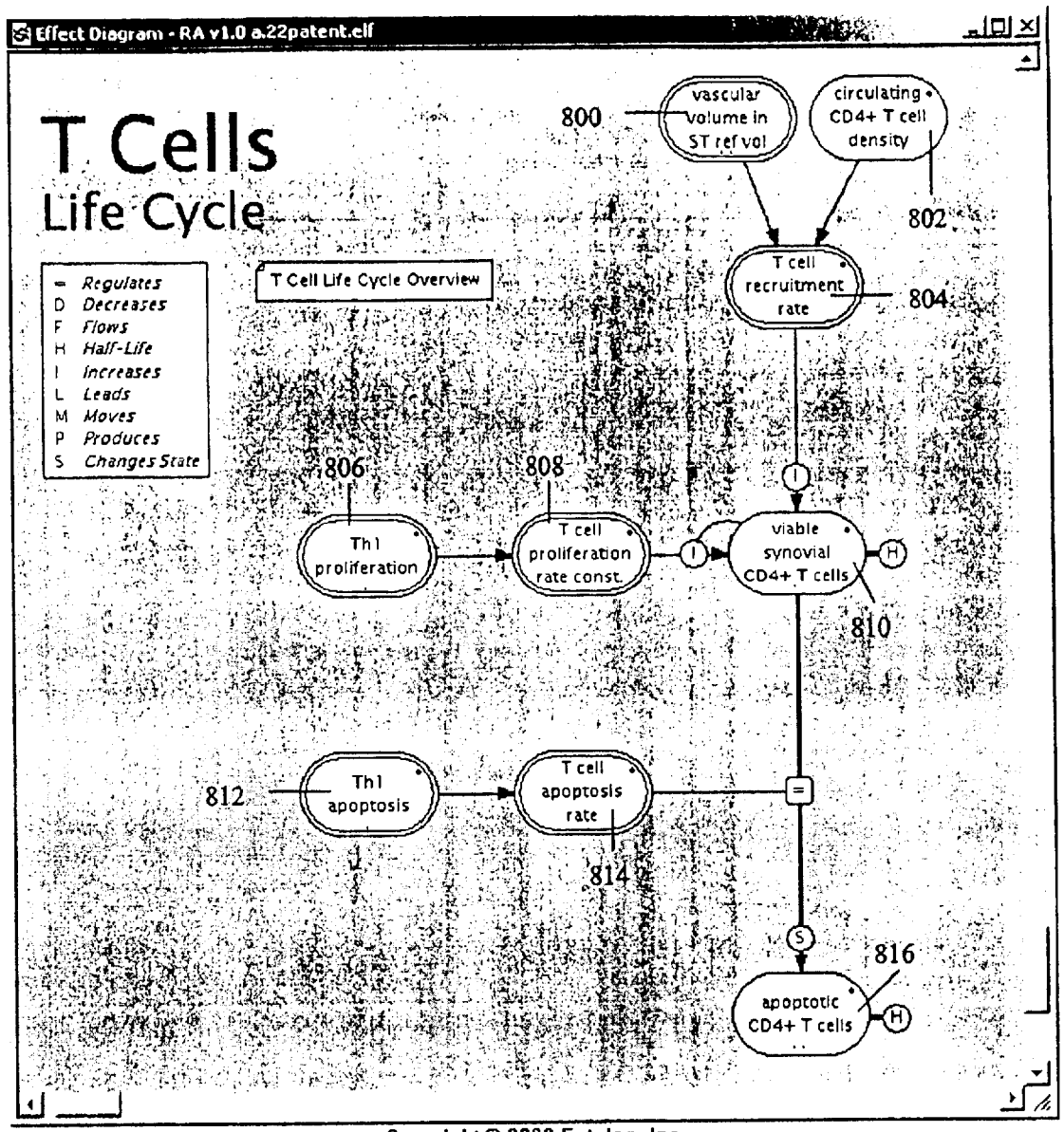
FIG. 8 shows an example of a module diagram for the T cell life cycle in the synovium.

FIG. 8 shows an example of a module diagram for the T cell life cycle in the synovium. Note that for illustration purposes, this module diagram is a rearranged version of the module diagram depicted on FIG. 41.

As FIG. 8 illustrates the physiological components modeled for the life cycle of the synovial T cells include: node 800, vascular volume in synovial tissue reference volume; node 802, circulating CD4+ cell density; node 804, T cell recruitment rate; node 806, Th1 proliferation; node 808, T cell proliferation rate constant; node 810, viable synovial CD4+ T cells; node 812, Th1 apoptosis; node 814, T cell apoptosis rate; and node 816, apoptotic CD4+ T cells.

In a joint affected by RA, $CD4^+$ T cells accumulate in the synovium where they interact with other cell types via soluble mediators and direct cell-cell contact. These interactions are shaped by the specific phenotype and number of the involved $CD4^+$ T cells. FIG. 8 and the following description address only the calculation of the number of Th1 (Type 1 helper T cells) $CD4^+$ T cells in a synovial tissue reference volume. The main processes of T cell turnover modeled are T cell recruitment, proliferation, apoptosis and drainage (by the lymphatic system or synovial fluid). In the model, the numerical balance of these processes determines the number of viable synovial $CD4^+$ T cells, which modulate the net T cell activity in other parts of the model. Some of these processes and the role of T cells are reviewed in Budd & Fortner, *Kelley's Textbook of Rheumatology*, Ruddy et al. eds., pp. 113–129, 2001.

FIG. 8 provides the graphical representation for the differential equations used to track the population of viable and apoptotic synovial CD4+ T cells. As these differential equations depend on calculations of the recruitment, proliferation, and apoptosis rates, the latter are described first, followed by the description of the differential equations governing the population dynamics.

The T cell recruitment rate, which specifies the net influx rate of CD4+ T cells into the synovial tissue reference volume, is determined from the density of circulating CD4+ T cells and the vascular volume in the synovial tissue reference volume as follows:

T cell recruitment rate=reference rate*vascular volume*circulating CD4+ density.

The mathematical relationships associated with the node 804 correspond to the equation for T cell recruitment rate above.

The vascular volume is assumed to be proportional to the vascular surface area and therefore replaces the latter in the function evaluation. The parameter "reference rate" represents the fraction of circulating CD4+ T cells recruited per hour. The "reference rate" parameter subsumes effects including the modulation of recruitment by expression of endothelial adhesion molecules, T cell surface molecules, and chemotactic factors. The density of circulating CD4+ T cells can be estimated to be approximately $1.25 \times 10^6$ cells/ml (Gallin, *Harrison's Principles of Internal Medicine*, Isselbacher et al. eds., Chapter 59, p.529, 1994; Janeway et al., *ImmunoBiology*, Appendix I, p. 636, 2001). The vascular volume is determined elsewhere in the model from the vascular density (5% in current embodiment, see Gaffney et al., *Ann. Rheum. Dis.*, 57:152–157, 1998) and the synovial tissue reference volume. In another embodiment, the value of the parameter reference rate could be computed dependent on the modeled expression of endothelial adhesion molecules, the modeled effects of chemotactic factors, and other processes. This has been done for the recruitment of macrophages in one embodiment of the invention.

The proliferation of T cells is determined from the fraction of cells entering mitosis at a specific moment, as determined elsewhere in the model and represented by the node 806, Th1 proliferation. The T cell proliferation rate constant is then determined by the function:

T cell proliferation rate constant=Th1 proliferation*ln(2)/cycle time where the parameter "cycle time" is the time population doubling time (in hrs) assuming that all cells are proliferating, and the node 806, Th1 proliferation accounts for the proliferation of only a fraction of the cells. The mathematical relationships associated with the node 808 correspond to the equation for proliferation rate constant above.

The apoptosis of T cells is determined from the fraction of cells entering the apoptotic cascade at a given time, as determined elsewhere in the model and represented by the node 812, Th1 apoptosis. The T cell apoptosis rate constant is then determined by the function:

T cell apoptosis rate=Th1 apoptosis*max rate for initiation of apoptosis where the parameter "max rate for initiation of apoptosis" is the maximum rate (1/hr) for entry into apoptosis if all cells are coordinately triggered to apoptose, and the node 812, Th1 apoptosis accounts for the apoptosis of only a fraction of the cells. The mathematical relationships associated with the node 814 correspond to the equation for apoptosis rate above.

The population of viable CD4+ T cells ($T_v$) and apoptotic CD4+ T cells ($T_a$) is determined using the values obtained from the evaluation of T cell recruitment rate (r), T cell proliferation rate constant (p), and T cell apoptosis rate (a). The viable cell population is controlled by recruitment at the determined rate and proliferates at a rate equivalent to the population of viable cells and the proliferation rate constant. In turn, the viable cells enter apoptosis at a rate proportional to the population of viable cells and the apoptosis rate constant, and exit the synovium via drainage characterized by the half-life $t_d$, as represented by the differential equation:

$$dT_v/dt = p*T_v - a*T_v - \ln(2)/t_d*T_v + r$$

The mathematical relationships associated with the node 810 correspond to the equation for $dT_v/dt$ above. The population of apoptotic T cells is controlled by the entry of viable cells into apoptosis at a rate proportional to the population of viable cells and the apoptosis rate constant, and is reduced by phagocytosis and degradation at a rate characterized by decay with a half-life $t_{1/2}$ as represented by the differential equation:

$$dT_a/dt = a*T_v - \ln(2)/t_{1/2}*T_a.$$

The mathematical relationships associated with the node 816 correspond to the equation for $dT_a/dt$ above. These equations then specify the population dynamics of viable and apoptotic T cells.

The values of the parameters used in the various functions within this module were determined so as to match experimental and clinical data and the guidelines described below. In the one embodiment, these guidelines are manifested as the following constraints:

1. populations ($T_v$, $T_a$) are constant over time in the untreated reference patient (reference patient type definition),
2. the fraction of the T cell population that is apoptotic ($T_a/(T_v+T_a)$) is less than 1% (Firestein et al., *J. Clin. Invest.*, 96:1631–1638, 1995; Ceponis, *Rheumatology*, 38:431–440, 1999; Salmon, *J. Clin. Invest.*, 99:439–446, 1997),
3. the doubling time for viable T cells is less than or equal to 24 hours (laboratory knowledge),
4. the maximum time-constant for initiation of apoptosis is less than or equal to 24 hours (laboratory knowledge), and
5. apoptotic cells are phagocytosed within 4–8 hours of entry into the apoptotic cascade.

In keeping with these constraints, in one embodiment, the parameters are set as follows:

"reference rate" for recruitment=0.4/hr, "cycle time"=24 hours; "max rate for initiation of apoptosis"=0.1 hrs$^{-1}$ (90% initiation at 24 hours); half-life for drainage of viable cells ($t_d$)=672 hours (4 weeks); half-life for disappearance of apoptotic cells ($t_{1/2}$)=6 hours. These parameter values are not specifically reported in the public literature but have been determined to comply with constraints such as the ones above which in turn emerge from the public literature or clinical and laboratory experience. These parameter values do not necessarily have to uniquely satisfy the constraints, and can be changed in alternate embodiments with the same or different constraints, such as one describing a patient with increasing accumulation of synovial T cells over time or different apoptotic fractions of T cells.

As this example of the life cycle of synovial T cell model component generally illustrates, the components of the Effect Diagram, denoted by state and function nodes, represent mathematical relationships that define the elements of the biological state being modeled. These mathematical relationships can be developed with the aid of appropriate publicly available information on the relevant biological variables and biological processes. In other words, the Effect Diagram indicates the type of mathematical relationships that are modeled within a given model component. The publicly available information can then put into a form that matches the structure of the Effect Diagram. In this way, the structure of the model can be developed.

Simulation of Biological Attributes of a Diseased Joint

The model is equipped with a set of baseline parameters selected to represent a certain state of the joint. In one embodiment, the baseline parameters are selected to represent established RA. The parameters of the model can be changed to represent varying manifestations of the same joint disease ranging from an absence of disease, over mild disease, to severe disease. The model can also be changed parametrically to represent different profiles of contributions of the involved biological process to the disease. This can be used to create and explore different virtual patient types for the same disease or to create and compare models of different diseases. For example, changing the appropriate model parameters such that macrophage apoptosis is reduced leads to a more severe RA patient type.

The computer model can represent the pathogenesis in a diseased joint, i.e. all or a part of the chronological progression from a healthy to a diseased joint, as well as the chronological progression between disease states of different severity. For example, one means of including disease progression in the computer model can involve replacing one or more biological variables, formerly fixed at a particular value, with one or more biological variables that evolve over time and depend on some previously included or new biological processes. For instance, in one embodiment the number of dendritic cells in the synovium can be set at a fixed value, which represents their number for a specific disease state. Representing disease progression in this case may involve adding new processes such as dendritic cell influx, efflux and apoptosis, and letting the number of dendritic cells change relative to these processes. Another means of including disease progression would be to replace a parameter by a direct function of time, an algebraic function of other biological variables (i.e. a biological process), or via a dynamic systems equation such as an ordinary differential equation.

For example, in one embodiment the previously fixed parameters that specify the reactivity of T cells to cartilage degradation fragments at a specific disease state can be replaced by a direct function of time or by a function of other biological variables to represent the potential role of the development of autoimmunity in the pathogenesis of RA. The depiction of progression of a diseased joint in the computer model can be used to study, for example, the pathogenesis of RA and approaches to cure the disease as opposed to achieve only temporary remission requiring ongoing treatment. Also, pharmaceutical treatments can be explored to prevent or reverse the progression of the disease in the joint.

Numerical Solution of the Mathematical Equations and Outputs of the Computer Model Because the Effect Diagram defines a set of ordinary differential equations as described above, once the initial values of the biological variables are specified, along with the values for the model parameters, the equations can be solved numerically by a computer using standard algorithms. See, for example, William H. Press et al. Numerical Recipes in C: The Art of Scientific Computing, 2nd edition (January 1993) Cambridge Univ. Press. As illustrated above in the T cell life cycle example, equations can be derived, initial conditions can be obtained, and parameter values can be estimated from the public literature. Likewise, other initial conditions and parameter values can be estimated under different conditions and can be used to simulate the time evolution of the biological state.

Note that parameters can also be used to specify stimuli and environmental factors as well as intrinsic biological properties. For example, model parameters can be chosen to simulate in vivo experimental protocols including administration of therapeutic agents. Furthermore, model parameters can be chosen to represent various environmental changes such as aging, nutrition, physical activity, exercise, stress, oxygenation, and blood cellular composition.

The time evolution of all biological variables in the model can be obtained, for example, as a result of the numerical simulation. Thus, the computer model can provide, for example, outputs including any biological variable or function of one or more biological variables. The outputs are useful for interpreting the results of simulations performed using the computer model. Because the computer model can be used to simulate clinical measurements (e.g. percent activated macrophages, percent apoptotic T cells obtained from synovial biopsies) and responses to treatment, the model outputs can be compared directly with the results of such experimental and clinical tests.

The model can be configured so as to compute many outputs, for example, including: mediator concentrations in the synovium and cartilage including TNF-alpha, IL-1, IL-6, IFN-gamma, PGE-2, MMP-1, MMP-3; expression of endothelial adhesion molecules including ICAM, VCAM and E-selectin; cell numbers including macrophage, T cell, fibrolast-like synoviocyte, and chondrocytes numbers; percentages of apopotic or activated cells; synovial tissue volume, cartilage thickness and cartilage degradation rate; matrix composition including collagen II and aggrecan concentration. The outputs can also be presented in several commonly used units.

Note that the computer model can simulate therapeutic treatments. For example, a therapy can be modeled in a static manner by modifying the parameter set of the appropriate cell types or mediators to represent the effect of the treatment on these cell types or mediators. Alternatively, therapeutic treatments can be modeled in a dynamic manner by allowing the user to specify the delivery of a treatment(s), for example, in a time-varying (and/or periodic) manner. To do this, the computer model can include representations of various therapeutic classes (e.g. soluble TNF-receptors and anti-TNF antibodies, IL-1 receptor antagonists, steroids, non-steroidal anti-inflammatory drugs and other disease-modifying drugs including methotraxate) and how these therapeutic treatments can interact with the various cell types and mediators in a dynamic manner.

In sum, the computer model can enable a researcher, for example, to: (1) simulate the dynamics of a diseased joint, (2) visualize key biological processes and the feedback within and between these biological processes, (3) gain a better understanding of the pathophysiology of joint diseases, (4) explore and test hypotheses about diseased joints and normal joints, (5) identify and prioritize potential therapeutic targets, (6) identify patient types and their responses to various interventions, and (7) organize knowledge and data that relate to joint diseases.

Validation of the Computer Model

Typically, the computer model should behave similar to the biological state it represents as closely as appropriate. Thus, the responses of the computer model can be validated against biological measurements and responses. The computer model can be validated, for example, with in vitro and in vivo data obtained using reference patterns of the biological state being modeled. Thus, validation includes simulating the behavior of a certain cell type without input from other components of the model for comparison with in vitro data (e.g. with data on macrophage TNF-alpha synthesis in response to certain stimuli). Validation can further include simulation of the untreated established RA patient for comparison with clinical measurements (e.g. histological markers of cells in the synovium, synovial fluid mediator concentrations). Validation also can include simulating the response of the model to treatment for comparison with measurements from corresponding clinical trials (e.g. response of histological markers of cells in the synovium, synovial fluid mediator concentrations, degradation and erosion scores). For instance, the measurements taken in a trial for a TNF-alpha blocking therapy, which might include data on the response of histological markers in the synovium, may be compared with the response of the appropriate biological variables in the model to a simulated therapy protocol representing the trial. The result of this comparison in combination with known dynamic constraints may confirm some part of the model or may point the user to a change of a mathematical relationship within the model, which improves the overall fidelity of the model.

Methods for validation of computer models are described in co-pending application entitled "Developing, analyzing and validating a computer-based model," filed on May 17, 2001, U.S. application Ser. No. 60/292,175. This application is herein incorporated by reference in its entirety.

Model Components and Behaviors

As discussed above, the computer model of a joint can include multiple interrelated components that each represents an element within the joint. In one embodiment of the computer model, biological processes related to cartilage metabolism, synovial macrophages, macrophage trafficking, synovial fibroblasts, T cells and antigen presentation are included. One or more module diagrams for some of these components are included in FIGS. 11 through 45 for reference. Some of these components are discussed in further detail below.

In addition, the effect of standard therapeutic interventions on inflammation and cartilage degradation can be implemented in the computer model. Examples of such therapeutic interventions are also discussed below.

Compartmentalization

In one embodiment, the computer model of a joint represents two different tissue compartments, i.e., synovial tissue and cartilage tissue. These two compartments are capable of interacting with each other in various ways. One manner of interaction is represented by the influx, from one compartment to the other, of soluble mediators released by the various cell types represented in each compartment. Another manner of interaction between the two compartments is the influx of breakdown products released from cartilage matrix into the synovial tissue, which can modulate cellular processes of cells located in the synovial tissue.

However, the model need not necessarily be limited to these two compartments. The model can be extended to include mathematical modeling of disease-relevant processes occurring at distal sites, such as other extra-articular tissues and whole organs. Examples of such extra-articular compartments can include, but are not limited to bone, bone-marrow, thymus, blood, lymph nodes, spleen, GI-tract, and heart. In addition, the model can also include distinct articular sub-compartments and the cellular processes involved in the generation and regulation of such sub-compartments. Such specific sub-compartments include, but are not limited to vascular tissue, synovial fluid, ectopic lymph-node structures, sensory, and autonomic nerve fibers.

Cartilage Compartment

The cartilage compartment of the model can track cartilage metabolism and cartilage chondrocyte density through health, disease and treatment. In one embodiment, the cartilage compartment can be modeled as a homogeneous section of cartilage at the cartilage-pannus junction. The cartilage compartment can include biological processes related to the chondrocyte lifecycle, the chondrocyte mediator and matrix synthesis, and various processes involved in matrix synthesis and degradation. The computer model can represent the chondrocyte response to and production of factors affecting cartilage degradation, including cytokines such as IL-1, TNF-alpha, and IL-6; growth factors such as IGF, PDGF and TGF-beta; matrix components such as collagen II and aggrecan; and proteases such as MMP-1, MMP-3, and MMP-13. The resulting conditions can determine the net effect of the related processes on the cartilage matrix and the corresponding degradation rate. In one embodiment, the cartilage compartment is modeled such that it is influenced by mediator influx from the synovial compartment and in turn influences the synovial compartment through cartilage matrix components and the efflux of mediators.

The chondrocyte lifecycle can be modeled by tracking densities of viable and apoptotic chondrocytes as a function of chondrocyte proliferation and chondrocyte apoptosis. The chondrocyte mediator synthesis can be implemented separately for each protein as a function of viable chondrocyte density and modulation of protein synthesis including a baseline synthesis (potentially zero) as well as by stimulation and inhibition by mediators represented in the model. The decay of the synthesized mediators can be modeled through individual half-lives of these mediators in the cartilage compartment. Interactions of mediators with each other can also be modeled. Interactions that can be modeled include binding of soluble TNF-receptor (p55 and p75) to TNF-alpha, binding of TIMP to proteinases and inhibition of IL-1 effects by IL-1Ra. In summary, chondrocyte function is modeled by depicting the modulation by autocrine effects and mediator influx from other model compartments.

In one embodiment, the cartilage compartment of the model includes collagen and proteoglycan turnover in the cartilage matrix and uses collagen II and aggrecan as the corresponding, representative matrix components. The synthesis of these matrix components by chondrocytes is implemented in this embodiment separately for each protein as a function of viable chondrocyte density, a baseline synthesis, as well as stimulation and inhibition by mediators represented in the model.

The processing of the matrix components and their incorporation into the cartilage matrix can also be modeled. For collagen II, the modeled processes can include cleavage and turnover of telopeptides, pericellular degradation, incorporation into the cartilage matrix, and degradation of incorporated collagen as a function of proteinase concentrations. For aggrecan, the modeled processes can include pericellular degradation of free aggrecan, deposition of pericellular aggrecan into the fibrillar matrix, lysis of aggrecan out of the fibrillar matrix, and turnover of the free globular G1 domain. The model can track the accelerating effect of aggrecan depletion on collagen II degradation, which represents increased perfusion by mediators, mechanical destabilization and increased access of proteinases to collagen fibrils.

Zonal patterns of cartilage degradation can also be modeled by tracking collagen II and aggrecan turnover in a superficial zone in direct contact with the synovial tissue and an unexposed deep zone located between the superficial cartilage zone and the bone. Thus, the differential effects of collagen II and aggrecan degradation can be modeled.

In one embodiment, the changing geometry of the joint during the cartilage degradation process is modeled by a moving frame implementation in which degradation of cartilage implies that a specified-thickness superficial region of cartilage moves deeper into the cartilage. Thus, two model-defined regions of the cartilage are the superficial zone, which moves with the degradation and the thickness of which is constant, and the deep zone, which exhibits a reduction in thickness as the designated superficial zone moves deeper. In this embodiment, the volume and geometry of the superficial zone remains constant while degradation is taking place. The collagen degradation in the frame (superficial cartilage zone) determines at which rate the frame is shifted or moved. As the frame is moving and the thickness of the deep zone is reduced, the matrix composition in the frame is updated based on the collagen and proteoglycan concentration in the deep zone. The composition of the superficial zone is therefore dependent on both the degradation taking place in the superficial zone as well as the collagen and proteoglycan concentration in the deep zone.

The cartilage thickness at the margins of the cartilage in contact with the synovium as well as the cartilage thickness at a central location (representing cartilage only in contact with synovial fluid) can be modeled. The geometry and composition of the cartilage model can be modified to represent different joints such as metacarpalphalangeal or hip joints.

A joint model including cartilage component can be used, for example, to investigate how changes in cytokine and proteinase activity can lead to the net degradation of cartilage observed in RA. The cartilage component can enable a user to explore the influence of the synovial cytokine profile on the cartilage metabolism and thereby assess the impact of, for example, cytokine-blocking therapies on cartilage degradation in RA. The user also can be able to evaluate the effect of selected anti-MMP and growth factor therapies.

Synovial Tissue Compartment

In the model, the synovial tissue compartment can comprise different cell types. In one embodiment, the cell types can include fibroblast-like synoviocytes (FLS), macrophages, T lymphocytes, B lymphocytes, and dendritic cells. The changes in net density and in tissue volume of a particular cell type can be determined by tracking over time the total number of cells in a reference volume (a scaled equivalent of the synovial tissue volume). The net density and tissue volume can be used to determine tissue growth and retraction. In one embodiment, the initial tissue composition is calculated as the homogeneous equivalent of the experimentally determined composition of heterogeneous synovial tissue: i.e., the cellular compositions and volumes of different compartments in the heterogeneous tissue are mathematically manipulated to represent a homogenous tissue with the equivalent average cellular composition and net volume. The net density and volume of the tissue can be used as indicators of synovial hyperplasia. In addition, the vascularization of the tissue can be determined over time from specified vascular growth characteristics.

In one embodiment, the population dynamics of each cell type is modeled by including processes related to recruitment of cells from the vasculature, influx from nonvascular compartments, cell activation, contact-inhibited or nutrient-limited proliferation, efflux of cells into compartments not represented in the model, and different mechanisms of apoptosis. Each of these processes can be modulated by soluble factors and other synovial influences such as cell contact mediated regulation. The processes related to recruitment of cells from the vasculature can also incorporate the contribution of endothelial expression of adhesion molecules, chemokines/chemoattractants, and the degree of tissue vascularization.

The activation of specific cell types, for example macrophages and T cells, may be modeled. This activation can be modeled as resulting in distinct subpopulations of cells at different activation levels. Activation can include biological processes related to soluble factor and cell contact mediated regulation, which determine conversion of basally activated cells to highly activated cells, each of which pools can be explicitly represented. An alternate means for representation of activation of cells, can involve the calculation of the activated fraction at each time point without division of the population into separate activated and unactivated pools. This fractional activation can be determined by processes related to antigen levels, the presence of antigen presenting cells, T cell reactivity to antigen, and further regulation by soluble and contact mediated influences.

The various cell types in the synovium synthesize soluble factors such as cytokines, chemokines, and proteinases in response to regulation by the synovial milieu. The model can include the regulation of synthetic activity in each cell type, which can contribute to the net soluble mediator levels in the synovial tissue. Regulation of synthesis of each mediator by each cell type can be modeled explicitly. For specific cell types the level of synthetic activity can also be determined by the explicit modeling of activation state/level. The decay of the synthesized mediators can be modeled through individual half-lives of these mediators in the cartilage compartment. Interactions of mediators with each other can also be modeled. These interactions can include binding of soluble TNF-receptor (p55 and p75) to TNF-alpha, binding of TIMP to proteinases, and inhibition of IL-1 effects by IL-1Ra.

Cell contact mediated effects also contribute to regulation of cell population dynamics (including cell activation) and synthetic activity. Cell contact probabilities can be modeled by representing regulated expression of cell surface molecules involved, the prevalence of the different cell types in the tissue, and the likelihood of colocalization in a heterogeneous tissue.

Synovial Macrophages and Macrophage Trafficking

The macrophage component can represent the healthy and hypertrophic presence of macrophages in the synovium and their contributions to the inflammatory process in a diseased joint. The population of macrophages in an inflamed synovium can be modeled by representing processes related to macrophage recruitment and apoptosis in the tissue. In one embodiment, the computer model does not include macrophage proliferation because it contributes minimally to the accumulation of macrophages. The synovial macrophage population can be subdivided into different groups representing resting cells and activated cells. Activation can be calculated based on exposure to cytokines, growth factors, and cell-cell contact. The activation state can in turn determine the repertoire and levels of key cytokines and soluble factors secreted by macrophages.

The macrophage component can include the biological processes related to synovial macrophage population dynamics, including infiltration and apoptosis; activation of macrophages via exposure to soluble mediators; activation of macrophages via cell-cell contact; and production of cytokines and soluble factors by macrophages, including pro-inflammatory candidates (e.g., TNF-$\alpha$, IL-1) and anti-inflammatory candidates (e.g., IL-10).

Inclusion of these processes can allow simulation of behaviors including synovial hyperplasia, the activation of macrophages by various stimuli, and the resulting cytokine and soluble factor production. A joint model including the macrophage component can be used for investigation of (1) changes in synovial hyperplasia and cytokine milieu, resulting from direct targeting of the macrophage population, and (2) effects of cytokine blockade and other therapies on macrophage activation and mediator production and, ultimately, synovial hyperplasia and cartilage degradation.

The macrophage trafficking component can represent the effect of synovial cytokine and chemoattractant concentrations on the recruitment of macrophages from the circulation into the synovium. This representation can enable a user to study the role of macrophage trafficking in synovial hyperplasia. In one embodiment, the computer model includes only a high-level representation of circulating monocytes. The regulation of endothelial adhesion molecules such as ICAM-1, VCAM-1, E-selectin, and P-selectin in response to cytokine stimulation can be represented explicitly. The computer model can further include the production of chemokines such as MCP-1 and MIP-1α by the relevant cell types. In one embodiment, the expression of integrins and chemokine receptors on circulating monocytes are not modeled explicitly. Instead, the effect of cytokines and chemoattractants on monocyte/macrophage trafficking rates can be assessed by assuming an implicit, fixed profile of integrins and chemokine receptors on circulating monocytes.

This macrophage trafficking component can include processes related to the expression of endothelial adhesion molecules, production of chemokines by appropriate cell types, and effect of endothelial molecules and chemokines on monocyte trafficking rates.

A user can target these processes by blocking the involved cytokines or chemokines, or by directly scaling monocyte/macrophage trafficking rates. Thus, the user can evaluate the effects of these strategies on reducing synovial hyperplasia and cartilage degradation.

Synovial Fibroblasts

The synovial fibroblast (type B synoviocyte) component can represent the turnover of these cells and their interaction with synovial macrophages and cartilage in normal or diseased joints. The contribution of fibroblasts to synovial hyperplasia can be the result of a changing balance of proliferation and apoptosis rates, influenced by an alteration in growth factors and cytokines. The fibroblasts interact with synovial macrophages through cell-cell contact and their contribution and response to a common cytokine pool. Fibroblasts also have a direct effector function on cartilage through contribution of proteinases and cytokines to the pool of soluble factors in the cartilage.

The fibroblast component can include processes related to fibroblast proliferation and apoptosis, cell-cell interactions with macrophages, production of growth factors and cytokines, and proteinase synthesis.

The fibroblast component can enable a user to explore the pathological role of synovial fibroblasts in maintenance and regulation of synovial inflammation and hyperplasia in a diseased joint. Another possible use is the assessment of the impact of therapies on fibroblast numbers and protein synthesis. Furthermore, the user can quantify the direct effect of fibroblast function on cartilage degradation.

T Cells

T cells in the model may contribute to joint inflammation through their response to antigen and soluble factors, which in turn leads to activation of other synovial cells. T cells can be represented by a single phenotype, or separated into resting and activated subsets. The phenotype can primarily reflect CD4+ memory behavior, but can secrete both pro-and anti-inflammatory cytokines. Antigen presentation can influence T cell activation states and corresponding cytokine secretion. Population dynamics can be modeled using set influx and outflux rates, as well as proliferation and apoptosis rates that may be modulated by cytokines or therapies. The interaction of T cells with macrophages and fibroblasts can be modeled for through both intercellular contact and cytokine-mediated communication.

This component can include processes related to T cell population dynamics (constant influx/outflux; cytokine-regulated turnover), T cell secretion of cytokines and soluble factors, both pro-inflammatory (for example, IFN-γ) and anti-inflammatory (for example, IL-10), T cell stimulation via reactivity to antigen presentation, T cell stimulation by cytokines and soluble factors, and T cell stimulation by cell-cell contact with macrophages and fibroblasts.

This component can simulate the T cell accumulation within the joint, the extent of activation of these cells, and their contribution to the cytokine milieu. A potential application of a joint model incorporating this component includes exploring the contribution of T cells to joint pathology by modulating their numbers and response to antigen. The user also can determine the outcome of altering population dynamics (e.g., inducing T cell apoptosis), desensitizing T cells to antigen, blocking specific cytokines, and inhibiting contact-mediated intercellular communication.

Antigen Presentation

This component can represent at a high level the presentation of antigens to T cells by an antigen presenting cell pool that subsumes the specific roles played by dendritic cells (DCs), B cells, and macrophages. The population of antigen presenting cells can reflect the dynamics of macrophage numbers but can assume a fixed number of DCs and B cells in the synovium. In one embodiment of the computer model, recruitment and turnover of DCs and B cells are not explicitly modeled. A single antigen pool can be fed by cartilage autoantigen, generated during tissue destruction, and can include a constant level of other self or exogenous antigens.

This component can include processes related to determination of a net antigen pool consisting of cartilage degradation products and constant background antigen, and determination of a net antigen presentation efficiency and level.

This component can reproduce the presentation of antigen to T cells. The user can target this function by means such as modulating antigen uptake and presentation efficacy, and altering the relative contribution of each cell type to antigen presentation.

Synovial-Cartilage Interactions

In one embodiment, the model includes the interaction between synovial and cartilage compartments. In particular, the interaction can be modeled using the following two techniques: (1) representation of processes related to infiltration of soluble factors from synovial tissue to cartilage (and vice versa) and (2) representation of processes related to stimulation of synovial cell function by cartilage degradation products.

The first method involves the modeling of the flux of different molecules between the two compartments. This calculation includes equilibrium partitioning of the molecules between the compartments, and the redistribution by diffusion of the molecules within a given compartment. Thus, factors such as IL-13 produced only within the synovium may infiltrate the cartilage, and modulate synthetic and catabolic activity in the cartilage.

The second method involves the stimulation of synovial cell function by cartilage degradation products including collagen-II and proteoglycan fragments. Specifically, in this method, processes related to stimulation of antigen-specific responses in T cells by collagen-II and proteoglycan fragments, chemoattraction of macrophages, and activation of macrophages are represented.

Other methods for representation of synovial-cartilage interactions include the representation of processes related to action of synovial cells and mediators at the cartilage surface, and transport of mediators from one compartment to another via an intermediate compartment such as synovial fluid.

Therapies and Interventions

The effect of standard therapeutic interventions on inflammation and cartilage degradation can be simulated in the computer model. These simulations can allow, for example, further calibration of the computer model. One method of implementing a therapeutic intervention is to change biological processes already in the model, which are directly or indirectly affected by the intervention. This change may involve changing existing parameters or biological variables, which are specifically added to represent the therapeutic intervention. For example a major effect of non-steroidal anti-inflammatory drugs (NSAIDs) may be implemented by changing parameters characterizing the PGE-2 synthesis of the affected cell types in the model. Another method of implementing a therapeutic intervention is to implement one or more additional biological processes representing the effects of a therapeutic intervention. For instance, the effect of exogenous soluble TNF-alpha receptor may be represented by explicitly modeling the binding process of TNF-alpha to the exogenous receptor in the affected compartments. The computer model can focus, for example, on the local response to therapy and not on systemic effects. In an alternative embodiment, the computer model can focus on the local response to the therapy and the systemic effects.

Figure 5:
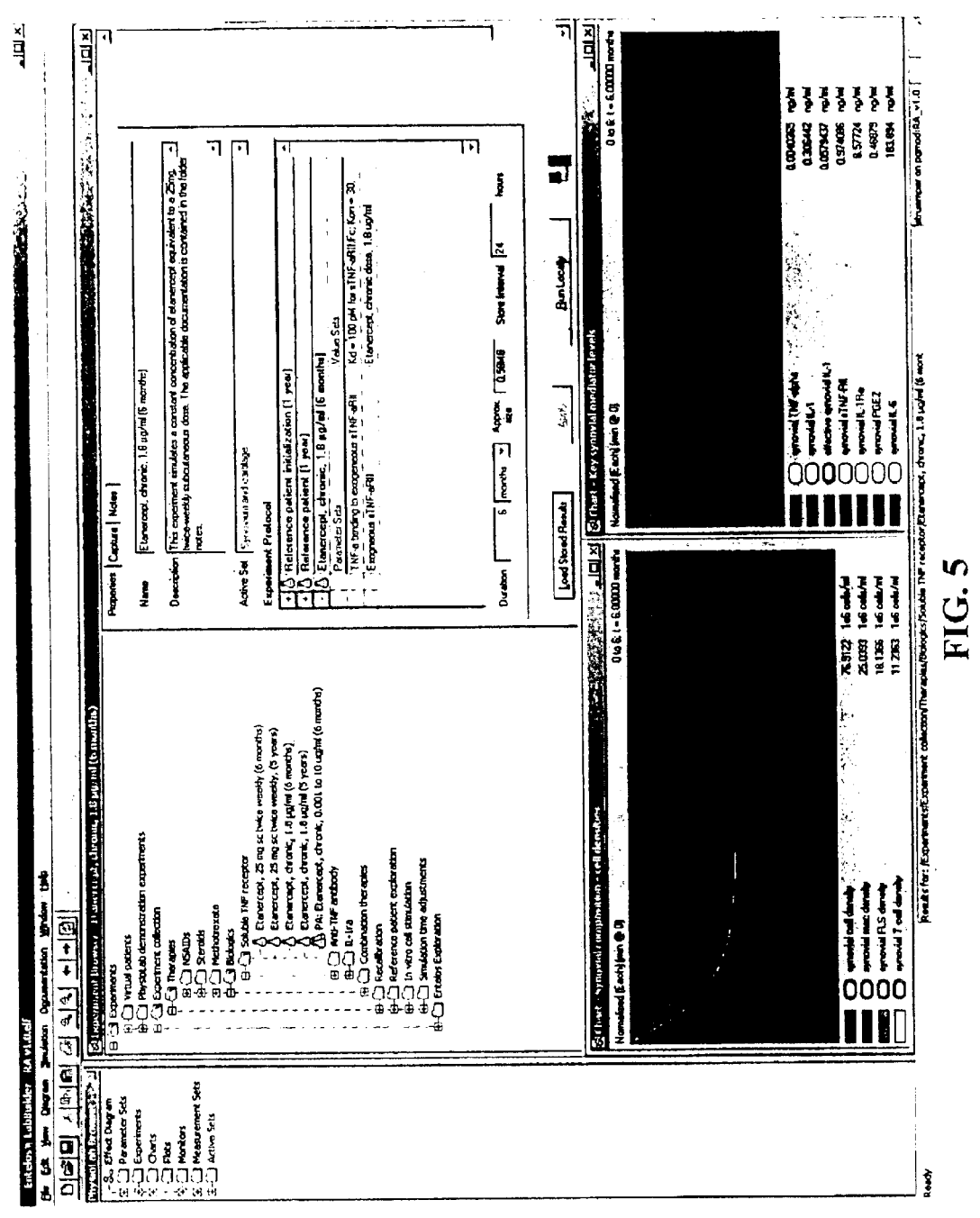

FIG. 5 illustrates an example of a display screen having a PhysioLab® Browser window, chart windows and an experiment browser window, according to an embodiment of the present invention. The example of the display screen shown in FIG. 5 has two windows each displaying a chart: a chart for synovial cell densities over time (center low) and a chart for key synovial mediator levels over time (lower right hand corner).

FIG. 5 also includes an example of a browser window on the upper left-hand side. This experiment browser window allows a user to define, for example, virtual patients, calibration experiments, demonstration experiments, and tests for developers and therapies. These experiments and tests can be defined through the use of parameter sets and value sets where the user can modify the physiology of the joint with alternate values indicative of aspects of a diseased joint. In one embodiment of the computer model, a parameter set is based on the method described in U.S. Pat. No. 6,069,629 entitled "Method of providing access to object parameters within a simulation model," which is incorporated herein by reference. The user can specify alternative value sets, for example, according to the method described in U.S. Pat. No. 6,078,739, entitled "Managing objects and parameter values associated with the objects within a simulation model," which is incorporated herein by reference.

The inclusion of different therapies can allow investigation of the efficacy of combined therapies. The therapies described below define the current standard of care for RA patients and can be addressed in the computer model.

The effects of NSAIDS can be represented. This family of therapies relies on inhibition of cyclooxygenase production to reduce inflammation. In one embodiment the effect of NSAIDs can be modeled as a direct suppression of PGE-2 synthesis.

The effects of glucocorticoids can also be represented. Glucocorticoids are a standard RA therapy with both positive and negative consequences on RA disease progression. In modeling glucocorticoid therapy, the computer model can reproduce the following primary effects: alteration of PGE2 production, alteration of mediator production, reduction of inflammation, and reduction of cartilage degradation.

In another embodiment the effects of methotrexate are represented. The role of the standard RA and anti-cancer therapeutic agent methotrexate in targeting highly proliferative cells can be incorporated into the model. The following known effects of this therapy can be represented: modification of cellular proliferation and reduction of cartilage degradation.

The effects of anti-TNF-α and anti-IL-1 therapies can be represented. These therapies can be implemented via mechanisms such as binding of active cytokine to therapeutic agents, reduction of effects of cytokines through competition from receptor antagonists, as well as reduction of concentration of active cytokines equivalent to the reduction of their effects by competing receptor antagonists. The computer model can represent, for instance, the following effects of therapies: changes in cell numbers, adhesion molecule expression, mediator concentrations, and rate of cartilage degradation.

Testing of combinations of these therapies with each other or with traditional therapies using the present invention should prove valuable. In addition, the computer model can allow explorations of other non-standard, investigational therapies. In one embodiment of the computer model, partial treatment of these therapies can be included. Certainty of the outcome of these therapies can be based on the quality of available data.

Figure 6:
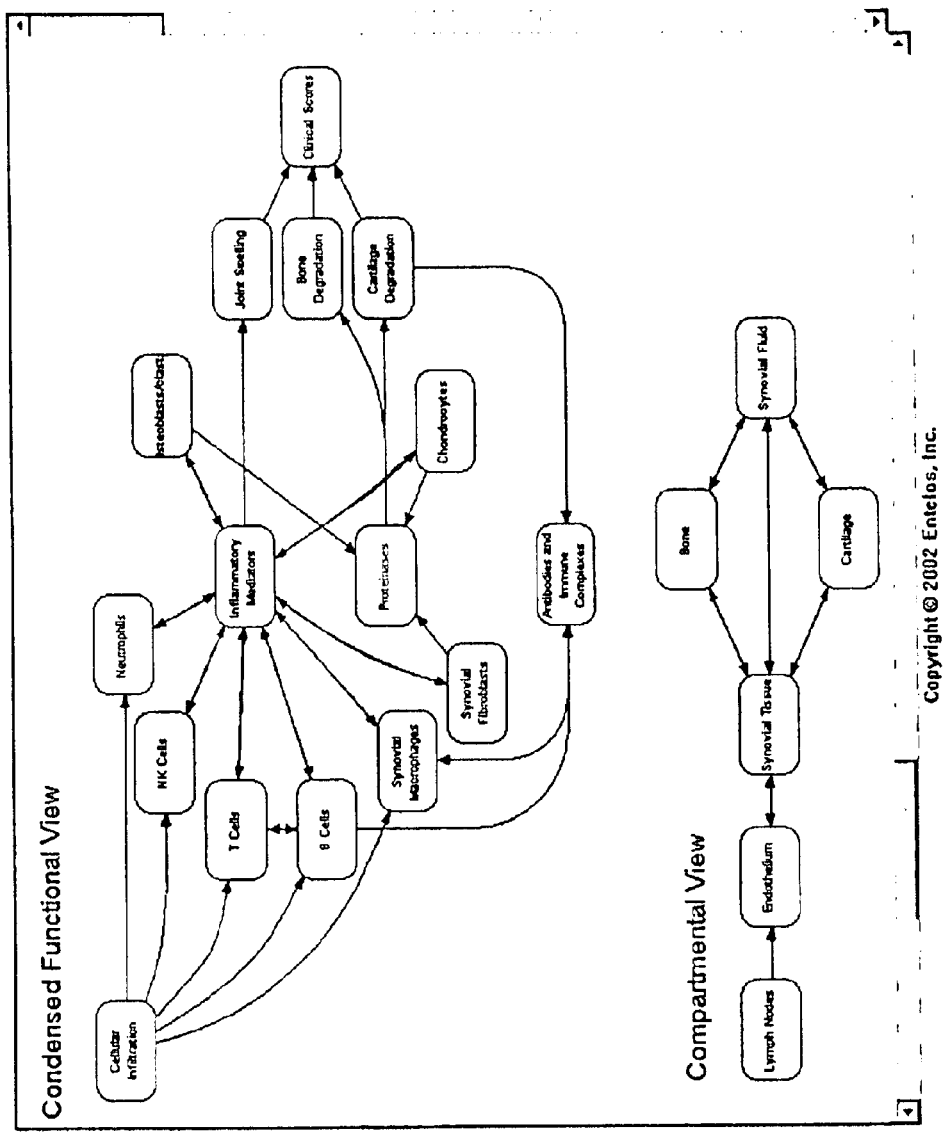
FIG. 6 shows an alternative summary diagram having a condensed functional view and a compartmental view of RA, according to another embodiment of the present invention.

Although the present invention has been discussed above in reference to examples of embodiments, other embodiments are possible. For example, although the summary diagram discussed in reference to FIG. 2 illustrates one possible embodiment, other summary diagrams are possible that consider other aspects of the RA disease or a healthy joint. For example, FIG. 6 shows an alternative summary diagram having a condensed functional view and a compartmental view of RA, according to another embodiment of the present invention. As FIG. 6 shows, the summary diagram for RA can define components and their interrelations in addition to those shown in FIG. 2. These components can be considered from the perspective of cells as shown in the condensed functional view, or from a spatial representation as shown in the compartmental view.

While various embodiments of the invention have been described above, it should be understood that they have been presented by way of example only, and not limitation. Thus, the breadth and scope of the present invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in the art that various changes in form and details may be made therein without departing from the spirit and scope of the invention.

For example, although a certain embodiment of a computer system is described above, other embodiments are possible. Such computer system embodiments can be, for example, a networked or distributed computer system. In addition, certain embodiments of the invention may be practiced with the assistance of a computer system.

All references cited throughout the disclosure are incorporated herein by reference in their entireties for all purposes.

What is claimed is:

1. A method for developing a computer model of an animal joint, comprising:

identifying a plurality of biological processes related to the animal joint, the plurality of biological processes including at least one biological process related to cartilage metabolism; and combining the plurality of biological processes to form a simulation of the animal joint.

2. The method of claim 1, wherein the animal joint is a human joint.

3. The method of claim 1, wherein the plurality of biological processes are related to a biological state of a normal joint.

4. The method of claim 1, wherein at least one biological process from the plurality of biological processes is associated with a biological variable that is a therapeutic agent.

5. The method of claim 1, further comprising:

selecting a therapeutic agent from at least one of methotrexate, steroids, non-steroidal anti-inflammatory drugs, soluble TNF-alpha receptor, TNF-alpha antibody, and interleukin-1 receptor antagonists; and associating the selected therapeutic agent with at least one biological process from the plurality of biological processes.

6. The method of claim 1, wherein the plurality of biological processes are related to a biological state of a diseased joint.

7. The method of claim 6, wherein the biological state is the diseased joint afflicted with at least one of rheumatoid arthritis, osteoporosis, reactive arthritis and osteoarthritis.

8. The method of claim 6, wherein identifying the plurality of biological processes includes identifying a set of biological processes related to changes in biological attributes of the diseased joint, and wherein combining the plurality of biological processes includes combining the set of biological processes to form a simulation of at least one biological attribute of the diseased joint.

9. The method of claim 1, further comprising:

producing a simulated biological attribute associated with a biological state of the animal joint;

comparing the simulated biological attribute with a corresponding biological attribute associated with a reference pattern of the joint; and identifying the computer model as a valid computer model of the animal joint if the simulated biological attribute is substantially consistent with the biological attribute associated with the reference pattern of the animal joint.

10. The method of claim 1, wherein combining the plurality of biological processes includes:

forming a first mathematical relation among biological variables associated with a first biological process from the plurality of biological processes; and forming a second mathematical relation among biological variables associated with the first biological process and a second biological process from the plurality of biological processes.

11. The method of claim 10, further comprising:

creating a set of parametric changes in the first mathematical relation and the second mathematical relation; and producing a simulated biological attribute based on at least one parametric change from the set of parametric changes, the simulated biological attribute being substantially consistent with at least one biological attribute associated with a reference pattern of the animal joint.

12. The method of claim 10, further comprising:

converting a first biological variable into a converted biological variable the value of which changes over time, the first biological variable being associated with at least one from the first mathematical relation and the second mathematical relation; and producing a series of simulated biological attributes based on the converted biological variable, the series of simulated biological attributes being substantially consistent with a corresponding series of biological attribute associated with a reference pattern of the animal joint, the series of simulated biological attributes representing the chronological progression of a biological state of the animal joint.

13. The method of claim 10, further comprising:

converting a parameter into a converted biological variable the value of which changes over time, the parameter being associated with at least one from the first mathematical relation and the second mathematical relation; and producing a series of simulated biological attributes based on the converted biological variable, the series of simulated biological attributes being substantially consistent with a corresponding series of biological attribute associated with a reference pattern of the animal joint, the series of simulated biological attributes representing the chronological progression of a biological state of the animal joint.

14. A processor-readable medium comprising code representing instructions to cause a processor to:

define a plurality of biological processes related to a biological state of an animal joint, the plurality of biological processes including at least one of a first set of biological processes related to tissue inflammation and a second set of biological processes related to cartilage metabolism; and define a plurality of mathematical relationships related to interactions among biological variables associated with the plurality of biological processes, at least two biological processes from the plurality of biological processes being associated with the plurality of mathematical relationships, a combination of the plurality of biological processes and the plurality of mathematical relationships defining a simulation of the biological state of the animal joint.

15. The processor-readable medium of claim 14, wherein the first set of biological processes include at least one biological process related to synovial, tissue inflammation.

16. The processor-readable medium of claim 14, wherein at least one biological process from the plurality of biological processes is associated with a biological variable that is a therapeutic agent.

17. The processor-readable medium of claim 14, further comprising code representing instructions to cause the processor to:

select a therapeutic agent from at least one group of methotrexate, steroids, non-steroidal anti-inflammatory drugs, soluble TNF-alpha receptor, TNF-alpha antibody, and interleukin-1 receptor antagonists; and associate the selected therapeutic agent with at least one biological process from the plurality of biological processes.

18. The processor-readable medium of claim 14, further comprising code representing instructions to cause the processor to:

define a first compartment, the first compartment including the first set of biological processes, and define a second compartment, the second compartment including the second set of biological processes.

19. The processor-readable medium of claim 18, further comprising code representing instructions to cause the processor to:

define a third set of biological processes related to the interaction of the first compartment with the second compartment.

20. The processor-readable medium of claim 14, wherein the biological state is the state of a diseased joint.

21. The processor-readable medium of claim 20, wherein the biological state is the state is the state of a diseased joint afflicted with at least one of rheumatoid arthritis, osteoporosis, reactive arthritis or osteoarthritis, reactive arthritis, and osteoarthristis.

22. The processor-readable medium of claim 20, wherein upon execution of the code, a simulated biological attribute for the biological state of the diseased joint is produced, the simulated biological attribute being substantially consistent with at least one biological attribute associated with a reference pattern of the diseased joint.

23. A processor-readable medium comprising code representing instructions to cause a processor to:

define a plurality of compartments including a plurality of biological processes related to biological state of an animal joint, the plurality of compartments including at least one of:

a first compartment, the first compartment including a first set of biological processes related to synovial tissue a second compartment, the second compartment including a second set of biological processes related to cartilage tissue, the plurality of compartments defining a simulation of the biological state of the animal joint.

24. The processor-readable medium of claim 23, further comprising code representing instructions to cause the processor to:

define a first set of mathematical relations associated with the first set of biological processes and associated with interactions among biological variables associated with the first set of biological processes, and define a set of mathematical relations associated with the second set of biological processes and associated with interactions among biological variables associated with the second set of biological processes.

25. The processor-readable medium of claim 23, further comprising code representing instructions to cause the processor to:

define a third set of biological processes related to the interaction of the first compartment with the second compartment.

26. A method for developing a computer model of a diseased joint, comprising:

receiving a plurality of user-selected indications to define a plurality of biological processes, each biological process from the plurality of biological processes being based on data that relates changes in biological states to biological attributes of the diseased joint, the plurality of biological processes including a set of biological processes related to at least one of tissue inflammation and tissue hyperplasia;

producing a simulated biological attribute associated with at least one biological attribute of the diseased joint based on the combined plurality of biology processes; and assessing a validity of the computer model based on a comparison between the simulated biological attribute and a corresponding biological attribute associated with a reference pattern of the diseased joint.

27. The method of claim 26, wherein the diseased joint is afflicted with at least one of rheumatoid arthritis, osteoporosis, reactive arthritis and osteoarthritis.

28. The method of claim 26, wherein at least one biological process from the plurality of biological processes is associated with a biological variable that is a therapeutic agent.

29. The method of claim 26, further comprising:

selecting a therapeutic agent from at least one of methotrexate, steroids, non-steroidal anti-inflammatory drugs, soluble TNF-alpha receptor, TNF-alpha antibody, and interleukin-1 receptor antagonists; and associating the selected therapeutic agent with at least one biological process from the plurality of biological processes.

30. A computer model of an animal joint, comprising:

a computer-readable memory storing:

code to define a plurality of biological processes related to a biological state of the animal joint, at least one biological process from the plurality of biological processes being associated with a therapeutic agent; and code to define a plurality of mathematical relationships related to interactions among biological variables associated with the plurality of biological processes, at least two biological processes from the plurality of biological processes being associated with the plurality of mathematical relationships, a combination of the code to define plurality of biological processes and the code to define the plurality of mathematical relationships defining a simulation of the biological state of the animal joint; and a processor coupled to the computer-readable memory, the processor configured to execute the codes.

31. The computer model of claim 30, wherein the plurality of biological processes include a biological process related to at least one of cartilage metabolism, tissue inflammation, and tissue hyperplasia.

32. The computer model of claim 30, wherein the plurality of biological process include a biological process related to at least one of inflammatory mediators, proteases, fibroblast-like synoviocyte population, macrophage population, T lymphocyte population, B lymphocyte population, and dendritic cell population.

33. The computer model of claim 30, further comprising:

code to select the therapeutic agent from at least one of methotrexate, steroids, non-steroidal anti-inflammatory drugs, soluble TNF-alpha receptor, TNF-alpha antibody, and interleukin-1 receptor; and antagonists; and code to associate the selected therapeutic agent with at least one biological process from the plurality of biological processes.

34. The computer model of claim 30, wherein the plurality of biological processes include a first set of biological processes related to synovial tissue and a second set of biological processes related to cartilage tissue, the computer model further comprising:

code to define a first compartment, the first compartment including the first set of biological processes, and code to define a second compartment, the second compartment including the second set of biological processes.

35. The computer model of claim 34, further comprising:

code to define a third set of biological processes related to the interaction of the first compartment with the second compartment.

36. The computer model of claim 30, wherein the biological state is the state of a diseased joint.

37. The computer model of claim 36, wherein the biological state is the state of the diseased joint afflicted with at least one of rheumatoid arthritis, osteoporosis, reactive arthritis and osteoarthritis.

38. The computer model of claim 36, wherein upon execution of the computer model, a simulated biological attribute for the biological state of the diseased joint is produced, the simulated biological attribute being substantially consistent with at least one biological attribute associated with a reference pattern of the diseased joint.

39. A method for developing an analytical model of an animal joint, comprising:

identifying a plurality of biological processes related to the animal joint, the plurality of biological processes including at least one biological process related to a set of inflammatory mediators; and combining the plurality of biological processes to form an analytical representation of the animal joint.

40. The method of claim 39, wherein the plurality of biological processes are related to a biological state of a normal joint.

41. The method of claim 39, wherein the plurality of biological processes are related to a biological state of a diseased joint.

42. The method of claim 41, wherein the biological state is the state of the diseased joint afflicted with at least one of rheumatoid arthritis, osteoporosis, reactive arthritis, and osteoarthritis.

43. The method of claim 41, comprising:

wherein identifying the plurality of biological processes includes identifying a step of biological processes related to changes in biological attributes of the diseased joint, and wherein combining the plurality of biological processes includes combining the set of biological processes to form an analytical representation of a least one biological attribute of the diseased joint.

44. The method of claim 39, further comprising:

producing an analytical representation of a biological attribute associated with a biological state of the animal joint;

producing an analytical representation of the biological attribute with a corresponding biological attribute associated with a reference pattern of the animal joint; and identifying the analytical model as a valid model of the animal joint; and identifying the analytical model as a valid model of the animal joint if the analytical representation of the biological attribute is substantially consistent with the biological attribute associated with the reference pattern of the animal joint.

45. The method of claim 39, wherein combining the plurality of biological processes includes:

forming a first mathematical relation among biological variables associated with a first biological process from the plurality of biological processes; and forming a second mathematical relation among biological variables associated with the first biological process and a second biological process from the plurality of biological processes.

46. The method of claim 39, wherein the animal joint is a human joint.

* * * * *